(12) United States Patent
Grawunder et al.

(10) Patent No.: US 12,275,789 B2
(45) Date of Patent: Apr. 15, 2025

(54) HUMAN ANTIBODIES BINDING TO ROR2

(71) Applicant: NBE-Therapeutics AG, Basel (CH)

(72) Inventors: Ulf Grawunder, Hersberg (CH); Roger Beerli, Adlikon bei Regensdorf (CH); Ina Hellmann, Huningue (FR); Lorenz Waldmeier, Basel (CH)

(73) Assignee: NBE-Therapeutics AG, Basel (CH)

( * ) Notice: Subject to any disclaimer, the term of this patent is extended or adjusted under 35 U.S.C. 154(b) by 216 days.

(21) Appl. No.: 17/814,488

(22) Filed: Jul. 22, 2022

(65) Prior Publication Data

US 2022/0372143 A1     Nov. 24, 2022

Related U.S. Application Data

(62) Division of application No. 16/632,811, filed as application No. PCT/EP2018/069826 on Jul. 20, 2018, now Pat. No. 11,447,546.

(30) Foreign Application Priority Data

Jul. 20, 2017 (EP) ..................... 17182355

(51) Int. Cl.
    *C07K 16/28*         (2006.01)
    *A61K 47/68*        (2017.01)

(52) U.S. Cl.
    CPC ...... *C07K 16/2803* (2013.01); *A61K 47/6809* (2017.08); *A61K 47/6849* (2017.08); *A61K 47/6851* (2017.08); *C07K 2317/21* (2013.01); *C07K 2317/31* (2013.01); *C07K 2317/33* (2013.01); *C07K 2317/51* (2013.01); *C07K 2317/515* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,679,492 B2 | 3/2014 | Blein et al. | |
| 9,872,923 B2 * | 1/2018 | Grawunder | A61P 37/02 |
| 9,969,800 B2 | 5/2018 | Igawa et al. | |
| 11,447,546 B2 * | 9/2022 | Grawunder | A61K 47/6851 |
| 2016/0136298 A1 * | 5/2016 | Grawunder | A61P 25/00 |
| | | | 435/68.1 |
| 2018/0127503 A1 | 5/2018 | Liu et al. | |

FOREIGN PATENT DOCUMENTS

| | | | |
|---|---|---|---|
| WO | 2009055669 A2 | 4/2009 | |
| WO | 2013103637 A1 | 7/2013 | |
| WO | WO-2014140317 A2 * | 9/2014 | ............ A61K 47/65 |
| WO | 2015171938 A1 | 11/2015 | |
| WO | 2016142768 A1 | 9/2016 | |

OTHER PUBLICATIONS

Strop et al., Chemistry and Biology 20: 161-167 (Year: 2013).*
Stefan et al., Molecular Therapeutics 16(5): 879-892 (Year: 2017).*
Beerli et al., PLOS one 10(7): e0131177 (Year: 2015).*
Zufan Debebe et al., "ROR2 as a therapeutic target in cancer", Pharmacology and Therapeutics, vol. 150, pp. 143-148 (2015) (6 pages).
R&D, "Human ROR2 Antibody, catalog No. MAB2064", R&D Catalog, Oct. 13, 2015, p. 1 (1 page).
Abcam: "Anti-ROR2 Antibody [6F2D10] ab201962", Abcam Catalog, Mar. 1, 2015, pp. 1-3 (3 pages).
C. Lloyd et al., "Modelling the human immune response: performance of a 10exp11 human antibody repertoire against a broad panel of therapeutically relevant antigens", Protein Engineering, Design and Selection, 2009, vol. 22, pp. 159-168 (10 pages).
Edwards et al., "The remarkable flexibility of the human antibody repertoire; isolation of over one thousand different antibodies to a single protein, BLyS", 2003, vol. 14, No. 334, pp. 103-118 (16 pages).
Rudikoff et al., "Single amino acid substitution altering antigen-binding specificity", 1982, PNAS vol. 79, pp. 1979-1983 (5 pages).
Kussie et al., "A single engineered amino acid substitution changes antibody fine specificity", 1994, J. Immunol. vol. 152, pp. 146-152 (8 pages).
Chen et al., "Enhancement and destruction of antibody function by somatic mutation: unequal occurrence is controlled by V gene combinatorial associations", 1995, EMBO J., vol. 14, pp. 2784-2794 (11 pages).
Wu et al., "Humanization of a Murine Monoclonal Antibody by Simultaneous Optimization of Framework and CDR Residues", 1999, J. Mol. Biol., vol. 294, pp. 151-162 (12 pages).
Office Action dated Dec. 12, 2022, issued in the counterpart European patent application No. 18749740.9.

* cited by examiner

*Primary Examiner* — Phuong Huynh
(74) *Attorney, Agent, or Firm* — Morgan, Lewis & Bockius LLP

(57) ABSTRACT

The present invention relates to fully human antibodies and conjugates thereof, which specifically bind to the extracellular domain of receptor tyrosine kinase-like orphan receptor 2 (ROR2).

9 Claims, 12 Drawing Sheets

Specification includes a Sequence Listing.

HUMAN ANTIBODIES BINDING TO ROR2

CROSS REFERENCE TO RELATED APPLICATIONS

This application is a divisional of U.S. patent application Ser. No. 16/632,811, U.S. Pat. No. 11,447,546, filed Jan. 21, 2020, which claims the benefit of priority under 35 U.S.C. § 371 of International Application No. PCT/EP2018/069826, filed Jul. 20, 2018, which claims the benefit of priority of European Application No. 17182355.2, filed Jul. 20, 2017. The contents of these earlier filed applications are hereby incorporated by reference herein in their entireties.

REFERENCE TO SEQUENCE LISTING

The Sequence Listing associated with this application is provided in text format in lieu of a paper copy, and is hereby incorporated by reference into the specification. The sequence listing submitted Jul. 22, 2022 as a text file named "127755-5007-US01_Sequence_Listing.xml", created on Jul. 22, 2022, and having a size of 191,000 bytes, is hereby incorporated by reference pursuant to 37 C.F.R. § 1.52(e)(5).

FIELD OF THE INVENTION

The present invention relates to human antibodies binding to ROR2, preferably to human ROR2 (hROR2), and fragments and conjugates thereof, as well as to uses thereof.

BACKGROUND OF THE INVENTION

Cancer is one of the leading causes of death. It is a class of diseases caused by malignant transformation of healthy cells, resulting from genetic alterations, like chromosomal translocations, mutations in tumor suppressor genes, transcription factors or growth-factor receptors, leading to the immortalization of the cells. If the immortalization is combined with excessive proliferation, the immortalized cells generate tumors, with or without metastasis (in case of solid tumors), or leukemias and lymphomas (cancers of the blood). Defective apoptosis, or programmed cell death, can further contribute to malignant transformation of cells leading to cancer.

A family of membrane-associated receptor tyrosine kinases, consisting of the receptor tyrosine kinase orphan receptors-1 and -2 (ROR1 and ROR2) have been described as specifically associated with particular cancers (Rebagay et al. (2012) *Front Oncol.* 2(34):1-8: doi 10.3389/onc.2012.00034), while being largely absent in expression on healthy tissue with, a few exceptions e.g. in case of ROR1 (Balakrishnan et al. (2016) *Clin Cancer Res*. doi: 10.1158/1078-0432). Whether or not ROR expression is functionally associated with tumorigenesis remains unclear. However, due to the very tumor-selective expression of ROR family members, they represent relevant targets for targeted cancer therapies. Importantly, human ROR2 (hROR2) has been described to be expressed on tumor cells in neuroblastoma, sarcoma (and especially osteosarcoma), renal cell carcinoma, breast cancer, testicular cancer, ovarian cancer, pancreatic cancer, kidney cancer, renal cancer, gastric cancer, prostate cancer, head and neck cancer, melanoma, squamous cell carcinoma, multiple myeloma and other cancers.

Receptor tyrosine kinase orphan receptors-1 and -2, ROR1 and ROR2, are the only two family members defining a new receptor tyrosine kinase family, based on the overall structural design and some functional similarities. Both ROR1 and ROR2 proteins are type I-single pass trans-membrane receptors with an extracellular domain (ECD) consisting of an immunoglobulin domain, a cysteine rich frizzled domain and a Kringle domain. These three extracellular domains are followed by a trans-membrane domain connecting the ECD to an intracellular portion of the protein comprising kinase domains (Rebagay et al. (2012) *Frontiers Oncol.* 2: 1-8).

The human ROR1 and ROR2 proteins are 58% homologous between each other, but each of the ROR proteins is highly conserved between species. This represents a challenge for the development of human ROR2 specific monoclonal antibodies and very few antibodies are known.

In normal physiology, hROR2 is responsible for aspects of bone and cartilage growth during embryonic development. After birth, expression of hROR2 is downregulated and hROR2 is normally undetectable or expressed at very low levels in adult tissues. Weak expression of hROR2 has only been reported in stomach and thyroid issue (Morioka et al. (2009) *Cancer Sci.* 100: 1227-1233). hROR2 has previously been recognized as a target for the development of hROR2 specific antibodies (WO 2013/103637 A1, WO 2016/142768 A1).

There is a need for high-quality anti-ROR2 antibodies that can be used as a basis for the development of antibody-based targeted therapies of ROR2-expressing cancers. In particular, there is also a need for anti-ROR2 antibodies with excellent developability parameters, including a low propensity for aggregation, and that exhibit high thermal stability, which are typically obtained by B cells from immunized animals. Further, there is a need for antibodies that, in addition to binding human ROR2, also bind to ROR2 of standard toxicology species, like mice, rats, rabbits and/or cynomolgus monkeys, and especially to both cynomolgus and mouse ROR2, allowing toxicological characterization of antibody-based targeted therapies in anticipation of human clinical trials. Additionally, for human therapy there is a need for antibodies that are essentially fully human antibodies with lowest immunogenicity risk upon systemic administration in human subjects. There is also a need for additional diagnostic tools for detecting ROR2 expressions in ROR2-related disease conditions. The instant invention is directed to addressing these and other needs.

SUMMARY OF THE INVENTION

The present invention provides fully human antibodies which specifically bind to the extracellular domain of receptor tyrosine kinase-like orphan receptor 2 (ROR2). The invention and general advantages of its features will be discussed in detail below.

DETAILED DESCRIPTION OF THE INVENTION

Figure 1:
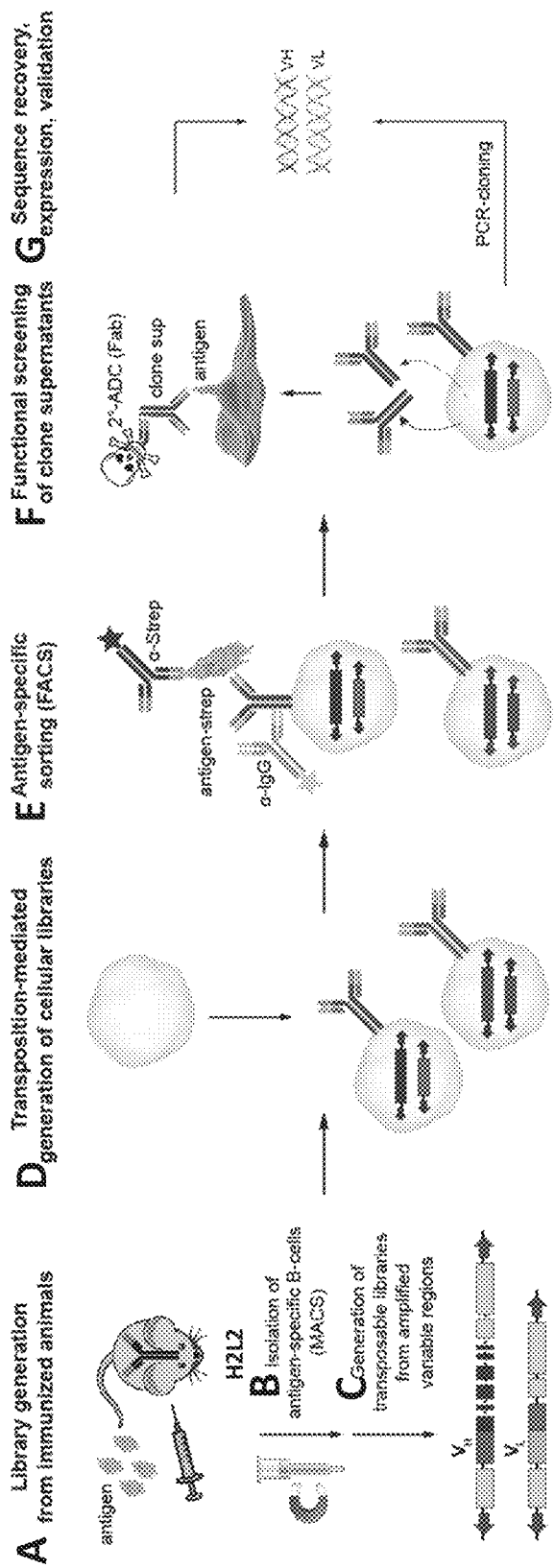
FIG. 1. Schematic representation of the process used to develop novel human antibodies targeting hROR2. (A) In a first step, human antibody transgenic mice (H2L2 mice) (described in WO 2010/070263 A1) were immunized with the entirely extracellular domain of C-terminally tagged with a Twin-Strep-tag (hROR2-TwinStrep) (B) Then, splenic B cells binding to hROR2-TwinStrep were enriched from immunized H2L2 mice by Magnetic Activated Cell Sorting (MACS). (C) From the isolated splenic B cells transposable expression vector libraries for human IgG1 were generated by PCR-cloning of variable heavy and light chain domains from the isolated hROR2-binding splenic B cells. (D) This was followed by transposition-mediated generation of cellular libraries displaying full-length human IgG1 libraries stably expressing the PCR-cloned antibody libraries in immortalized preB cells. (E) FACS-based screening of surface-displayed IgG1 antibodies for hROR2 binding and isolation of single cell clones by FACS. (F) Functional screening IgG1 antibodies of selected clonal supernatants. (G) PCR amplification of antibodies from selected clones.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'→3'.

In one aspect, the invention provides novel, high-affinity binding domains of fully human monoclonal antibodies that specifically bind to the extracellular domain of receptor tyrosine kinase-like orphan receptor 2 (ROR2). In one embodiment, ROR2 is human ROR2 (hROR2).

Such monoclonal antibodies have been selected from diverse antibody libraries generated by challenging human antibody light and heavy variable domain transgenic mice (WO 2010/070263 A1, H2L2 mice) with recombinant extracellular domain of the hROR2 antigen followed by generating and screening cellular IgG1 display libraries from hROR2 challenged H2L2 mice using DNA-transposable vectors for transfection into 63-12 mouse preB-cells according to WO 2014/013026 A1. Mammalian cells displaying the antibodies according to WO 2014/013026 A1 were screened using antigen-specific cell sorting (FACS), including single-cell sorting. Eventually, antibodies secreted in the supernatant of single-cell sorted clones were subjected to antigen-binding evaluation by ELISA and secondary cancer cell killing assays (i.e., wherein a secondary antibody coupled to a toxin binds to the antigen-bound anti-hROR2 antibody at the cell surface, and is internalised to effect cell killing). Coding sequences of variable heavy and light chain domains have been identified from selected cell clones displaying hROR2-specific binding and functional characterization involving cell killing of hROR2 expressing target cells via a Fab-based toxin-conjugated secondary reagent. By this strategy novel fully human monoclonal antibodies for hROR2 of high quality and favorable functional properties have been identified.

In a second aspect of the invention, antibody drug conjugates (ADCs) based on said anti-ROR2 antibodies, antibody-based binding proteins or antigen-binding fragments thereof, with one or more toxins, and in particular with an ultra-potent anthracycline toxin, are provided. In particular, such ADCs are generated by site-specific conjugation, achieved by enzymatic conjugation using sortase enzyme as disclosed in WO 2014/140317 A1, which is incorporated by reference herein. One particular ultra-potent anthracycline toxin with high potency has been disclosed in WO 2016/102679 A1, which is incorporated by reference herein.

In a third aspect of the invention, antibody effector conjugates (AECs) based on said anti-ROR2 antibodies, antibody-based binding proteins or antigen-binding fragments thereof, conjugated to one or more labels, are provided.

Additionally, the invention provides chimeric antigen receptors (CARs) and T cells engineered with these CARs, i.e. CAR-T cells, employing said anti-ROR2 antibodies, derivatives, modified formats or fragments.

Additionally, the invention provides bi- or multispecific antibodies comprising the binding domains of the disclosed anti-ROR2 antibodies, in bi- or multispecific antibody formats comprising at least one binding domain specific for another target, for instance, but not limited to targets that recruit and/or activate cells of the immune system, like T cells or NK cells. Such other binding domains may be specific for CD3, CD16, CD32, CD56, CD64 or other markers specific for T and NK cells.

In another aspect, the present invention refers to isolated or substantially purified polynucleotides encoding the variable region of the immunoglobulin heavy chain or immunoglobulin light chain of the fully human anti-ROR2 antibody, antibody-based binding protein or antigen-binding fragment thereof, and to expression vectors harboring such polynucleotides, as well as to host cells transformed or transfected with these polynucleotides, and methods of making anti-ROR2 antibodies, antibody-based binding proteins and antigen-binding fragments.

In another aspect, the present invention refers to a fully human anti-ROR2 antibody, antibody-based binding protein or antigen-binding fragment thereof, or ADC, a bi- or multispecific antibody, or a chimeric antigen receptor (CAR), as described herein, for use in the treatment of a subject that is suffering from, at risk of developing, and/or diagnosed with a neoplastic disease.

In another aspect, the present invention refers to a method for treating a subject suffering from, at risk of developing, and/or diagnosed with a neoplastic disease with a human anti-hROR2 antibody, antibody-based binding protein or antigen-binding fragment thereof, or ADC, or a bi- or multispecific antibody, or a CAR engineered cell, as described herein.

In another aspect, the present invention refers to a method for detecting a neoplastic disease or an immune disease or disorder suitable for treatment with an anti-ROR2 antibody, antibody-based binding protein or antigen-binding fragment thereof, or AEC.

Definitions

Unless defined otherwise, all technical and scientific terms used herein have the same meaning as commonly understood by those of ordinary skill in the art to which this invention pertains. In addition, the following definitions are provided to assist the reader in the practice of the invention.

The term "human antibody" refers to an antibody, antibody-based binding protein, modified antibody format retaining target binding capacity, or antibody derivative or fragment retaining target binding capacity that contains sequences derived from human immunoglobulins such that substantially all of the heavy and light chain CDR1 and CDR2 regions are of human origin, and substantially all of the heavy and light chain FR regions 1, 2, 3, and 4 correspond to those of a human immunoglobulin sequence either with or without a limited number of somatic mutations that may be introduced into individual heavy and light chain CDR1 and CDR2 and FR1, 2, 3, and 4 variable domain sequences.

The terms "antibody", "antibody-based binding protein", "modified antibody format retaining target binding capacity", "antibody derivative or fragment retaining target binding capacity" refer to polypeptide chain(s) which exhibit a strong monovalent, bivalent or polyvalent binding to a given antigen, epitope or epitopes. Antibodies, antibody-based binding proteins and antigen-binding fragments used in the invention can be generated using any suitable technology, e.g., hybridoma technology, ribosome display, phage display, gene shuffling libraries, semi-synthetic or fully synthetic libraries or combinations thereof. Antibodies, antibody-based binding proteins and antigen-binding fragments of the invention include intact antibodies and antibody fragments or antigen-binding fragments that contain the antigen-binding portions of an intact antibody and retain the capacity to bind the cognate antigen. Unless otherwise specified herein, all peptide sequences, including all antibody and antigen-binding fragment sequences are referred to in N→C order.

An intact antibody typically comprises at least two heavy (H) chains (about 50-70 kD) and two light (L) chains (about 25 kD) inter-connected by disulfide bonds. The recognized immunoglobulin genes encoding antibody chains include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Each heavy chain of an antibody is comprised of a heavy chain variable region (VH) and a heavy chain constant region. In the case of IgG, the heavy chain constant region is comprised of three domains. CH1, CH2 and CH3. Each light chain is comprised of a light chain variable region (VL) and a light chain constant region. The light chain constant region is comprised of one domain, CL. The variable regions of the heavy and light chains contain a binding domain that interacts with an antigen. The constant regions of the antibodies may mediate the binding of the immunoglobulin to host tissues or factors, including various cells of the immune system and the first component (Clq) of the classical complement system. Monoclonal antibodies (mAbs) consist of identical antibodies molecules.

The VH and VL regions of an antibody can be further subdivided into regions of hypervariability, also termed complementarity-determining regions (CDRs), which are interspersed with the more conserved framework regions (FRs). Each VH and VL is composed of three CDRs and four FRs, arranged from amino-terminus to carboxyl-terminus in the following order: FR1, CDR1, FR2, CDR2, FR3, CDR3, FR4. The locations of CDR and FR regions and a numbering system have been defined. e.g., the IMGT system (Lefranc M P et al., 2015), or the Kabat numbering scheme.

Antibodies, antibody-based binding proteins and antigen-binding fragments of the invention also encompass single chain antibodies. The term "single chain antibody" refers to a polypeptide comprising a VH domain and a VL domain in polypeptide linkage, generally linked via a spacer peptide, and which may comprise additional domains or amino acid sequences at the amino- and/or carboxyl-termini. For example, a single-chain antibody may comprise a tether segment for linking to the encoding polynucleotide. As an example, a single chain variable region fragment (scFv) is a single-chain antibody. Compared to the VL and VH domains of the Fv fragment that are coded for by separate genes, a scFv has the two domains joined (e.g., via recombinant methods) by a synthetic linker. This enables them to be made as a single protein chain in which the VL and VH regions pair to form monovalent molecules.

Examples of antibody-based binding proteins are polypeptides in which the binding domains of the antibodies are combined with other polypeptides or polypeptide domains, e.g. alternative molecular scaffolds, Fc-regions, other functional or binding domains of other polypeptides or antibodies resulting in molecules with addition binding properties, e.g. bi- or multispecific proteins or antibodies. Such polypeptides can create an arrangement of binding or functional domains normally not found in naturally occurring antibodies or antibody fragments.

Examples of antigen-binding fragments include (i) a Fab fragment, a monovalent fragment consisting of the VL, VH, CL and CH1 domains: (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an intact antibody; (v) disulfide stabilized Fvs (dsFvs) which have an interchain disulfide bond engineered between structurally conserved framework regions: (vi) a single domain antibody (dAb) which consists of a VH or VL domain (see, e.g., Ward et al., Nature 341:544-546, 1989); and (vii) an isolated complementarity determining region (CDR) as a linear or cyclic peptide.

The anti-ROR2 antibodies, antibody-based binding proteins and antigen-binding fragments described herein can be produced by enzymatic or chemical modification of the intact antibodies, or synthesized de novo using recombinant DNA methodologies. Methods for generating these antibodies, antibody-based binding proteins and antigen-binding molecules are all well known in the art. In particular, scFv antibodies can be obtained using methods described in, e.g., Bird et al., *Science* 242:423-426, 1988; and Huston et al., *Proc. Natl. Acad. Sci. USA* 85:5879-5883, 1988. Fv antibody fragments can be generated as described in Skerra and Pluckthun, *Science* 240:1038-41, 1988. Disulfide-stabilized Fv fragments (dsFvs) can be made using methods described in, e.g., Reiter et al., *Int. J. Cancer* 67:113-23, 1996. Similarly, single domain antibodies (dAbs) can be produced by a variety of methods described in, e.g., Ward et al., *Nature* 341:544-546, 1989; and Cai and Garen, *Proc. Natl. Acad. Sci. USA* 93:6280-85, 1'96. Camelid single domain antibodies can be produced using methods well known in the art, e.g., Dumoulin et al., *Nat. Struct. Biol.* 11:500-515, 2002; Ghahroudi et al., *FEBS Letters* 414:521-526, 1997; and Bond et al., *J. Mol. Biol.* 332:643-55, 2003. Other types of antigen-binding fragments (e.g., Fab, F(ab')$_2$ or Fd fragments) can also be readily produced with routinely practiced immunology methods. See, e.g., Harlow & Lane, *Using Antibodies. A Laboratory Manual*, Cold Spring Harbor Laboratory Press, Cold Spring Harbor, New York, 1998.

The anti-ROR2 antibodies, antibody-based binding proteins or antigen-binding fragments of the invention can be produced by any suitable technique, for example, using any suitable eukaryotic or non-eukaryotic expression system. In certain embodiments, the antibody, antibody-based binding protein or antigen-binding fragment is produced using a mammalian expression system. Some specific techniques for generating the antibodies, antibody-based binding proteins or antigen-binding fragments or antigen-binding fragments of the invention are exemplified herein. In some embodiments, the antibodies, antibody-based binding proteins or antigen-binding fragments of the invention can be produced using a suitable non-eukaryotic expression system such as a bacterial expression system. Bacterial expression systems can be used to produce fragments such as a F(ab)2, Fv, scFv, IgGACH2, F(ab')2, scFv2CH3, Fab, VL, VH, scFv4, scFv3, scFv2, dsFv. Fv, scFv-Fc, (scFv)2, and diabodies. Techniques for altering DNA coding sequences to produce such fragments are known in the art.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, FASTA, and TFASTA in the Wisconsin Genetics Software Package, Genetics Computer Group, Madison, WI); or by manual alignment and visual inspection (see, e.g., Brent et al., *Current Protocols in Molecular Biology*, John Wiley & Sons, Inc. (Ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., *J. Mol. Biol.* 215:403410, 1990, respectively.

Percent (%) identity of peptide sequences can be calculated, for example, as 100×[(identical positions)/min(TGA, TGB)], where TGA and TGB are the sum of the number of residues and internal gap positions in peptide sequences A and B in the alignment that minimizes TGA and TGB. See, e.g., Russell et al, *J. Mol. Biol.*, 244: 332-350 (1994).

Artificial T cell receptors (also known as chimeric T cell receptors, chimeric immunoreceptors, chimeric antigen receptors (CARs) or T-bodies) are engineered receptors, which graft an arbitrary specificity onto an immune effector cell. Typically, these receptors are used to graft the specificity of a monoclonal antibody onto a T cell; with transfer of their coding sequence facilitated by retroviral or lentiviral vectors or by transposons. CAR-engineered T cells are genetically engineered T cells armed with chimeric receptors whose extracellular recognition unit is comprised of an antibody-derived recognition domain and whose intracellular region is derived from lymphocyte stimulating moiety(ies). The structure of the prototypic CAR is modular, designed to accommodate various functional domains and thereby to enable choice of specificity and controlled activation of T cells. The preferred antibody-derived recognition unit is a single chain variable fragment (scFv) that combines the specificity and binding residues of both the heavy and light chain variable regions of a monoclonal antibody, but also other antibody-derived formats like Fab fragments, V-domains etc. may be employed to confer a desired CAR specificity to CAR engineered T cells. The most common lymphocyte activation moieties include a T-cell costimulatory (e.g. CD28) domain in tandem with a T-cell triggering (e.g. CD3zeta) moiety, but also other signaling domains, like 4-1BB can be employed in the intracellular portion of CARs. By arming effector lymphocytes (such as T cells and natural killer cells) with such chimeric receptors, the engineered cell is redirected with a predefined specificity to any desired target antigen, in a non-HLA restricted manner. CAR constructs are introduced ex vivo into T cells from peripheral lymphocytes of a given patient using retroviral or lentiviral vectors or transposons. Following infusion of the resulting CAR-engineered T cells back into the patient, they traffic, reach their target site, and upon interaction with their target cell or tissue, they undergo activation and perform their predefined effector function. Therapeutic targets for the CAR approach include cancer and HIV-infected cells, or autoimmune effector cells.

The terms "treat," "treating," "treatment," and "therapeutically effective" used herein do not necessarily imply 100% or complete treatment. Rather, there are varying degrees of treatment recognized by one of ordinary skill in the art as having a potential benefit or therapeutic effect. In this respect, the inventive method can provide any amount of any level of treatment. Furthermore, the treatment provided by the inventive method can include the treatment of one or more conditions or symptoms of the disease being treated.

A "vector" is a replicon, such as plasmid, phage or cosmid, to which another polynucleotide segment may be attached so as to bring about the replication of the attached segment. Vectors capable of directing the expression of genes encoding for one or more polypeptides are referred to as "expression vectors".

DETAILED DESCRIPTION OF EMBODIMENTS

Invention Aspects Relating to Binding of Human ROR2

In one aspect, the present invention refers to a human anti-ROR2 antibodies, antibody-based binding proteins (incl. bi- or multi-specific antibodies), antigen-binding fragments thereof. AECs, ADCs, or CARs having the same binding specificity for ROR2 (and especially for hROR2 comprising or consisting of SEQ ID NO. 1), i.e., binding to the same ROR2 epitope and/or competing for ROR2 binding, as ROR2 specific antibodies containing an immunoglobulin heavy chain variable region sequence and an immunoglobulin light chain variable region sequence pair, as per Table 2. In particular, the present invention refers to human anti-ROR2 antibodies, antibody-based binding proteins (incl. bi- or multi-specific antibodies), antigen-binding fragments thereof, AECs, ADCs, or CARs having the same binding specificity for ROR2 (and especially for hROR2 comprising or consisting of SEQ ID NO. 1).

In one aspect, a fully human antibody, or a derivative, modified format or fragment thereof, is provided, which specifically binds to the extracellular domain of receptor tyrosine kinase-like orphan receptor 2 (ROR2).

According to one embodiment, the antibody, derivative, modified format or fragment is an antibody, an antibody-based binding protein, a modified antibody format retaining target binding capacity, antibody derivative or fragment retaining target binding capacity.

In one embodiment, the antibody, derivative, modified format or fragment, (i) binds to the same ROR2 epitope as and/or (ii) competes for ROR2 binding with an antibody comprising an Ig heavy chain variable region sequence and an Ig light chain variable region sequence, respectively, shown in:
(i) SEQ ID NO:2 and SEQ ID NO:3;
(ii) SEQ ID NO:4 and SEQ ID NO:5;
(iii) SEQ ID NO:6 and SEQ ID NO:7;
(iv) SEQ ID NO:8 and SEQ ID NO:9;
(v) SEQ ID NO:10 and SEQ ID NO: 11;
(vi) SEQ ID NO:12 and SEQ ID NO:13;
(vii) SEQ ID NO:14 and SEQ ID NO:15;
(vii) SEQ ID NO:16 and SEQ ID NO:17;
(ix) SEQ ID NO: 18 and SEQ ID NO:19
(x) SEQ ID NO:20 and SEQ ID NO:21;
(xi) SEQ ID NO:22 and SEQ ID NO:23; or
(xii) SEQ ID NO.24 and SEQ ID NO:25.

In one other embodiment, the antibody, derivative, modified format or fragment comprises a heavy chain variable region sequence and a light chain variable region sequence, respectively, one or both of which are at least 90%, preferably at least 95%, more preferably at least 98%, even more preferably at least 99% and most preferably 100% identical, to the heavy chain variable region sequence/light chain variable region sequence pairs shown above.

TABLE L

SEQ ID NO. 1: amino acid sequence from the extracellular domain of human ROR2 (hROR2), based on sequence NP_004551.2 from GenBank

| SEQ ID NO. | Amino Acid Sequence |
|---|---|
| SEQ ID NO. 1 | EVEVLDPNDPLGPLDGQDGPIPTLKGYPLNFLEPVNNTTTVQGQTAILHCKVAGNPPPNV RWLKNDAPVVOEPRRIIIRKTEYGSRLRIODLDTTDTGYYQCVATNGMKTITATGVLFVR LGPTHSPNHNFQDDYHEDGFCQPYRGIACARFIGNRTIYVDSLQMQGEIENRITAAFTMI |

TABLE L-continued

SEQ ID NO. 1: amino acid sequence from the extracellular domain of human ROR2 (hROR2), based on sequence NP_004551.2 from GenBank

| SEQ ID NO. | Amino Acid Sequence |
|---|---|
| | GTSTHLSDQCSQFAIPSFCHFVFPLCDARSRTPKPRELCRDECEVLESDLCRQEYTIARS NPLILMRLQLPKCEALPMPESPDAANCMRIGIPAERLGRYHQCYNGSGMDYRGTASTTKS GHQCQPWALQHPHSHHLSSTDFPELGGGHAYCRNPGGQMEGPWCFTQNKNVRMELCDVPS CSPRDSSKMG |

TABLE 2

Amino acid sequences of SEQ ID NO. 2-25 and 75-92, comprising variable and constant domains, wherein the constant domain is underlined

| SEQ ID NO. Name | Amino Acid Sequence (with constant domain underlined) |
|---|---|
| SEQ ID NO. 2 MK-3B12 HC amino acid sequence | EVQLVESGPGLLKPSETLSLTCAVSGYSISSGYYWGWIRQPPGKGLEWIGSIYQSGSTHY NPSLKSRVTISVDTSKNQFSLKLTSVTAADTAVYYCAREDRAGWYPFDCWGQGTLVTVSS ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPAPELLGG PSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSRDE LTKNQVSLTCLVKGFYPSDIAVEWESNGQPENNYKTTPPVLDSDGSFFLYSKLTVDKSRW QQGNVFSCSVMHEALHNHYTQKSLSLSPGR |
| SEQ ID NO. 3 MK-3B12 LC amino acid sequence | DIVMTQSPSTLSASVGDRVTITCRASQSISSWLAWYQQKPGKAPKLLIYKASSLESGVPS RFSGSGSGTEFTLTISSLQPDDFATYYCQQYNNYWTFGQGTKVEIKRTVAAPSVFTFPPS DEQLKSGTASVVCLLNNFYPREAKVQWKVDNALQSGNSQESVTEQDSKDSTYSLSSTLTL SKADYEKHKVYACEVTHQGLSSPVTKSFNRGEC |
| SEQ ID NO. 4 MK-7C3 HC amino acid seqence | EVQLLETGGGVVQPGRSLRLSCVASGFTFRSHGMHWVRQAPGKGLEWVALIWYDGSKKYY ADSVKGRFTISRDNSKNTLYLQMNSLRAEDTAVYYCARVGAGLYLDYWGQGTLVTVSSAS TKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPCPAPELLGGPS VFLFPPKPKDTLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVYTLPPSRDELT KNQVSLTCLVKGFYPSDIAVEWESNGQPENNYKTTPPVLDSDGSFFLYSKLTVDKSRWQQ GNVFSCSVMHEALHNHYTQKSLSLSPGK |
| SEQ ID NO. 5 MK-7C3 LC amino acid sequence | AIRMTQSPSTLSASVGDRVTITCRASQTISNWLAWFQQKPGKAPKVLIYKASSLESGVPS RFSGSGSGTEFTLTISSLQPDDFASYYCQQYNSYSYTFGQGTRLEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| SEQ ID NO. 6 GK-1E5 HC amino acid sequence | EVQLVESGGGVVQPGRSLRLSCAASGPTFRSYGMHWVRQAPGKGLEWVATTWYDGSKKYY TDSVQGRFTISRDNSKNTLYLQMNSLRAEDTAVYYCARPGIAMTGLDYWGQGTLVTVSSA STKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQ QGNVFSCSVMHEALHNHYTQKSLSLSPGK |
| SEQ ID NO. 7 GK-1E5 LC amino acid sequence | DIQLTQSPSTLSASVGDRVTITCRASQSISSWLAWYQQKPGKAPKLLIYKASSLESGVPS RFSGSGSGTEFTLTISSLQPDDFATYYCQQYNNYWTFGQGTKVEIKRTVAAPSVFIFPPS DEQLKSGTASVVCLLNNFYPREAKVqWKVDNALQSGNSQESVTEQDSKDSTYSLSSTLTL SKADYEKHKVYACEVTHQGLSSPVTKSFNRGEC |
| SEQ ID NO. 8 GK-5A1 HC amino acid sequence | QVQLVESGGGVVQPGRSLRLSCAASGFTFSSYGMYWVRQAPGKGLEWVAVIWNDGSNKYY ADSVKGRFTISRDNSKNTLYLQMNSLRAEDTAVYYCAREGSGWYDYYYGMDVWGQGTTVT VSSASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKKVEPKSCDKTHTCPPCPAPEL LGGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFFLYSKLTVDK SRWQQGNVFSCSVMHEALHNHYTQKSLSLSPGK |
| SEQ ID NO. 9 GK-5A1 LC amino acid sequence | EIVLTQSPSTLSASVGDRVTITCRASQSISSWLAWYQQKPGKAPKLLIYKASSLESGVPS RFSGSGSGTEFTLTISSLQPDDFATYYCQQYNSYWTFGQGTKVDIKRTVAAPSVFIFPPS DEQLKSGTASVVCLLNNFYPREAKVQWKVDNALQSGNSQESVTEQDSKDSTYSLSSTLTL SKADYEKHIKVYACEVTHQGLSSPVTKSFNRGEC |

TABLE 2-continued

Amino acid sequences of SEQ ID NO. 2-25 and 75-92, comprising variable
and constant domains, wherein the constant domain is underlined

| SEQ ID NO.<br>Name | Amino Acid Sequence (with constant domain underlined) |
|---|---|
| SEQ ID NO. 10<br>GK-2G8 HC<br>amino acid<br>sequence | QVQLQESGGGVVQPGRSLRLSCAASGFTFRSYGMHWVRQAPGKGLEWVAIIWYDGSKKYY<br>TDSVKGRFTISRDNSKNTLYLQMNSLRAEDTAVYYCARPGVAMTGLDLWGQGTLVTVSSA<br>STKGPSVFPLAPSSKSTSGGTAALGCLVKDYFPEPVTVSWNSGALTSGVHTPPAVLQSSG<br>LYSLSSVVTVPSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQ<br>QGNVFSCSVMHEALHNHYTQKSLSLSPGK |
| SEQ ID NO. 11<br>GK-2G8 LC<br>amino acid<br>sequence | EIVMTQSPSTLSASVGDRVTITCRASQSISSWLAWYQQKPGKAPKLLIYKASSLESGVPS<br>RPSGSGSGTEFTLTTSSLQPDDFATYYCQQYNNYWTFGQGTKVDIKRTVAAPSVFIFPPS<br>DEQLKSGTASVVCLLNNFYPREAKVQWKVDNALQSGNSQESVTEQDSKDSTYSLSSTLTL<br>SKADYEKHKVYACEVTHQGLSSPVTKSFNRGEC |
| SEQ ID NO. 12<br>GK-5E1 HC<br>amino acid<br>sequence | QVTLKESGGDVVQPGRSLRLSCAASGFTFRTYGMHWVRQAPGKGPEWVALIWYDGSKKYY<br>ADSVKGRFTISRDNSKNTLYLQMNSLRAEDTAVYYCVRVRFGELYFQHWGQGTLVTVSSA<br>STKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPTEKTISKAKGQPREPQVYTLPPSRDEL<br>TKNQVSLTCLVKGFYPSDIAVEWESNGQPENNYKTTPPVLDSDGSFFLYSKLTVDKSRWQ<br>QGNVFSCSVMHEALHNHYTQKSLSLSPGK |
| SEQ ID NO. 13<br>GK-5E1 LC<br>amino acid<br>sequence | DIVMTQSPSTLSASVGDRVTITCRASQSISSWLAWYQQKPGKAPKLLIYKASSLESGVPS<br>RFSGSGSGTEFTLTISSLQPDDFATYYCQQYNSYSYSFGQGTKLEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| SEQ ID NO. 14<br>GK-6B10 HC<br>amino acid<br>sequence | QVQLVESGGGVVQPGRSLRLSCAASGFTFSRYGMHWVRQAPGKGLEWVALIWYDGSNKYY<br>ADSVKGRFTISRDNSKNTLYLQMNSLRAEDTAVYYCARVAAALHFHYWGQGTLVTVSSAS<br>TKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKKVEPKSCDKTHTCPPCPAPELLGGPS<br>VFLFPPKPKDTLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLTVDKSRWQQ<br>GNVFSCSVMHEALHNHYTQKSLSLSPGK |
| SEQ ID NO. 15<br>GK-6B10 LC<br>amino acid<br>sequence | DIVMTQSPSTLSASVGDRVTITCRASQSIDNWLAWYQQKPGKAPKVLIYKASSLESGVPS<br>RFSGSGSGTEFTLTISSLQPDDFATYYCQQYNSYSYTFGQGTKLEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| SEQ ID NO. 16<br>GK-5G12 HC<br>amino acid<br>sequence | QITLKESGGGVVQPGRSLRLSCAASGFTFRTYGMHWVRQAPGKGLEWVALIWYDGSNKYY<br>ADSVKGRFTISRDNSKNTLYLQMNSLRAEDTAVYYCIRVKFGDLYFQHWGQGTLVTVSSA<br>STKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQ<br>QGNVFSCSVMHEALHNHYTQKSLSLSPGK |
| SEQ ID NO. 17<br>GK-5G12 LC<br>amino acid<br>sequence | EIVLTQSPSSLSASVGDRVTITCRASQGISNYLAWYQQKPGKVPKLLIYAASTLQSGVPS<br>RFSGSGSGTDFTLTISSLQPEDVATYYCQKYNSAPYTFGQGTKLEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| SEQ ID NO. 18<br>GK-21D3 HC<br>amino acid<br>sequence | QVQLVQSGGGVVQPGRSLRLSCAASGPTFSSYGMHWVRQAPGKGLEWVAIIWYDGSNKYY<br>ADSVKGRFTISRDNSKNTLYLQMNSLRDEDTAVYYCARMGAINRGGGGFDYWGQGTLVTV<br>SSASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLPPSR<br>DELTKNQVSLTCLVKGFYPSDIAVEWESNGQPENNYKTTPPVLDSDGSFFLYSKLTVDKS<br>RWQQGNVFSCSVMHEALHNHYTQKSLSLSPGK |
| SEQ ID NO. 19<br>GK-21D3 LC<br>amino acid<br>sequence | DIQLTQSPSSLSASIGDRVTITCRASQGISNYLAWYQQKPGKVPKLLIYAASTLQSGVPS<br>RFSGSGSGTDFTLTISSLQPEDVSTYYCQKYNSAPWTFGQGTKVDIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |

TABLE 2-continued

Amino acid sequences of SEQ ID NO. 2-25 and 75-92, comprising variable
and constant domains, wherein the constant domain is underlined

| SEQ ID NO.<br>Name | Amino Acid Sequence (with constant domain underlined) |
| --- | --- |
| SEQ ID NO. 20<br>MK-24C10 HC<br>amino acid<br>sequence | QVQLVESGGGVVQPGRSLRLSCAASGFTFSSYGMHWVRQAPGKGLEWVAVIWFDGTNKHY<br>ADSVKGRFTISRDNSKNTLYLQMNSLRAEDTAVYYCARDKGEWFGELRYYYYGMDVWGQG<br>TTVTVSSASTKGPSVFPLAPSSKSTSGGTAALGCLVKDYFPEPVTVSWNSGALTSGVHTF<br>PAVLQSSGLYSLSSVVTVPSSSLGTQTYICNVNHKPSNTKVDKKVEPKSCDKTHTCPPCP<br>APELLGGPSVFLFPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDSDGSFFLYSKL<br>TVDKSRWQQGNVFSCSVMHEALHNHYTQKSLSLSPGK |
| SEQ ID NO. 21<br>MK-24C10 LC<br>amino acid<br>sequence | EIVLTQSPLSLPVTPGEPASISCRSSQSLLHSNGYNYLDWYLQKPGQSPQLLIYLGSNRA<br>SGVPDRFSGSGSGTDFTLKISRVEAEDVGVYYCMQALQTPYTFGQGTKLEIKRTVAAPSV<br>FIFPPSDEQLKSGTASVVCLLNNFYPREAKVQWKVDNALQSGNSQESVTEQDSKDSTYSL<br>SSTLTLSKADYEKHKVYACEVTHQGLSSPVTKSFNRGEC |
| SEQ ID NO. 22<br>MK-24F9 HC<br>amino acid<br>sequence | EVQLQQWGAGLLKPSETLSLTCAVYGGSFSGYYWSWIRQPPGKGLEWIGDINHSRTTNYN<br>PSLKSRVTISVDTSKNQFSLKLSSVTAADTAVYYCARGGEQWLVPFDYWDQGTLVTVSSA<br>STKGPSVFPLAPSSKSTSGGTAALGCLVKDYFPEPVTVSWNSGALTSGVHTPPAVLQSSG<br>LYSLSSVVTVPSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQ<br>QGNVFSCSVMHEALHNHYTQKSLSLSPGK |
| SEQ ID NO. 23<br>MK-24F9 LC<br>amino acid<br>sequence | EIVMTQSPSTLSASVGDRVTITCRASQSISHWLAWYQQKPGKAPKLLIYKASSLKSGVPS<br>RFNGSGSGTEFTLTISSLQPDDFATYYCQHYNTYSRTFGQGTKVDIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| SEQ ID NO. 24<br>GK-22G12 HC<br>amino acid<br>sequence | EVQLVESGGGLVQSGGSLRLSCAASGFTFSSQRLSWVRQAPGKGLEWVANIKQDGSEKNY<br>VDSVRGRFTISRDIAKNSLYLQMNSLRAEDTAVYYCARDGYRNGWHIPEDYWGQGTLVTV<br>SSASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREEQ<br>YNSTYRVVSVLTVLHQDWLNGKEYKCKVSNKALPAPIEKTISKAKGQPREPQVYTLPPSR<br>DELTKNQVSLTCLVKGFYPSDIAVEWESNGQPENNYKTTPPVLDSDGSFFLYSKLTVDKS<br>RWQQGNVFSCSVMHEALHNHYTQKSLSLSPGK |
| SEQ ID NO. 25<br>GK-22G12 LC<br>amino acid<br>sequence | DIVMTQSPSSLSASVGDRVTITCRASQGISNYLAWYQQKPGKVPKLLIYAASTLQSGVPS<br>RFSGSGSGTDFTLTISSLQPEDVSTYYCQKHNRAPWTFGQGTKLEIKRTVAAPSVFIFPP<br>SDEQLKSGTASVVCLLNNFYPREAKVQWKVDNALQSGNSQESVTEQDSKDSTYSLSSTLT<br>LSKADYEKHKVYACEVTHQGLSSPVTKSFNRGEC |
| SEQ ID NO. 75<br>GK-1H2 HC<br>amino acid<br>sequence | EVQLLESGGGVVQPGRSLRLSCAASGFTFRSYGMHWVRQAPGKGLEWVAIIWYDGSKKYY<br>TDSVKGRFTISRDNSKNTLYLQMNSLRAEDTAVYYCARPGIAMTGLDYWGQGTLVTVSSA<br>STKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQ<br>QGNVFSCSVMHEALHNHYTQKSLSLSPGK |
| SEQ ID NO. 76<br>GK-1H2 LC<br>amino acid<br>sequence | EIVMTQSPSTLSASVGDRVTITCRASQSISSWLAWYQQKPGKAPKLLIYKASSLESGVPS<br>RFSGSGSGTEFTLTISSLQPDDFATYYCQQYNNYWTFGQGTKLEIKRTVAAPSVFIFPPS<br>DEQLKSGTASVVCLLNNFYPREAKVQWKVDNALQSGNSQESVTEQDSKDSTYSLSSTLTL<br>SKADYEKHKVYACEVTHQGLSSPVTKSFNRGEC |
| SEQ ID NO. 77<br>GK-2A9 HC<br>amino acid<br>sequence | QVQLVQSGGGVVQPGRSLRLSCAASGFTFRSYGMHWVRQAPGKGLEWVAIIWYDGSKKYY<br>TDSVKGRFTISRDNSKNTLYLQMNSLRAEDTAVYYCARPGVAMTGLDLWGQGTLVTVSSA<br>STKGPSVFPLAPSSKSTSGGTAALGCLVKDYFPEPVTVSWNSGALTSGVHTFPAVLQSSG<br>LYSLSSVVTVPSSSLGTQTYICNVNHKPSNTKVDKKVEPKSCDKTHTCPPCPAPELLGGP<br>SVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKLTVDKSRWQ<br>QGNVFSCSVMHEALHNHYTQKSLSLSPGK |
| SEQ ID NO. 78<br>GK-2A9 LC<br>amino acid<br>sequence | EIVLTQSPSTLSASVGDRVTITCRASQSISSWLAWYQQKPGKAPKLLIYKASSLESGVPS<br>RFSGSGSGTEFTLTISSLQPDDFATYYCQQYNNYWTFGQGTKVDIKRTVAAPSVFIFPPS<br>DEQLKSGTASVVCLLNNFYPREAKVQWKVDNALQSGNSQESVTEQDSKDSTYSLSSTLTL<br>SKADYEKHIKVYACEVTHQGLSSPVTKSFNRGEC |

TABLE 2-continued

Amino acid sequences of SEQ ID NO. 2-25 and 75-92, comprising variable
and constant domains, wherein the constant domain is underlined

| SEQ ID NO. Name | Amino Acid Sequence (with constant domain underlined) |
| --- | --- |
| SEQ ID NO. 79 GK-5A6 HC amino acid sequence | EVQLQESGGGVVQPGRSLRLSCAASGFTFRTYGMHWVRQAPGKGLEWVALIWYDGSNKYY ADSVKGRFTISRDNSKNTLYLQMNSLRAEDTAVYYCIRVKFGDLYFQHWGQGTLVTVSSA <u>STKGPSVFPLAPSSKSTSGGTAALGCLVKDYFPEPVTVSWNSGALTSGVHTPPPAVLQSSG LYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQ QGNVFSCSVMHEALHNHYTQKSLSLSPGK</u> |
| SEQ ID NO. 80 GK-5A6 LC aminoa cid sequence | DVVMTQSPSTLSASVGDRVTITCRASQSISSWLAWYQQKPGKAPKLLIYKASSLESGVPS RFSGSGSGTEFTLTTSSLQPDDFATYYCQQYNSYSYTFGQGTKLEIKRTVAAPSVFIFPP <u>SDEQLKSGTASVVCLLNNFYPREAKVQWKVDNALQSGNSQESVTEQDSKDSTYSLSSTLT LSKADYEKHKVYACEVTHQGLSSPVTKSFNRGEC</u> |
| SEQ ID NO. 81 GK-21F1 HC amino acid sequence | QVQLVQSGGGVVQPGRSLRLSCAASGFTFSSYGMHWVRQAPGKGLEWVAIIWYDGSNKYY ADSVKGRFTISRDNSKNTLYLQMNSLRDEDTAVYYCARMGAINRGGGGFDYWGQGTLVTV <u>SSASTKGPSVFPLAPSSKSTSGGTAALGCLVKDYFPEPVTVSWNSGALTSGVHTFPAVLQ SSGLYSLSSVVTVPSSSLGTQTYICNVNHKPSNTKVDKKVEPKSCDKTHTCPPCPAPELL GGPSVFLFPPKPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFLYSKLTVDKS RWQQGNVFSCSVMHEALHNHYTQKSLSLSPGK</u> |
| SEQ ID NO. 82 GK-21F1 LC amino acid sequence | DIQLTQSPSSLSASIGDRVTITCRASQGISNYLAWYQQKPGKVPKLLIYAASTLQSGVPS RFSGSGSGTDFTLTISSLQPEDVSTYYCQKYNSAPWTFGQGTKVDIKRTVAAPSVFIFPP <u>SDEQLKSGTASVVCLLNNFYPREAKVQWKVDNALQSGNSQESVTEQDSKDSTYSLSSTLT LSKADYEKHKVYACEVTHQGLSSPVTKSFNRGEC</u> |
| SEQ ID NO. 83 MK-24C12 HC amino acid sequence | EVQLVESGGGVVQPGRSLRLSCAASGFTFSSYGMHWVRQAPGKGLEWVAVIWFDGTNKHY ADSVKGRFTISRDNSKNTLYLQMNSLRAEDTAVYYCARDKGEWFGELRYYYYGMDVWGQG TTVTVSSA<u>STKGPSVFPLAPSSKSTSGGTAALGCLVKDYFPEPVTVSWNSGALTSGVHTF PAVLQSSGLYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKL TVDKSRWQQGNVFSCSVMHEALHNHYTQKSLSLSPGK</u> |
| SEQ ID NO. 84 MK-24C12 LC amino acid sequence | EIVLTQSPLSLPVTPGEPASISCRSSQSLLHSNGYNYLDWYLQKPGQSPQLLIYLGSNRA SGVPDRFSGSGSGTDFTLKISRVEAEDVGVYYCMQALQTPYTFGQGTKLEIKRTVAAPSV <u>FIFPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC</u> |
| SEQ ID NO. 85 GK-21G5 HC amino acid sequence | QVQLQQWGAGLLKPSETLSLTCAVYGGSFSGYYWSWIRQPPGKGLEWIGEINHSGITNYN PSLKSRLTVSVDTSKNQFSLKLSSVTAADTAVYYCARGGDQWLVPFDNWGQGTLVTVSSA <u>STKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQ QGNVFSCSVMHEALHNHYTQKSLSLSPGK</u> |
| SEQ ID NO. 86 GK-21G5 LC amino acid sequence | DIVMTQSPSSLSASVGDRVTITCRASQGISNYLAWYQQKPGKVPKLLIYAASTLQSGVPS RFSGSGSGTDFTLTISSLQPEDVSTYYCQKHNRAPWTFGQGTKLEIKRTVAAPSVFIFPP <u>SDEQLKSGTASVVCLLNNFYPREAKVQWKVDNALQSGNSQESVTEQDSKDSTYSLSSTLT LSKADYEKHKVYACEVTHQGLSSPVTKSFNRGEC</u> |
| SEQ ID NO. 87 GK-23A8 HC amino acid sequence | QVQLQQWGAGLLKPSETLSLTCAVYGGSFSGYYWSWIRQPPGKGLEWIGEINHSGITNYN PSLKSRLTVSVDTSKNQPSLKLSSVTAADTAVYYCARGGDQWLVPFDNWGQGTLVTVSSA <u>STKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKLTVDKSRWQ QGNVFSCSVMHEALHNHYTQKSLSLSPGK</u> |
| SEQ ID NO. 88 GK-23A8 LC amino acid sequence | ETVMTQSPSTLSASVGDRVTITCRASQSISHWLAWYQQKPGKAPKLLIYKASSLKSGVPS RFNGSGSGTEFTLTISSLQPDDFATYYCQHYNTYSRTFGQGTKVDIKRTVAAPSVFIFPP <u>SDEQLKSGTASVVCLLNNFYPREAKVQWKVDNALQSGNSQESVTEQDSKDSTYSLSSTLT LSKADYEKHKVYACEVTHQGLSSPVTKSFNRGEC</u> |
| SEQ ID NO. 89 GK-21E6 HC amino acid sequence | RVQLVQSGGGLVQSGGSLRLSCAASGFTFSSQRLSWVRQAPGKGLEWVANIKQDGSEKNY VDSVRGRFTISRDIAKNSLYLQMNSLRAEDTAVYYCARDGYRNGWHIPEDYWGQGTLVTV <u>SSASTKGPSVFPLAPSSKSTSGGTAALGCLVKDYFPEPVTVSWNSGALTSGVHTFPAVLQ SSGLYSLSSVVTVPSSSLGTQTYICNVNHKPSNTKVDKKVEPKSCDKTHTCPPCPAPELL</u> |

TABLE 2-continued

Amino acid sequences of SEQ ID NO. 2-25 and 75-92, comprising variable
and constant domains, wherein the constant domain is underlined

| SEQ ID NO. Name | Amino Acid Sequence (with constant domain underlined) |
|---|---|
| | GGPSVFLFPPKPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFLYSKLTVDKS RWQQGNVFSCSVMHEALHNHYTQKSLSLSPGK |
| SEQ ID NO. 90 GK-21E6 LC amino acid sequence | DVVMTQSPSSLSASVGDRVTITCRASQGISNYLAWYQQKPGKVPKLLIYAASTLQSGVPS RFSGSGSGTDFTLTISSLQPEDVSTYYCQKHNRAPWTFGQGTKLEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |
| SEQ ID NO. 91 GK-22E12 HC amino acid sequence | EVQLLESGGGLVQSGGSLRLSCAASGPTFSSQRLSWVRQAPGKGLEWVANIKQDGSEKNY VDSVRGRFTISRDIAKNSLYLQMNSLRAEDTAVYYCARDGYRNGWHIPEDYWGQGTLVTV SSASTKGPSVFPLAPSSKSTSGGTAALGCLVKDYPPEPVTVSWNSGALTSGVHTFPAVLQ SSGLYSLSSVVTVPSSSLGTQTYICNVNHKPSNTKVDKKVEPKSCDKTHTCPPCPAPELL GGPSVFLFPPKPKDTLMISRTPEVTCVVVDVSHEDPEVKFNWYVDGVEVHNAKTKPREEQ YNSTYRVVSVLTVLHQDWLNGKEYKCKVSNKALPAPIEKTTSKAKGQPREPQVYTLPPSR DELTKNQVSLTCLVKGFYPSDIAVEWESNGQPENNYKTTPPVLDSDGSFFLYSKLTVDKS RWQQGNVFSCSVMHEALHNHYTQKSLSLSPGK |
| SEQ ID NO. 92 GK-22E12 LC amino acid sequence | AIRMTQSPSSLSASVGDRVTITCRASQGISNYLAWYQQKPGKVPKLLIYAASTLQSGVPS RFSGSGSGTDFTLTISSLQPEDVSTYYCQKHNRAPWTFGQGTKVEIKRTVAAPSVFIFPP SDEQLKSGTASVVCLLNNFYPREAKVQWKVDNALQSGNSQESVTEQDSKDSTYSLSSTLT LSKADYEKHKVYACEVTHQGLSSPVTKSFNRGEC |

Assays for assessing binding competition include, but are not limited to, radioactive material labeled immunoassays (RIA), enzyme-linked immunosorbent assays (ELISA), sandwich ELISA assays, fluorescence activated cell sorting (FACS) assays and Biacore (SPR) assays. In conducting an antibody competition assay between a control antibody and a test antibody, one may first label the reference with a detectable label, such as a fluorophore, biotin or an enzymatic (or even radioactive) label to enable subsequent identification. If the test antibody competes with the labeled control antibody, the intensity will be decreased relative to a control reaction carried out without test antibody.

Methods for determining binding epitope include, but are not limited to, assessment of binding to an array of oligopeptides having (overlapping) amino acid sequences from the ROR2 sequence, resolution of a crystal or NMR structure of the antibody, antibody-based binding protein or antigen-binding fragment thereof with ROR2, by assessment of binding loss of antibodies, antibody-based binding proteins, antigen-binding fragments thereof to ROR2 comprising one or more amino acid mutations ("high throughput mutagenesis") and by hydrogen-deuterium exchange to assess the solvent accessible surface of the ROR2 complex with the antibody, antibody-based binding protein or antigen-binding fragment (Abbott M. et al. 2014).

In a preferred embodiment, fully human anti-ROR2 antibodies, antibody-based binding proteins, antigen-binding fragments thereof, AECs, ADCs, or CARs having the same binding specificity for ROR2 (and especially for hROR2 comprising or consisting of SEQ ID NO. 1), i.e., binding to the same ROR2 epitope and/or competing for ROR2 binding, as ROR2 specific antibodies containing an immunoglobulin heavy chain variable region (Ig HCVR) sequence and an immunoglobulin light chain variable region (Ig LCVR) sequence, respectively, shown in: (i) SEQ ID NO:2 and SEQ ID NO:3; (ii) SEQ ID NO:6 and SEQ ID NO:7; (iii) SEQ ID NO:10 and SEQ ID NO:11; (iv) SEQ ID NO:12 and SEQ ID NO:13; (v) SEQ ID NO:14 and SEQ ID NO:15; (vi) SEQ ID NO:16 and SEQ ID NO:17; (vii) SEQ ID NO:4 and SEQ ID NO:5; (viii) SEQ ID NO:8 and SEQ ID NO:9; (ix) SEQ ID NO:18 and SEQ ID NO:19; (x) SEQ ID NO:24 and SEQ ID NO:25: (xi) SEQ ID NO:20 and SEQ ID NO:21; and (xii) SEQ ID NO:22 and SEQ ID NO:23, and more preferably as shown in (i) SEQ ID NO:2 and SEQ ID NO:3; (ii) SEQ ID NO:8 and SEQ ID NO:9; and (iii) SEQ ID NO:20 and SEQ ID NO:21.

| Type | Ig HCVR | Ig LCVR |
|---|---|---|
| MK-3B12 | SEQ ID NO: 2 | SEQ ID NO: 3 |
| GK-1E5 | SEQ ID NO: 6 | SEQ ID NO: 7 |
| GK-2G8 | SEQ ID NO: 10 | SEQ ID NO: 11 |
| GK-5E1 | SEQ ID NO: 12 | SEQ ID NO: 13 |
| GK-6B10 | SEQ ID NO: 14 | SEQ ID NO: 15 |
| GK-5G12 | SEQ ID NO: 16 | SEQ ID NO: 17 |
| MK-7C3 | SEQ ID NO: 4 | SEQ ID NO: 5 |
| GK-5A1 | SEQ ID NO: 8 | SEQ ID NO: 9 |
| MK-21D3 | SEQ ID NO: 18 | SEQ ID NO: 19 |
| GK-22G12 | SEQ ID NO: 24 | SEQ ID NO: 25 |
| MK-24C10 | SEQ ID NO: 20 | SEQ ID NO: 21 |
| MK-24F9 | SEQ ID NO: 22 | SEQ ID NO: 23 |

In various embodiments, an antibody, antibody-based binding protein, antigen-binding fragment thereof, AEC, ADC or CAR is considered to compete with a control antibody if it decreases binding of the control antibody by at least about 20% or more, for example, by at least about 20%, 30%, 40%, 50%, 60%, 70%, 80%, 90%, 95% or even more, or by a percentage ranging between any of the foregoing values, at a control antibody concentration that is 80% of maximal binding under the specific assay conditions used, and a test antibody or antigen-binding fragment concentration that is 10-fold higher than the control antibody concentration.

Preferred Embodiments Relative to the Foregoing Invention Aspects

In any of the foregoing aspects of the invention, the fully human anti-ROR2 antibody, antibody-based binding protein, antigen-binding fragment thereof, AEC, ADC or CAR preferably binds to ROR2 comprising or consisting of SEQ ID NO. 1 with a $K_d$ of less than 100 nM, more preferably of less than 75 nM, even more preferably of less than 50 nM and most preferably of less than 25 nM.

In any of the foregoing aspects of the invention, the fully human anti-ROR2 antibody, antibody-based binding protein, antigen-binding fragment thereof, AEC, ADC or CAR preferably binds to ROR2 comprising or consisting of SEQ ID NO. 1 with a $k_{on}$ of greater than $1 \times 10^4$ M$^{-1}$ s$^{-1}$, more preferably of greater than $1 \times 10^5$ M$^{-1}$ s$^{-1}$, even more preferably of greater than $1 \times 10^6$ M$^{-1}$ s$^{-1}$.

In any of the foregoing aspects of the invention, the fully human anti-ROR2 antibody, antibody-based binding protein, antigen-binding fragment thereof, AEC, ADC or CAR preferably binds to ROR2 comprising or consisting of SEQ ID NO. 1 with a $k_{off}$ of less than $1 \times 10^{-2}$ s$^{-1}$, more preferably of less than $1 \times 10^{-3}$ s$^{-1}$, and even more preferably of less than $1 \times 10^{-4}$ s$^{-1}$.

Binding affinity is generally expressed in terms of equilibrium association or dissociation constants ($K_a$ or $K_d$, respectively), which are in turn reciprocal ratios of dissociation and association rate constants ($k_{off}$ and $k_{on}$, respectively). Thus, equivalent affinities may correspond to different rate constants, so long as the ratio of the rate constants remains the same. Binding affinities and/or rate constants can be determined using techniques well known in the art or described herein, such as, for example, ELISA, isothermal titration calorimetry (ITC), Biacore (SPR), biolayer inferometry or fluorescent polarization.

The invention also relates to fully human anti-ROR2 antibodies, antibody-based binding proteins, antigen-binding fragments thereof, ADCs, AECs or CARs comprising a $V_H$ chain comprising three CDRs wherein:

$V_H$ CDR no. 1 comprises or consists of peptide sequence GYSISSGYY (SEQ ID NO. 26) or $GX_1X_2FX_3X_4X_5X_6$ (SEQ ID NO. 67) where $X_1$=F or G, $X_2$=T or S, $X_3$=R or S, $X_4$=S, T, R or G, $X_5$=H, Y or Q, $X_6$=G, Y or R; and/or $V_H$ CDR no. 2 comprises or consists of peptide sequence IYQSGST (SEQ ID NO. 27), INHSRTT (SEQ ID NO. 59), INHSGIT (SEQ ID NO. 93), or $IX_7X_8DGX_9X_{10}K$ (SEQ ID NO. 68), where $X_7$=W or K, $X_8$=Y, N, F or Q, $X_9$=S or T, $X_{10}$=K, N or E; and/or $V_H$ CDR no. 3 comprises or consists of a peptide sequence selected from:

CAREDRAGWYPFDCW, (SEQ ID NO. 28)

CARVGAGLYLDYW, (SEQ ID NO. 33)

CAREGSGWYDYYYGMDVW, (SEQ ID NO. 40)

CQHYNTYSRTF, (SEQ ID NO. 62)

CARPGIAMTGLDYW, (SEQ ID NO. 37)

CARGGDQWLVPFDNW, (SEQ ID NO. 95)

CARVAAALHFHYW, (SEQ ID NO. 47)

CARGGEQWLVPFDYW, (SEQ ID NO. 60)

CARPGVAMTGLDLW, (SEQ ID NO. 43)

CIRVKFGDLYFQHW, (SEQ ID NO. 49)

CVRVRFGELYFQHW, (SEQ ID NO. 44)

CARDGYRNGWHIPEDYW, (SEQ ID NO. 65)

CARMGAINRGGGGFDYW (SEQ ID NO. 52)
and

CARDKGEWFGELRYYYYGMDVW. (SEQ ID NO. 55)

The invention also relates to fully human anti-ROR2 antibodies, antibody-based binding proteins, antigen-binding fragments thereof, ADCs, AECs or CARs comprising a $V_H$ chain comprising three CDRs wherein:

$V_H$ CDR no. 1 comprises or consists of peptide sequence GYSISSGYY (SEQ ID NO. 26) or $GX_1X_2FX_3X_4X_5X_6$ (SEQ ID NO. 67) where $X_1$=F or G, $X_2$=T or S, $X_3$=R or S, $X_4$=S, T, R or G, $X_5$=H, Y or Q, $X_6$=G, Y or R; and $V_H$ CDR no. 2 comprises or consists of peptide sequence IYQSGST (SEQ ID NO. 27), INHSRTT (SEQ ID NO. 59), or $IX_7X_8DGX_9X_{10}K$ (SEQ ID NO. 68), where $X_7$=W or K, $X_8$=Y, N, F or Q, $X_9$=S or T, $X_{10}$=K, N or E; and $V_H$ CDR no. 3 comprises or consists of a peptide sequence selected from:

CAREDRAGWYPFDCW, (SEQ ID NO. 28)

CARVGAGLYLDYW, (SEQ ID NO. 33)

CAREGSGWYDYYYGMDVW, (SEQ ID NO. 40)

CQHYNTYSRTF, (SEQ ID NO. 62)

CARPGIAMTGLDYW, (SEQ ID NO. 37)

CARGGDQWLVPFDNW, (SEQ ID NO. 95)

CARVAAALHFHYW, (SEQ ID NO. 47)

CARGGEQWLVPFDYW, (SEQ ID NO. 60)

CARPGVAMTGLDLW, (SEQ ID NO. 43)

CIRVKFGDLYFQHW, (SEQ ID NO. 49)

CVRVRFGELYFQHW, (SEQ ID NO. 44)

```
                                         (SEQ ID NO. 65)
CARDGYRNGWHIPEDYW, (SEQ ID NO. 52)
CARMGAINRGGGFDYW
and (SEQ ID NO. 55)
CARDKGEWFGELRYYYYGMDVW.
```

The invention also relates to fully human anti-ROR2 antibodies, antibody-based binding proteins, antigen-binding fragments thereof, ADCs, AECs or CARs comprising a $V_H$ chain comprising three CDRs wherein:

- $V_H$ CDR no. 1 comprises or consists of peptide sequence GYSISSGYY (SEQ ID NO. 26), GFTFRSHG (SEQ ID NO. 31), GGSFSGYY (SEQ ID NO. 58), GFTFSSQR (SEQ ID NO. 63), or GFTFX$_3$X$_4$YG (SEQ ID NO. 71) where X$_3$=R or S, and X$_4$=S, T or R, and preferably comprises or consists of peptide sequence GYSISSGYY (SEQ ID NO. 26), GFTFRSYG (SEQ ID NO 36), GFTFRTYG (SEQ ID NO 94), GFTFSRYG (SEQ ID NO 45), GFTFRSHG (SEQ ID NO. 31), GFTFSSYG (SEQ ID NO. 38). GGSFSGYY (SEQ ID NO. 58) or GFTFSSQR (SEQ ID NO. 63), and more preferably comprises or consists of peptide sequence GYSISSGYY (SEQ ID NO. 26) or GFTFSSYG (SEQ ID NO. 38); and
- $V_H$ CDR no. 2 comprises or consists of peptide sequence IYQSGST (SEQ ID NO. 27), IWYDGSKK (SEQ ID NO 32), IWYDGSNK (SEQ ID NO 46), IWNDGSNK (SEQ ID NO. 39), IWFDGTNK (SEQ ID NO. 54), INHSRTT (SEQ ID NO. 59) or IKQDGSEK (SEQ ID NO. 64), and preferably comprises or consists of peptide sequence IYQSGST (SEQ ID NO. 27), IWNDGSNK (SEQ ID NO. 39), or IWFDGTNK (SEQ ID NO. 54); and
- $V_H$ CDR no. 3 comprises or consists of a peptide sequence selected from: CAREDRAGWYPFDCW (SEQ ID NO. 28), CARPGIAMTGLDYW, CARPGVAMTGLDLW (DEQ ID NO. 43), CVRVRFGELYFQHW (SEQ ID NO. 44), CARVAAALHFHYW (SEQ ID NO. 47), CIRVKFGDLYFQHW (SEQ ID NO. 49), CARVGAGLYLDYW (SEQ ID NO. 33), CARPGIAMTGLDYW (SEQ ID NO. 37), CAREGSGWYDYYYGMDVW (SEQ ID NO. 40), CARDKGEWFGELRYYYYGMDVW (SEQ ID NO. 55), CARGGEQWLVPFDYW (SEQ ID NO. 60) or CARDGYRNGWHIPEDYW (SEQ ID NO. 65), and preferably comprises or consists of a peptide sequence selected from: CAREDRAGWYPFDCW (SEQ ID NO. 28), CAREGSGWYDYYYGMDVW (SEQ ID NO. 40) or CARDKGEWFGELRYYYYGMDVW (SEQ ID NO. 55).

In any of the foregoing aspect of the invention, the anti-ROR2 antibodies, antibody-based binding proteins, antigen-binding fragments thereof. ADCs, AECs or CARs comprising a $V_H$ chain comprising three CDRs wherein:

- $V_H$ CDR no. 1 comprises or consists of a peptide sequence selected from HC CDR1 sequences listed in Table 3: and/or
- $V_H$ CDR no. 2 comprises or consists of a peptide sequence selected from HC CDR2 sequences listed in Table 3: and/or
- $V_H$ CDR no. 3 comprises or consists of a peptide sequence selected from HC CDR3 sequences listed in Table 3.

In any of the foregoing aspect of the invention, the anti-ROR2 antibodies, antibody-based binding proteins, antigen-binding fragments thereof, ADCs, AECs or CARs comprising a $V_H$ chain comprising three CDRs wherein:

- $V_H$ CDR no. 1 comprises or consists of a peptide sequence selected from HC CDR1 sequences listed in Table 3; and
- $V_H$ CDR no. 2 comprises or consists of a peptide sequence selected from HC CDR2 sequences listed in Table 3; and
- $V_H$ CDR no. 3 comprises or consists of a peptide sequence selected from HC CDR3 sequences listed in Table 3.

In any of the foregoing aspect of the invention, the anti-ROR2 antibodies, antibody-based binding proteins, antigen-binding fragments thereof, ADCs, AECs or CARs comprising a $V_H$ chain comprise three CDRs wherein $V_H$ CDR no. 1, $V_H$ CDR no. 2 and $V_H$ CDR no. 3 comprises or consists of a peptide sequence according to a given HC CDR1, CDR2 and CDR3 triplet listed in Table 3.

In any of the foregoing aspect of the invention, the anti-ROR2 antibodies, antibody-based binding proteins, antigen-binding fragments thereof, ADCs, AECs or CARs comprising a $V_H$ chain comprise three CDRs wherein $V_H$ CDR no. 1, $V_H$ CDR no. 2 and $V_H$ CDR no. 3 comprises or consists of a peptide sequence according to the HC CDR1, CDR2 and CDR3 triplet of MK-3B12, GK-5A1, GK-21D3, MK-24C10, MK-24F9 or GK-22G12, and more preferably of MK-3B12, GK-5A1 or MK-24C10 listed in Table 3.

The invention further relates to anti-ROR2 antibodies, antibody-based binding proteins, antigen-binding fragments thereof. ADCs, AECs or CARs comprising a $V_L$ chain comprising three CDRs wherein:

- $V_L$ CDR no. 1 comprises or consists of peptide sequence QSLLHSNGYNY (SEQ ID NO. 56), QSIDNW (SEQ ID NO. 48), or QX$_{11}$ISX$_{12}$X$_{13}$ (SEQ ID NO. 69) where X$_{11}$=S, T or G, X$_{12}$=S, N or H and X$_{13}$=W or Y; and/or
- $V_L$ CDR no. 2 comprises or consists of peptide sequence KAS. AAS or LGS; and/or
- $V_L$ CDR no. 3 comprises or consists of a peptide sequence CX$_{14}$X$_{15}$X$_{16}$X$_{17}$X$_{18}$X$_{19}$X$_{20}$X$_{21}$X$_{22}$F (SEQ ID NO. 70) where X$_{14}$=Q or M, X$_{15}$=K, H or Q, X$_{16}$=H, Y or A, X$_{17}$=N or L, X$_{18}$=R, T, Q, S or N; X$_{19}$=A, Y or T; X$_{20}$=P, S or W, X$_{21}$=W, R, Y or absent, X$_{22}$=S or T.

The invention further relates to anti-ROR2 antibodies, antibody-based binding proteins, antigen-binding fragments thereof, ADCs, AECs or CARs comprising a $V_L$ chain comprising three CDRs wherein:

- $V_L$ CDR no. 1 comprises or consists of peptide sequence QSLLHSNGYNY (SEQ ID NO. 56), QSIDNW (SEQ ID NO. 48), or QX$_{11}$ISX$_{12}$X$_{13}$ (SEQ ID NO. 69) where X$_{11}$=S, T or G, X$_{12}$=S, N or H and X$_{13}$=W or Y; and
- $V_L$ CDR no. 2 comprises or consists of peptide sequence KAS. AAS or LGS; and
- $V_L$ CDR no. 3 comprises or consists of a peptide sequence CX$_{14}$X$_{15}$X$_{16}$X$_{17}$X$_{18}$X$_{19}$X$_{20}$X$_{21}$X$_{22}$F (SEQ ID NO. 70) where X$_{14}$=Q or M, X$_{15}$=K, H or Q, X$_{16}$=H, Y or A, X$_{17}$=N or L, X$_{18}$=R, T, Q, S or N; X$_{19}$=A, Y or T; X$_{20}$=P, S or W, X$_{21}$=W, R, Y or absent, X$_{22}$=S or T.

The invention further relates to anti-ROR2 antibodies, antibody-based binding proteins, antigen-binding fragments thereof, ADCs, AECs or CARs comprising a $V_L$ chain comprising three CDRs wherein:

- $V_L$ CDR no. 1 comprises or consists of peptide sequence QSISSW (SEQ ID NO. 29), QTISNW (SEQ ID NO. 34), QSIDNW (SEQ ID NO. 48), QGISNY (SEQ ID NO. 50), QSLLHSNGYNY (SEQ ID NO. 56) or QSISHW (SEQ ID NO. 61), and preferably comprises or consists of peptide sequence QSISSW (SEQ ID NO. 29), or QSLLHSNGYNY (SEQ ID NO. 56); and $V_L$ CDR no. 2 comprises or consists of peptide sequence KAS, LGS or AAS, and preferably comprises or consists of peptide sequence KAS or LGS; and $V_L$ CDR no. 3 comprises or consists of a peptide sequence CQQYNNYWTF (SEQ ID NO. 30), CQQYNSYWTF (SEQ ID NO. 41), CQQYNSYSYSF (SEQ ID NO. 42), CQQYNSYSYSF (SEQ ID NO. 44), CQQYNSYS-YTF (SEQ ID NO. 35), CQKYNSAPYTF (SEQ ID NO. 51), CARMGAINRGGGGFDYW (SEQ ID NO. 52), CQKYNSAPWTF (SEQ ID NO. 53), CMQALQTPYTF (SEQ ID NO. 57), CQHYN-TYSRTF (SEQ ID NO. 62) or CQKHNRAPWTF (SEQ ID NO. 66), and preferably comprises or consists of a peptide sequence CQQYNNYWTF (SEQ ID NO. 30), CQQYNSYWTF (SEQ ID NO. 41) or CMQALQTPYTF (SEQ ID NO. 57).

In any of the foregoing aspect of the invention, the fully human anti-ROR2 antibodies, antibody-based binding proteins, antigen-binding fragments thereof, ADCs, AECs or CARs comprising a $V_L$ chain comprising three CDRs wherein:

$V_L$ CDR no. 1 comprises or consists of a peptide sequence selected from LC CDR1 sequences listed in Table 3: and/or $V_L$ CDR no. 2 comprises or consists of a peptide sequence selected from LC CDR2 sequences listed in Table 3; and/or $V_L$ CDR no. 3 comprises or consists of a peptide sequence selected from LC CDR3 sequences listed in Table 3.

In any of the foregoing aspect of the invention, the fully human anti-ROR2 antibodies, antibody-based binding proteins, antigen-binding fragments thereof, ADCs, AECs or CARs comprising a $V_L$ chain comprising three CDRs wherein:

$V_L$ CDR no. 1 comprises or consists of a peptide sequence selected from LC CDR1 sequences listed in Table 3; and $V_L$ CDR no. 2 comprises or consists of a peptide sequence selected from LC CDR2 sequences listed in Table 3: and $V_L$ CDR no. 3 comprises or consists of a peptide sequence selected from LC CDR3 sequences listed in Table 3.

In any of the foregoing aspect of the invention, the fully human anti-ROR2 antibodies, antibody-based binding proteins, antigen-binding fragments thereof, ADCs, AECs or CARs comprising a $V_L$ chain comprise three CDRs wherein $V_L$ CDR no. 1, $V_L$ CDR no. 2 and $V_L$ CDR no. 3 comprises or consists of a peptide sequence according to a given LC CDR1, CDR2 and CDR3 triplet listed in Table 3.

In any of the foregoing aspect of the invention, the anti-ROR2 antibodies, antibody-based binding proteins, antigen-binding fragments thereof, ADCs, AECs or CARs comprising a $V_L$ chain comprise three CDRs wherein $V_L$ CDR no. 1, $V_L$ CDR no. 2 and $V_L$ CDR no. 3 comprises or consists of a peptide sequence according to the LC CDR1, CDR2 and CDR3 triplet of MK-3B12, GK-5A1, GK-21D3, MK-24C10, MK-24F9 or GK-22G12, and more preferably of MK-3B12, GK-5A1 or MK-24C10 listed in Table 3.

In any of the foregoing aspect of the invention, the anti-ROR2 antibodies, antibody-based binding proteins, antigen-binding fragments thereof, ADCs, AECs or CARs comprise a VL and $V_H$ chain each comprising three CDRs comprising or consisting of, as per Table 3, the peptide sequence of the respective CDRs of: MK-3B12, MK-7C3, GK-1E5, GK-5E1, GK-2G8, GK-5A1, GK-6B10, GK-5G12, GK-21D3, MK-24C10. MK-24F9 or GK-22G12, and preferably of: MK-3B12, GK-5A1, GK-21D3, MK-24C10, MK-24F9 or GK-22G12, and more preferably of: MK-3B12, GK-5A1 or MK-24C10.

In any of the foregoing aspect of the invention, the anti-ROR2 antibodies, antibody-based binding proteins, antigen-binding fragments thereof, ADCs, AECs or CARs comprise a $V_L$ and $V_H$ chain each comprising three CDRs comprising or consisting of, as per Table 3, the peptide sequence of the respective CDRs of: MK-3B12, GK-1E5, GK-2G8, GK-5E1, GK-6B10 or GK-5G12, or of; GK-5A1, GK-21D3, MK-24C10, MK-24F9, MK-7C3 or GK-22G12, or more preferably of MK-3B12, GK-5A1, GK-21D3, MK-24C10, MK-24F9 or GK-22G12, or even more preferably of: MK-3B12, GK-5A1 or MK-24C10.

In one embodiment, the antibody, antibody-based binding protein, modified antibody format retaining target binding capacity, antibody derivative or fragment retaining target binding capacity has cross-reactivity to (i) human ROR2 (hROR2) and (ii) at least one of cynomolgus ROR2 (cROR2) and murine RoR2 (mROR2).

As used herein, the term "cross-reactivity" means that the antibody, antibody-based binding protein, modified antibody format retaining target binding capacity, antibody derivative or fragment retaining target binding is capable to bind to (i) human ROR2 (hROR2) and (ii) at least one of cynomolgus ROR2 (cROR2) and murine RoR2 (mROR2), with sufficient affinity.

Said cross-reactivity has significant advantages in preclinical applications, because the same antibody that has been used for studies in mice and cynomolgous monkeys can later be used for clinical approval. Further, said cross-reactivity has significant advantages in diagnostic as well as scientific applications.

In one embodiment, the antibody, antibody-based binding protein, modified antibody format retaining target binding capacity, antibody derivative or fragment retaining target binding capacity comprises one of the following CDR sets:

a) heavy chain CDRs 1-3 as set forth in SEQ ID NOs 38, 39 and 40, and light chain CDRs 1 and 3 as set forth in SEQ ID NOs 29 and 41, with light chain CDR 2 having the sequence KAS b) heavy chain CDRs 1-3 as set forth in SEQ ID NOs 26-28, and light chain CDRs 1-3 as set forth in SEQ ID NOs 29, 30 and 73, c) heavy chain CDRs 1-3 as set forth in SEQ ID NOs 94, 32 and 44, and light chain CDRs 1 and 3 as set forth in SEQ ID NOs 29 and 42, with light chain CDR 2 having the sequence KAS d) heavy chain CDRs 1-3 as set forth in SEQ ID NOs 38, 46 and 52, and light chain CDRs 1 and 3 as set forth in SEQ ID NOs 50 and 53, with light chain CDR 2 having the sequence AAS e) heavy chain CDRs 1-3 as set forth in SEQ ID NOs 38, 54 and 55, and light chain CDRs 1 and 3 as set forth in SEQ ID NOs 56 and 57, with light chain CDR 2 having the sequence LGS, f) heavy chain CDRs 1-3 as set forth in SEQ ID NOs 58-60, and light chain CDRs 1 and 3 as set forth in SEQ ID NOs 61, and 62, with light chain CDR 2 having the sequence KAS, g) heavy chain CDRs 1-3 as set forth in SEQ ID NOs 63-65 with light chain CDRs 1 and 3 as set forth in SEQ ID NOs 50 and 66, with light chain CDR 2 having the sequence AAS, The CDRs are comprised in a suitable protein framework so as to be capable to bind to hROR2 as well as to at least one of cynomolgus ROR2 (cROR2) and murine RoR2 (mROR2), with sufficient affinity.

In one embodiment, the antibody, antibody-based binding protein, modified antibody format retaining target binding capacity, antibody derivative or fragment retaining target binding capacity comprises one of the following sequence pairs:

a) the heavy chain variable region sequence of antibody GK-5A1 shown in SEQ ID NO. 8 and the light chain variable region sequence of antibody GK-5A1 shown in SEQ ID NO. 9, b) the heavy chain variable region sequence of antibody MK-3B12 shown in SEQ ID NO. 2 and the light chain variable region sequence of antibody MK-3B12 shown in SEQ ID NO. 3, c) the heavy chain variable region sequence of antibody GK-5E1 shown in SEQ ID NO. 12 and the light chain variable region sequence of antibody GK-5E1 shown in SEQ ID NO. 13, d) the heavy chain variable region sequence of antibody GK-21D3 shown in SEQ ID NO. 18 and the light chain variable region sequence of antibody GK-5E1 shown in SEQ ID NO. 19, e) the heavy chain variable region sequence of antibody MK-24C10 shown in SEQ ID NO. 20 and the light chain variable region sequence of antibody MK-24C10 shown in SEQ ID NO. 21, f) the heavy chain variable region sequence of antibody MK-24F9 shown in SEQ ID NO. 22 and the light chain variable region sequence of antibody MK-24F9 shown in SEQ ID NO. 23, g) the heavy chain variable region sequence of antibody GK-22G12 shown in SEQ ID NO. 24 and the light chain variable region sequence of antibody GK-22G12 shown in SEQ ID NO. 25.

In one embodiment, the antibody, antibody-based binding protein, modified antibody format retaining target binding capacity, antibody derivative or fragment retaining target binding capacity bi- or multispecific, and comprises:

a first portion that binds to the extracellular domain of receptor tyrosine kinase-like orphan receptor 2 (ROR2), and at least a second portion that binds to an effector antigen selected from the group consisting of CD3, CD16, NKG2D, NKp46, CD2, CD28 and/or CD25.

Some sequences are shown in the following:

TABLE 3

SEQ ID NO. 26-66 and 93-95, CDR sequences

| Name | Amino Acid Sequence of CDRs |
|---|---|
| MK-3B12 HC CDR amino acid sequences | CDR1: GYSISSGYY (SEQ ID NO. 26)<br>CDR2: IYQSGST (SEQ ID NO. 27)<br>CDR3: CAREDRAGWYPFDCW (SEQ ID NO. 28) |
| MK-3B12 LC CDR amino acid sequence | CDR1: QSISSW (SEQ ID NO. 29)<br>CDR2: KAS<br>CDR3: CQQYNNYWTF (SEQ ID NO. 30) |
| MK-7C3 HC CDR amino acid sequence | CDR1: GFTFRSHG (SEQ ID NO. 31)<br>CDR2: IWYDGSKK (SEQ ID NO. 32)<br>CDR3: CARVGAGLYLDYW (SEQ ID NO. 33) |
| MK-7C3 LC CDR amino acid sequence | CDR1: QTISNW (SEQ ID NO. 34)<br>CDR2: KAS<br>CDR3: CQQYNSYSYTF (SEQ ID NO. 35) |
| GK-1E5 HC CDR amino acid sequence | CDR1: GFTFRSYG (SEQ ID NO. 36)<br>CDR2: IWYDGSKK (SEQ ID NO. 32)<br>CDR3: CARPGIAMTGLDYW (SEQ ID NO. 37) |
| GK-1E5 LC CDR amino acid sequence | CDR1: QSISSW (SEQ ID NO. 29)<br>CDR2: KAS<br>CDR3: CQQYNNYWTF (SEQ ID NO. 30) |
| GK-5A1 HC CDR amino acid sequence | CDR1: GFTFSSYG (SEQ ID NO. 38)<br>CDR2: IWNDGSNK (SEQ ID NO. 39)<br>CDR3: CAREGSGWYDYYYGMDVW (SEQ ID NO. 40) |
| GK-5A1 LC CDR amino acid sequence | CDR1: QSISSW (SEQ ID NO. 29)<br>CDR2: KAS<br>CDR3: CQQYNSYWTF (SEQ ID NO. 41) |
| GK-2G8 HC CDR amino acid sequence | CDR1: GFTFRSYG (SEQ ID NO. 36)<br>CDR2: IWYDGSKK (SEQ ID NO. 32)<br>CDR3: CARPGVAMTGLDLW (SEQ ID NO. 43) |
| GK-2G8 LC CDR amino acid sequence | CDR1: QSISSW (SEQ ID NO. 29)<br>CDR2: KAS<br>CDR3: CQQYNNYWTF (SEQ ID NO. 30) |
| GK-5E1 HC CDR amino acid sequence | CDR1: GFTFRTYG (SEQ ID NO. 94)<br>CDR2: IWYDGSKK (SEQ ID NO. 32)<br>CDR3: CVRVRFGELYFQHW (SEQ ID NO. 44) |
| GK-5E1 LC CDR amino acid sequence | CDR1: QSISSW (SEQ ID NO. 29)<br>CDR2: KAS<br>CDR3: CQQYNSYSYSF (SEQ ID NO. 42) |

TABLE 3-continued

SEQ ID NO. 26-66 and 93-95, CDR sequences

| Name | Amino Acid Sequence of CDRs |
|---|---|
| GK-6B10 HC CDR amino acid sequence | CDR1: GFTFSRYG (SEQ ID NO. 45)<br>CDR2: IWYDGSNK (SEQ ID NO. 46)<br>CDR3: CARVAAALHFHYW (SEQ ID NO. 47) |
| GK-6B10 LC CDR amino acid sequence | CDR1: QSIDNW (SEQ ID NO. 48)<br>CDR2: KAS<br>CDR3: CQQYNSYSYTF (SEQ ID NO. 35) |
| GK-5G12 HC CDR amino acid sequence | CDR1: GFIFHTYG (SEQ ID NO. 94)<br>CDR2: IWYDGSNK (SEQ ID NO. 46)<br>CDR3: CIRVKFGDLYFQHW (SEQ ID NO. 49) |
| GK-5G12 LC CDR amino acid sequence | CDR1: QGISNY (SEQ ID NO. 50)<br>CDR2: AAS<br>CDR3: CQKYNSAPYTF (SEQ ID NO. 51) |
| GK-21D3 HC CDR amino acid sequence | CDR1: GFTFSSYG (SEQ ID NO. 38)<br>CDR2: IWYDGSNK (SEQ ID NO. 46)<br>CDR3: CARMGAINRGGGFDYW (SEQ ID NO. 52) |
| GK-21D3 LC CDR amino acid sequence | CDR1: QGISNY (SEQ ID NO. 50)<br>CDR2: AAS<br>CDR3: CQKYNSAPWTF (SEQ ID NO. 53) |
| MK-24C10 HC CDR amino acid sequence | CDR1: GFTFSSYG (SEQ ID NO. 38)<br>CDR2: IWFDGTNK (SEQ ID NO. 54)<br>CDR3: CARDKGEWFGELRYYYYGMDVW (SEQ ID NO. 55) |
| MK-24C10 LC CDR amino acid sequence | CDR1: QSLLHSNGYNY (SEQ ID NO. 56)<br>CDR2: LGS<br>CDR3: CMQALQTPYTF (SEQ ID NO. 57) |
| MK-24F9 HC CDR amino acid sequence | CDR1: GGSFSGYY (SEQ ID NO. 58)<br>CDR2: INHSRTT (SEQ ID NO. 59)<br>CDR3: CARGGEQWLVPFDYW (SEQ ID NO. 60) |
| MK-24F9 LC CDR amino acid sequence | CDR1: QSISHW (SEQ ID NO. 61)<br>CDR2: KAS<br>CDR3: CQHYNTYSRTF (SEQ ID NO. 62) |
| GK-22G12 HC CDR amino acid sequence | CDR1: GFTFSSQR (SEQ ID NO. 63)<br>CDR2: IKQDGSEK (SEQ ID NO. 64)<br>CDR3: CARDGYRNGWHIPEDYW (SEQ ID NO. 65) |
| GK-22G12 LC CDR amino acid sequence | CDR1: QGISNY (SEQ ID NO. 50)<br>CDR2: AAS<br>CDR3: CQKHNRAPWTF (SEQ ID NO. 66) |
| GK-1H2 HC CDR amino acid sequence | CDR1: GFTFRSYG (SEQ ID NO. 36)<br>CDR2: IWYDGSKK (SEQ ID NO. 32)<br>CDR3: CARPGIAMTGLDYW (SEQ ID NO. 37) |
| GK-1H2 LC CDR amino acid sequence | CDR1: QSISSW (SEQ ID NO. 29)<br>CDR2: KAS<br>CDR3: CQQYNNYWTF (SEQ ID NO. 30) |
| GK-2A9 HC CDR amino acid sequence | CDR1: GFTFRSYG (SEQ ID NO. 36)<br>CDR2: IWYDGSKK (SEQ ID NO. 32)<br>CDR3: CARPGVAMTGLDLW (SEQ ID NO. 43) |
| GK-2A9 LC CDR amino acid sequence | CDR1: QSISSW (SEQ ID NO. 29)<br>CDR2: KAS<br>CDR3: CQQYNNYWTF (SEQ ID NO. 30) |
| GK-5A6 HC CDR amino acid sequence | CDR1: GFTFRTYG (SEQ ID NO. 94)<br>CDR2: IWYDGSNK (SEQ ID NO. 46)<br>CDR3: CIRVKFGDLYFQHW (SEQ ID NO. 49) |
| GK-5A6 LC CDR amino acid sequence | CDR1: QSISSW (SEQ ID NO. 29)<br>CDR2: KAS<br>CDR3: CQQYNSYSYTF (SEQ ID NO. 35) |

TABLE 3-continued

SEQ ID NO. 26-66 and 93-95, CDR sequences

| Name | Amino Acid Sequence of CDRs |
|---|---|
| GK-21F1 HC CDR amino acid sequence | CDR1: GFTFSSYG (SEQ ID NO. 38)<br>CDR2: IWYDGSNK (SEQ ID NO. 46)<br>CDR3: CARMGAINRGGGGFDYW (SEQ ID NO. 52) |
| GK-21F1 LC CDR amino acid sequence | CDR1: QGISNY (SEQ ID NO. 50)<br>CDR2: AAS<br>CDR3: CQKYNSAPWTF (SEQ ID NO. 53) |
| MK-24C12 HC CDR amino acid sequence | CDR1: GFTFSSYG (SEQ ID NO. 38)<br>CDR2: IWFDGTNK (SEQ ID NO. 54)<br>CDR3: CARDKGEWFGELRYYYYGMDVW (SEQ ID NO. 55) |
| MK-24C12 LC CDR amino acid sequence | CDR1: QSLLHSNGYNY (SEQ ID NO. 56)<br>CDR2: LGS<br>CDR3: CMQALQTPYTF (SEQ ID NO. 57) |
| GK-21G5 HC CDR amino acid sequence | CDR1: GGSFSGYY (SEQ ID NO. 58)<br>CDR2: INHSGIT (SEQ ID NO. 93)<br>CDR3: CARGGDQWLVPFDNW (SEQ ID NO. 95) |
| GK-21G5 LC CDR amino acid sequence | CDR1: QGISNY (SEQ ID NO. 50)<br>CDR2: AAS<br>CDR3: CQKHNRAPWTF (SEQ ID NO. 66) |
| GK-23A8 HC CDR amino acid sequence | CDR1: GGSFSGYY (SEQ ID NO. 58)<br>CDR2: INHSGIT (SEQ ID NO. 93)<br>CDR3: CARGGDQWLVPFDNW (SEQ ID NO. 95) |
| GK-23A8 LC CDR amino acid sequence | CDR1: QSISHW (SEQ ID NO. 61)<br>CDR2: KAS<br>CDR3: CQHYNTYSRTF (SEQ ID NO. 62) |
| GK-21E6 HC CDR amino acid sequence | CDR1: GFTFSSQR (SEQ ID NO. 63)<br>CDR2: IKQDGSEK (SEQ ID NO. 64)<br>CDR3: CARDGYRNGWHIPEDYW (SEQ ID NO. 65) |
| GK-21E6 LC CDR amino acid sequence | CDR1: QGISNY (SEQ ID NO. 50)<br>CDR2: AAS<br>CDR3: CQKHNRAPWTF (SEQ ID NO. 66) |
| GK-22E12 HC CDR amino acid sequence | CDR1: GFTFSSQR (SEQ ID NO. 63)<br>CDR2: IKQDGSEK (SEQ ID NO. 64)<br>CDR3: CARDGYRNGWHIPEDYW (SEQ ID NO. 65) |
| GK-22E12 LC CDR amino acid sequence | CDR1: QGISNY (SEQ ID NO. 50)<br>CDR2: AAS<br>CDR3: CQKHNRAPWTF (SEQ ID NO. 66) |

In all of the foregoing aspects of the invention, the anti-ROR2 antibodies, antibody-based binding proteins, antigen-binding fragments thereof, ADCs, AECs or CARs preferably comprises a heavy chain/light chain variable region pair, the sequences of which are substantially identical to the variable region of any pair of Table 2, and particularly to one selected from the following pairs (Table 2): (i) SEQ ID NO:2 and SEQ ID NO:3; (ii) SEQ ID NO:4 and SEQ ID NO:5; (iii) SEQ ID NO:6 and SEQ ID NO:7; (iv) SEQ ID NO:8 and SEQ ID NO:9; (v) SEQ ID NO:10 and SEQ ID NO:11; (vi) SEQ ID NO:12 and SEQ ID NO:13; (vii) SEQ ID NO:14 and SEQ ID NO:15; (vii) SEQ ID NO:16 and SEQ ID NO:17; (ix) SEQ ID NO:18 and SEQ ID NO:19; (x) SEQ ID NO:20 and SEQ ID NO:21; (xi) SEQ ID NO:22 and SEQ ID NO:23; or (xii) SEQ ID NO:24 and SEQ ID NO:25. In a preferred embodiment, the fully human anti-ROR2 antibody or antigen-binding fragment comprises a heavy chain/light chain variable region pair, the sequences of which are substantially identical to one selected from the following pairs (Table 2): (i) SEQ ID NO:2 and SEQ ID NO:3; (ii) SEQ ID NO:8 and SEQ ID NO:9; (iii) SEQ ID NO:18 and SEQ ID NO:19; (iv) SEQ ID NO:20 and SEQ ID NO:21; (v) SEQ ID NO:22 and SEQ ID NO:23; or (vi) SEQ ID NO:24 and SEQ ID NO:25. In a preferred embodiment, the fully human anti-ROR2 antibody or antigen-binding fragment comprises a heavy chain/light chain variable region pair, the sequences of which are substantially identical to one selected from the following pairs (Table 2): (i) SEQ ID NO:2; SEQ ID NO:3; (ii) SEQ ID NO:8 and SEQ ID NO:9 and (iii) SEQ ID NO:20 and SEQ ID NO:21.

In a preferred embodiment, "substantially identical" means at least 90%, preferably 95%, more preferably 100% identical to the respective the variable region amino acid sequence identified in the respective SEQ ID NO.

In some embodiments, the invention provides fully human anti-ROR2 antibodies, antibody-based binding proteins, antigen-binding fragments thereof that are conservatively modified variants of the human anti-ROR2 antibodies exemplified herein. Typically, the variable regions of these variants have an amino acid sequence that is identical to one of these exemplified sequences except for conservative substitutions at one or more amino acid residues.

In all of the foregoing aspects of the invention, the human antibodies, antibody-based binding proteins, antigen-binding fragments thereof is preferably an IgA1, IgA2, IgD, IgE, IgG1, IgG2, IgG3, IgG4, IgM, F(ab)2, Fv, scFv, IgGACH2, F(ab')2, scFv2CH3, Fab, VL, VH, scFv4, scFv3, scFv2, dsFv. Fv, scFv-Fc, (scFv)2, a non-depleting IgG, a diabody, or a bivalent antibody. In a more preferred embodiment, the human antibodies, antibody-based binding proteins, antigen-binding fragments thereof are an IgG1, IgG2, IgG3, IgG4, IgM.

In the case where the human antibodies, antibody-based binding proteins or antigen-binding fragments thereof (or ADCs or CARs made therewith) are bivalent, it is preferred that they bind to both human ROR2 and human CD3.

In a preferred embodiment, the anti-ROR2 antibodies, antibody-based binding proteins, antigen-binding fragments thereof, ADCs, AECs or CARs of the invention bind to human ROR2 and to cynomolgus ROR2 and compete for binding with an antibody comprising the variable domains of GK-5A1, MK-3B12, GK-5E1, MK-21D3, MK-24C10, MK-24F9 or MK-22G12, and preferably with an antibody comprising the variable domains of GK-5A1, MK-3B12, MK-24C10, MK-24F9 or MK-22G12.

In a preferred embodiment, the anti-ROR2 antibodies, antibody-based binding proteins, antigen-binding fragments thereof, ADCs, AECs or CARs of the invention bind to human and to cynomolgus ROR2. In a preferred embodiment, the anti-ROR2 antibodies, antibody-based binding proteins, antigen-binding fragments thereof, ADCs, AECs or CARs bind to cynomolgus ROR2 and to human ROR2 and comprise the CDRs of GK-5A1, MK-3B12, GK-5E1, MK-21D3, MK-24C10, MK-24F9 or MK-22G12, and preferably of GK-5A1, MK-3B12, MK-24C10, MK-24F9 or MK-22G12. In a preferred embodiment, the anti-ROR2 antibodies, antibody-based binding proteins, antigen-binding fragments thereof, ADCs, AECs or CARs of the invention bind to cynomolgus ROR2 and to human ROR2 and comprise the variable domains of GK-5A1, MK-3B12, GK-5E1, MK-21D3, MK-24C10, MK-24F9 or MK-22G12, and preferably of GK-5A1, MK-3B12, MK-24C10, MK-24F9, or MK-22G12

In a preferred embodiment, the anti-ROR2 antibodies, antibody-based binding proteins, antigen-binding fragments thereof, ADCs, AECs or CARs of the invention bind to human ROR2 and to mouse ROR2 and compete for binding with an antibody comprising the variable domains of GK-5A1, MK-24C10 or MK-24F9, and preferably with an antibody comprising the variable domains of GK-5A1.

In a preferred embodiment, the anti-ROR2 antibodies, antibody-based binding proteins, antigen-binding fragments thereof, ADCs, AECs or CARs of the invention bind to mouse ROR2 and to human ROR2. In a preferred embodiment, the anti-ROR2 antibodies, antibody-based binding proteins, antigen-binding fragments thereof, ADCs, AECs or CARs of the invention bind to mouse ROR2 and to human ROR2 and comprise the CDRs of GK-5A1, MK-24C10 or MK-24F9, and preferably of GK-5A1. In a preferred embodiment, the anti-ROR2 antibodies, antibody-based binding proteins, antigen-binding fragments thereof, ADCs, AECs or CARs of the invention bind to mouse ROR2 and to human ROR2 and comprise the variable domains of GK-5A1, MK-24C10 or MK-24F9, and preferably of GK-5A1.

The cross reactivity of the antibodies of the invention with mouse ROR2 is particularly surprising given that these antibodies originate from mouse.

In a preferred embodiment, the anti-ROR2 antibodies, antibody-based binding proteins, antigen-binding fragments thereof, ADCs, AECs or CARs of the invention bind to human ROR2, to cynomolgus ROR2 and to mouse ROR2 and compete for binding with an antibody comprising the variable domains of GK-5A1, MK-24C10 or MK-24F9, and preferably with an antibody comprising the variable domains of GK-5A1.

In a preferred embodiment, the anti-ROR2 antibodies, antibody-based binding proteins, antigen-binding fragments thereof, ADCs, AECs or CARs of the invention bind to cynomolgus ROR2, to mouse ROR2 and to human ROR2. In a preferred embodiment, the anti-ROR2 antibodies, antibody-based binding proteins, antigen-binding fragments thereof, ADCs, AECs or CARs of the invention bind to cynomolgus ROR2, to mouse ROR2 and to human and comprise the CDRs of GK-5A1, MK-24C10 or MK-24F9, and preferably of GK-5A1. In a preferred embodiment, the anti-ROR2 antibodies, antibody-based binding proteins, antigen-binding fragments thereof, ADCs, AECs or CARs of the invention bind to cynomolgus ROR2, to mouse ROR2 and to human ROR2 and comprise the variable domains of GK-5A1, MK-24C10 or MK-24F9, and preferably of GK-5A1.

In a preferred embodiment, the anti-ROR2 antibodies, antibody-based binding proteins, antigen-binding fragments thereof, ADCs, AECs or CARs of the invention originate from a mouse. The anti-ROR2 antibodies, antibody-based binding proteins, antigen-binding fragments thereof, ADCs, AECs or CARs of the invention may present favorable lower aggregation propensity, improved manufacturability and/or higher expression levels relative fully human anti-ROR2 antibodies, antibody-based binding proteins, antigen-binding fragments thereof, ADCs. AECs or CARs obtained by methods involving phage display.

Also provided are polynucleotides encoding the fully human anti-ROR2 antibodies, antibody-based binding proteins, antigen-binding fragments thereof described herein, host cells transformed or transfected with these polynucleotides, and methods of making the various fully human anti-ROR2 antibodies, antibody-based binding proteins, antigen-binding fragments thereof described herein. The invention also provides substantially purified polynucleotides (DNA or RNA) that are identical or complementary to sequences encoding polypeptides comprising segments or domains of the antibody chains or antigen-binding fragments described herein. When expressed from appropriate expression vectors, polypeptides encoded by these polynucleotides are capable of exhibiting antigen-binding capacity. Also provided in the invention are polynucleotides that encode at least one CDR region and usually all three CDR regions from the heavy or light chain of the fully human anti-ROR2 antibodies, antibody-based binding proteins, antigen-binding fragments thereof described herein. Some other polynucleotides encode all or substantially all of the variable region sequence of the heavy chain and/or the light chain of the exemplified antibodies. Because of the degeneracy of the code, a variety of nucleic acid sequences will encode each of the immunoglobulin amino acid sequences. The polynucleotides of the invention can encode only the variable region sequence of an exemplified antibody. They can also encode both a variable region and a constant region of the antibody. Some of polynucleotide sequences of the invention nucleic acids encode a mature heavy chain variable region sequence that is substantially identical (e.g., at least 80%, 90%, or 99%) to the mature heavy chain variable region sequence shown. Some other polynucleotide sequences encode a mature light chain variable region sequence that is substantially identical to the mature light chain variable region sequence shown. Some of the polynucleotide sequences encode a polypeptide that comprises variable regions of both the heavy chain and the light chain of one of the exemplified antibody. Some other polynucleotides encode two polypeptide segments that respectively are substantially identical to the variable regions of the heavy chain and the light chain of one of the exemplified antibodies.

The polynucleotide sequences can be produced by de novo solid-phase DNA synthesis or by PCR mutagenesis of an existing sequence encoding an exemplified functional antibody. Direct chemical synthesis of nucleic acids can be accomplished by methods known in the art, such as the phosphotriester method of Narang et al., *Meth. Enzymol.* 68:90, 1979; the phosphodiester method of Brown et al., *Meth. Enzymol.* 68:109, 1979; the diethylphosphoramidite method of Beaucage et al., *Tetra. Lett.,* 22:1859, 1981; and the solid support method of U.S. Pat. No. 4,458,066. Introducing mutations to a polynucleotide sequence by PCR can be performed as described in, e.g., PCR *Technology: Principles and Applications for DNA Amplification*, H. A. Erlich (Ed.), Freeman Press, NY, NY, 1992; *PCR Protocols: A Guide to Methods and Applications*, Innis et al. (Ed.), Academic Press, San Diego, CA, 1990: Mattila et al., *Nucleic Acids Res.* 19:967, 1991; and Eckert et al. PCR Methods and Applications 1:17, 1991.

Also provided in the invention are expression vectors and host cells for producing the fully human anti-ROR2 antibodies, antibody-based binding proteins, antigen-binding fragments thereof described herein. Various expression vectors can be employed to express the polynucleotides encoding the functional antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., *Nat. Genet.* 15:345, 1997). For example, nonviral vectors useful for expression of the antibody polynucleotides and polypeptides in mammalian (e.g., human) cells include pCEP4, pREP4, pThioHis A, B & C, pcDNA3.1/His, pEBVHis A, B & C (Invitrogen, San Diego, CA), MPSV vectors, and numerous other vectors known in the art for expressing other proteins. Other useful nonviral vectors include vectors either comprising Sleeping Beauty, PiggyBac and other transposon systems or sequences allowing the transposition of the vector components by said Sleeping Beauty, PiggyBac and other transposon systems. Useful viral vectors include vectors based on lentiviruses or other retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, *Annu. Rev. Microbiol.* 49:807, 1995; and Rosenfeld et al., *Cell* 68:143, 1992

The choice of expression vector depends on the intended host cells in which the vector is to be expressed. Typically, the expression vectors contain a promoter and other regulatory sequences (e.g., enhancers) that are operably linked to the polynucleotides encoding a functional antibody chain or antigen-binding fragment. In some embodiments, an inducible promoter is employed to prevent expression of inserted sequences except under inducing conditions. Inducible promoters include, e.g., tetracycline-inducable, arabinose, lacZ, metallothionein promoters or a heat shock promoter. Cultures of transformed or transfected host cells can be expanded under non-inducing conditions without biasing the population for coding sequences whose expression products are better tolerated by the host cells. In addition to promoters, other regulatory elements may also be required or desired for efficient expression of a functional antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., *Results Probl. Cell Differ.* 20:125, 1994; and Bittner et al., *Meth. Ezymol.,* 153:516, 1987). For example, the SV40 enhancer or CMV enhancer may be used to increase expression in mammalian host cells.

The expression vectors may also provide a secretion signal sequence position to form a fusion protein with polypeptides encoded by inserted functional antibody sequences. More often, the inserted functional antibody sequences are linked to a signal sequences before inclusion in the vector. Vectors to be used to receive sequences encoding the functional antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the functional antibody chains can be either prokaryotic or eukaryotic. In some preferred embodiments, mammalian host cells are used to express and produce the antibody polypeptides of the present invention. For example, they can be either a hybridoma cell line expressing endogenous immunoglobulin genes or a mammalian cell line harboring an exogenous expression vector. These include any normal mortal or normal or abnormal immortal animal or human cell. In addition to the cell lines exemplified herein, a number of other suitable host cell lines capable of secreting intact immunoglobulins are also known in the art. These include, e.g., the CHO cell lines, various HEK 293 cell lines, various Cos cell lines, HeLa cells, myeloma cell lines, transformed cells of the B-lineage and hybridomas. The use of mammalian tissue cell culture to express polypeptides is discussed generally in, e.g., Winnacker, *From Genes to Clones*, VCH Publishers, N.Y., N.Y., 1987. Expression vectors for mammalian host cells can include expression control sequences, such as an origin of replication, a promoter, and an enhancer, and necessary processing information sites, such as ribosome binding sites. RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, EF1α and human UbC promoters exemplified herein, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transformation or electroporation is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transfection, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express the antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells that successfully express the introduced sequences in selective media. Resistant, stably transfected cells can be proliferated using tissue culture techniques appropriate for the cell type.

Invention Aspects Relating to Novel ADCs and AECs

The present invention also refers to antibody effector conjugates (AECs) or antibody drug conjugates (ADCs).

The term "antibody effector conjugates" (AEC) is used herein to describe liposome or labeling agents linked to a fully human anti-ROR2 antibody, antibody-based binding protein or antigen-binding fragment thereof as described herein. The labeling agent allows direct or indirect detection of the anti-ROR2 antibody or antigen-binding fragment to which it is attached. The liposome, as described in Bendas, BioDrugs, 15: 215-224, 2001, can allow for controlled delivery of an agent to diseased cells. In preparing a liposome conjugate, e.g., an immunoliposome, an agent such as a chemotherapeutic or other drug can be entrapped in the liposome for delivery to a target cell.

The term "antibody drug conjugates" (ADC) is used herein to describe cytotoxic and/or cytostatic agents ("toxin") linked to a fully human anti-ROR2 antibody, antibody-based binding protein or antigen-binding fragment as described herein. Cytotoxic and/or cytostatic agents are any agent known to inhibit the growth of and/or inhibit the replication of and/or kill cells, particularly malignant cells. Covalent conjugates of small molecular weight cytotoxic and/or cytostatic agents (with a molecular weight preferably <2'500 Daltons) to antibodies or antigen-binding fragments specific for tumor cells, are powerful tools to specifically target cancer cells for their destruction.

In ADCs, the toxin payload can be conjugated non-site-specifically to the antibody, antibody-based binding protein or antibody fragment via lysine or cysteine amino acid side chains employing classical chemical linkers with maleimide functionality, or other chemical known in the art that can mediate conjugation to lysine or cysteine amino acid side chains. In the ADCs of the invention, the small molecular weight payload can also be conjugated site-specifically either by chemical, chemo-enzymatic, or enzymatic conjugations known in the art, like e.g. with bifunctional linkers, linkers allowing Pictet-Spengler chemistry on formyl-glycine forming enzyme modified antibodies, by glycan-remodeled antibodies, or by bacterial transglutaminase or sortase enzymes.

According to one embodiment, the antibody drug conjugate (ADC) has the general formula A-(L)n-(T)m, in which
A is the antibody, derivative, modified format or fragment as described herein,
L is a linker,
T is a cytotoxic or cytostatic payload and in which n and m are integers between >1 and <10

According to one embodiment, the antibody effector conjugate (AEC) has the general having the general formula A-(L)n-(T)m, in which
A is the antibody, derivative, modified format or fragment according to any one of claim 1
L is a linker,
T is a label
and in which n and m are integers between >1 and <10

In a preferred embodiment, the linker comprises, or consists of, at least one selected from the group consisting of: an oligopeptide linker (including cleavable and non-cleavable oligopeptide linkers), a hydrazine linker, a thiourea linker, a self-immolative linker, a succinimidyl trans-4-(maleimidylmethyl)cyclohexane-1-carboxylate (SMCC) linker, a disulfide linker, a thioether linker, and/or a maleimide linker.

The maleimide linker optionally comprises cleavable spacers, that may be cleaved by changes in pH, redox potential and or specific intracellular enzymes.

The skilled person understands that further linkers may be suitable. Such linkers may be non-cleavable or may be cleaved by changes in pH, redox potential or specific intracellular enzymes. Cleavable oligopeptide linkers include protease-cleavable linkers. It is understood that the linker may comprise combinations of the above. For example, the linker may be a valine-citruline PAB linker.

In one embodiment, the linker has at least one of the following amino acid sequences: -LPXTGn-, -LPXAGn-, -LPXSGn-, -LAXTGn-, -LPXTGn-, -LPXTAn- or -NPQTGn-, with Gn being an oligo- or polyglycine with n being an integer between ≥1 and ≤21, An being an oligo- or polyalanine with n being an integer between >1 and ≤21, and X being any conceivable amino acid sequence.

In a preferred embodiment, the linker is conjugated to the C-terminus of at least one subdomain of the antibody, antibody, derivative, modified format or fragment.

In one embodiment, prior to conjugation
the antibody, derivative, modified format or fragment bears a sortase recognition motif fused or conjugated to the C-terminus of at least one subdomain thereof, and
the toxin or label comprises a glycine stretch with a length of between ≥1 and ≤21 glycine residues, preferably with a length of ≥2 and ≤5 glycine residues. The cytotoxic agent of the ADC can be a plant, fungal, or bacterial molecule. In some embodiments, the cytotoxic agent for conjugation to the antibody or antigen-binding fragment of the invention is a small molecule cellular toxin, a peptide toxin, or a protein toxin. Many specific examples of these toxins are well known in the art. See, e.g., Dyba et al., Curr. Pharm. Des. 10:2311-34, 2004; Kuyucak et al., Future Med. Chem. 6:1645-58, 2014: Beraud et al., Inflamm. Allergy Drug Targets, 10:32242, 2011; and Middlebrook et al., Microbiol. Rev. 48:199-221, 1984. In some embodiments, a therapeutic agent is conjugated to the antibody. For example, the therapeutic agent can be a maytansinoid (e.g., maytansinol or DM1 maytansinoid), a taxane, a calicheamicin, a cemadotin, a monomethylauristatin (e.g., monomethylauristatin E or monomethylauristatin F), a pyrrolobenzodiazepine (PBD), an indilino-benzodiazepine pseudodimer or an anthracycline. Therapeutic agents also include vincristine and prednisone. In various embodiments, the therapeutic agent that may be employed in the invention can be an antimetabolite (e.g., an antifolate such as methotrexate, a fluoropyrimidine such as 5-fluorouracil, cytosine arabinoside, or an analogue of purine or adenosine); an intercalating agent (for example, an anthracycline such as doxorubicin, PNU-159682, daunomycin, epirabicin, idarubicin, mitomycin-C, dactinomycin, or mithramycin, or other intercalating agents such as pyrrolobenzodiazepine); a DNA-reactive agent such as calicheamicins, tiancimycins, and other enediynes: a platinum derivative (e.g., cisplatin or carboplatin); an alkylating agent (e.g., nitrogen mustard, melphalan, chlorambucil, busulphan, cyclophosphamide, ifosfamide nitrosoureas or thiotepa); an RNA polymerase inhibitor such as α-amanitin; an antimitotic agent (e.g., a *vinca* alkaloid such as vincristine, or a taxoid such as paclitaxel or docetaxel); a topoisomerase inhibitor (for example, etoposide, teniposide, amsacrine, topotecan); a cell cycle inhibitor (for example, a flavopyridol); or a microbtubule agent (e.g., an epothilone, a tubulysine, a pre-tubulysine, discodermolide analog, or eleutherobin analog). A therapeutic agent can be a proteosome inhibitor or a topoisomerase inhibitor such as bortezomib, amsacrine, etoposide, etoposide phosphate, teniposide, or doxorubicin. Therapeutic radioisotopes include iodine ($^{131}$I), yttrium ($^{90}$Y), lutetium ($^{177}$Lu), actinium ($^{225}$Ac), praseodymium, astatine (At), rhenium (Re), bismuth (Bi or Bi), and rhodium (Rh). Antiangiogenic agents include linomide, bevacuzimab, angiostatin, and razoxane.

In a preferred embodiment of the ADC, the cytotoxic or cytostatic payload is at least one selected from the group consisting of, or a derivative of:
maytansinoids,
auristatins,
anthracyclins,
calcheamicins,
tubulysins
duocarmycins
radioisotopes
liposomes comprising a toxid payload
protein toxins
taxanes
indilino-benzodiazepine pseudodimers, and/or
pyrrolobenzodiazepines.

In a preferred embodiment of the ADC, the toxin is selected from PNU-159682 as described in Quintieri et al. (2005) and derivatives thereof, maytansine, monomethyl auristatin MMAE, and monomethyl auristatin MMAF. In a preferred embodiment of the ADC, the toxin, joined to the linker at its wavy line, is of formula (i), as described in WO 2016/102679:

formula (i)

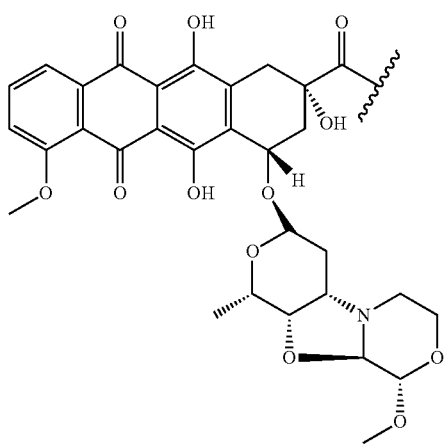

In the embodiment where the toxin is of formula (i), it is preferred that the linker comprise an alkyldiamino group of the form $NH_2—(CH_2)_m—NH_2$, where $m \geq 1$ and $\leq 11$, preferably m=2, such that one amino group is directly linked at the wavy line of formula (i) to form an amide bond. It is moreover preferred that the second amino group is linked to an oligopeptide linker, which is more preferably an oligoglycine.

In some embodiments, the molecule for conjugation to the antibody is a protein (e.g., an antibody) or an RNA or DNA aptamer.

In a preferred embodiment of the AEC, the label is at least one selected from the group consisting of: a fluorescent label (including a fluorescent dye or a fluorescent protein), a chromophore label, a radioisotope label containing iodine (e.g., $^{125}$I), gallium ($^{67}$Ga), indium ($^{111}$I), technetium ($^{99m}$Tc), phosphorus ($^{32}$P), carbon ($^{14}$C), tritium ($^{3}$H), other radioisotope (e.g., a radioactive ion), and/or a protein label such as avidin or streptavidin.

In a preferred embodiment of the ADC or AEC, the ADC or AEC has a stoichiometric ratio between antibody and payload of any integer between $\geq 1$ and $\leq 10$, preferably 2 and 4. In the case of the ADC, this ratio may also be referred to as the drug to antibody ratio ("DAR"). In the case of a mixture or collection of ADCs, the DAR may be a rational number representing the average of the individual integer DARs.

In one embodiment of the ADC or AEC, only one or more heavy chains of the antibody or antigen-binding fragment according are conjugated to a payload.

In one embodiment of the ADC or AEC, only one or more light chains of the antibody or antigen-binding fragment according are conjugated to a payload.

It is understood that a given ADC or AEC may comprise different toxins or labels bound simultaneously; it is also possible that the anti-ROR2 antibody be linked to a combination of both one or more labels and one or more toxins.

The antibodies or antigen-binding fragments of the invention can be conjugated to a synthetic molecule using any type of suitable conjugation. Recombinant engineering and incorporated selenocysteine (e.g., as described in U.S. Pat. No. 8,916,159) can be used to conjugate a synthetic molecule. Other methods of conjugation can include covalent coupling to native or engineered lysine side-chain amines or cysteine side-chain thiols. See, e.g., Wu et al., *Nat. Biotechnol,* 23: 1 137-1 146 (2005). The synthetic molecule can be any molecule such as one targeting a tumor.

In a preferred embodiment, the ADC or AEC is obtained by means of site-specific sortase-enzyme mediated antibody conjugation (SMAC-technology), which is enablingly disclosed in WO2014140317 assigned to the same applicant. The content of this publication is incorporated by reference herein. Sortases (also called sortase transpeptidases) form a group of prokaryotic enzymes that modify surface proteins by recognizing and cleaving a specific peptide motif called "sortase recognition motif" or "sortase tag". Usually, a given sortase enzyme recognizes one or more sortase recognition motifs. Sortase enzymes can be naturally occurring, or may have undergone genetic engineering (Dorr et al., 2014), and are used, in the SMAC technology, to conjugate two proteins one of which is bearing such recognition motif, while the other one is bearing a oligo-glycine peptide $(Gly)_n$. It is important to understand that, in one specific embodiment (where *Streptococcus pyogenes* sortase A is used, see below), the oligo-glycine $(Gly)_n$ can optionally be replaced by an oligo-alanine $(Ala)_n$.

In a preferred embodiment, the ADC or AEC is obtained by means of site-specific sortase-enzyme mediated conjugation of:

a) an antibody or antigen-binding fragment as described herein carrying one or more sortase recognition motifs, and b) one or more payloads carrying an oligoglycine tag;

or a) an antibody or antigen-binding fragment as described herein carrying one or more oligoglycine tags, and b) one or more payloads carrying a sortase recognition motif.

It is important to understand that, in one specific embodiment (where *Streptococcus pyogenes* sortase A is used, see below), the oligo-glycine $(Gly)_n$ can optionally be replaced by an oligo-alanine $(Ala)_n$.

Preferably, the sortase recognition motif is fused or conjugated to the C-terminus of at least one subdomain of the antibody.

Preferably, the oligo glycine tag has a length between ≥1 and ≤21 glycine residues, preferably with a length between ≥2 and ≤5 amino acids.

The invention also refers to a method of producing an AEC or ADC, which method comprises the following steps:

a) providing an antibody, derivative, modified format or fragment as described herein, which antibody or antigen-binding fragment carries one or more sortase recognition motifs, b) providing one or more payloads carrying an oligoglycine tag, and c) conjugating the antibody or antigen-binding fragment and one or more payloads by means of sortase-mediated conjugation.

The term "oligoglycine tag" (also called Gn or G(n)) relates to an oligoglycine the length n of which can be between ≥1 and ≤21, preferably between ≥1 and ≤5.

The invention also refers to a method of producing an AEC or ADC, which method comprises the following steps:

a) providing an anti-ROR2 antibody or antigen-binding fragment as described herein, which antibody or antigen-binding fragment carries one or more oligoglycine tags, b) providing one or more payloads carrying a sortase recognition motif, and c) conjugating the antibody or antigen-binding fragment and one or more payloads by means of sortase-mediated conjugation.

According to another embodiment, said sortase enzyme recognition motif comprises at least one of the following amino acid sequences: LPXTG, LPXAG, LPXSG, LAXTG, LPXTA or NPQTN, with X being any conceivable amino acid sequence.

According to another embodiment, the resulting linker has at least one of the following amino acid sequences: -LPXTGn-, -LPXAGn-, -LPXSGn-, -LAXTGn-, -LPXTGn-, -LPXTAn- or -NPQTGn-, with Gn being an oligo- or polyglycine with n being an integer between ≥1 and ≤21. An being an oligo- or polyalanine with n being an integer between ≥1 and ≤21, and X being any conceivable amino acid sequence.

The following table shows the recognition tags and the peptides derived therefrom to be part of the linker:

TABLE 4

| Sortase recognition motifs and resulting linkers | |
|---|---|
| *Staphylococcus aureus* sortase A recognition sequence, with X being any amino acid | -LPXTG |
| *Staphylococcus aureus* sortase A recognition sequence, with X being any amino acid | -LPXAG |
| recognition sequence for *Staphylococcus aureus* sortase A or engineered sortase A 4S-9 from *Staphylococcus aureus*, with X being any amino acid | -LPXSG |
| recognition sequence for engineered sortase A 2A-9 from *Staphylococcus aureus*, with X being any amino acid | -LAXTG |
| *Streptococcus pyogenes* sortase A recognition sequence, with X being any amino acid | -LPXTA |
| *Staphylococcus aureus* sortase recognition sequence | -NPQTN |
| Linker derived from *Staphylococcus aureus* sortase A recognition sequence, with X being any amino acid and n ≥ 1 and ≤21 | -LPXT(Gn)- |
| Linker derived from *Staphylococcus aureus* sortase A recognition sequence, with X being any amino acid and n ≥ 1 and ≤21 | -LPXA(Gn)- |
| Linker derived from recognition sequence for *Staphylococcus aureus* sortase A or engineered sortase A 4S-9 from *Staphylococcus aureus*, with X being any amino acid and n ≥ 1 and ≤21 | -LPXS(Gn)- |
| Linker derived from recognition sequence for engineered sortase A 2A-9 from *Staphylococcus aureus*, with X being any amino acid and n ≥ 1 and ≤21 | -LAXT(Gn)- |
| Linker derived from *Streptococcus pyogenes* sortase A recognition sequence, with X being any amino acid and n ≥ 1 and ≤21 | -LPXT(Gn)- or -LPXT(An)- |
| Linker derived from *Staphylococcus aureus* sortase recognition sequence, with n ≥ 1 and ≤21 | -NPQT(Gn)- |

Engineered sortases, including but not limited to sortase A mutant 2A-9 and sortase A mutant 4S-9 from *Staphylococcus aureus*, are described in Dorr et al. (2014) and mutants described in Chen et al. (2011).

As background and to exemplify the general concept of sortase transpeptidation, Sortase A uses an oligo-glycine-stretch as a nucleophile to catalyze a transpeptidation by which the terminal amino group of the oligo-glycine effects a nucleophilic attack on the peptide bond joining the last two C-terminal residues of the sortase tag. This results in breakage of that peptide bond and formation of a new peptide bond between the C-terminally second-to-last residue of the sortase tag and the N-terminal glycine of the oligo-glycine peptide, i.e. resulting in a transpeptidation.

It is important to understand that, in one specific embodiment (where *Streptococcus pyogenes* sortase A is used, see above), the oligo-glycine (Gly)n can optionally be replaced by an oligo-alanine (Ala)n.

Prior to sortase conjugation, the sortase recognition motif may, at its C-terminus, furthermore carry other tags, like His-tags. Myc-tags or Strep-tags (see FIG. 4a of WO 2014/140317, the content of which is incorporated by reference herein). However, because the peptide bond between the 4th and 5th amino acid of the sortase tag is cleaved upon sortase A mediated conjugation, these additional tags do not appear in the conjugated product.

The sortase tag may, for example, be fused to a C-terminus of a binding protein, or to a domain or subunit thereof, by genetic fusion and co-expressed therewith. In another preferred embodiment, the sortase tag may directly be appended to the last naturally occurring C-terminal amino acid of the immunoglobulin light chains or heavy chains, which in case of the human immunoglobulin kappa light chain is the C-terminal cysteine residue, and which in the case of the human immunoglobulin IgG1 heavy chain may be the C-terminal lysine residue encoded by human Fcγ1 cDNA. However, another preferred embodiment is also to directly append the sortase tag to the second last C-terminal glycine residue encoded by human Fcγ1 cDNA, because usually terminal lysine residues of antibody heavy chains are clipped off by posttranslational modification in mammalian cells. Therefore, in more than 90% of the cases naturally occurring human IgG1 lacks the C-terminal lysine residues of the IgG1 heavy chains. Therefore, one preferred embodiment of the invention is to omit the C-terminal lysine amino acid residues of human IgG1 heavy chain constant regions in expression constructs for sortase recognition-motif tagged Igγ1 heavy chains. Another preferred embodiment is to include the C-terminal lysine amino acid residues of human IgG1 heavy chain constant regions in expression constructs for sortase recognition-motif tagged Igγ1 heavy chains.

In another preferred embodiment the sortase or oligoglycine tag may be appended to the C-terminus of a human immunoglobulin IgG1 heavy chain where the C-terminal lysine residue encoded by human Fcγ1 cDNA is replaced by an amino acid residue other than lysine to prevent unproductive reactions of sortase with the ε-amino group of said C-terminal lysine residue leading to inter-heavy chain cross-linking.

We have described previously that in some cases (e.g. at the C-terminus of the Ig kappa light chains, see: Beerli et al. (2015) PloS One 10, e131177) it is beneficial to add additional amino acids between the C-terminus of the binding protein and the sortase tag. This has been shown to improve sortase enzyme conjugation efficiencies of payloads to the binding protein. In the case of Ig kappa light chains, it was observed that by adding 5 amino acids between the last C-terminal cysteine amino acid of the Ig kappa light chain and the sortase pentapeptide motif improved the kinetic of conjugation, so that the C-termini of Ig kappa light chains and Ig heavy chains could be conjugated with similar kinetics (see: Beerli et al. (2015) PloS One 10, e131177). Therefore, it is another preferred embodiment that optionally $\geq 1$ and $\leq 11$ amino acids are added in between the last C-terminal amino acid of a binding protein or antibody subunit and the sortase tag.

In a preferred embodiment, a $G_nS$ peptide (wherein n is between $\geq 1$ and $\leq 21$, preferably between $\geq 1$ and $\leq 5$ is added between the last C-terminal amino acid of a binding protein or antibody subunit and the sortase tag.

Finally, in another preferred embodiment, additional amino acids between the C-terminus of the binding protein and the sortase or oligoglycine tag may beneficially be included that comprise a sequence and/or linker that is cleavable by hydrolysis, by a pH change or by a change in redox potential, or that is cleavable by a non-sortase enzyme, e.g., by proteases.

According to another aspect of the invention, a ROR2 chimeric antigen receptor (CAR) employing the antibody, derivative, modified format or fragment according to the above description is provided, fused or conjugated to at least one transmembrane region and at least one intracellular domain.

Further, a cell comprising such a chimeric antigen receptor is provided, which cell is preferably an engineered T-cell.

Further, the use of the antibody, derivative, modified format or fragment, the antibody drug conjugate or the CAR or cell according to the above description for the treatment of a patient that is
    suffering from,
    at risk of developing, and/or
    being diagnosed for
a neoplastic disease is provided.

As an alternative, a method of treating a patient suffering from, at risk of developing, and/or being diagnosed for a neoplastic disease is provided, which method comprises the administration of one or more therapeutically active doses of the antibody, the antibody drug conjugate or the CAR or cell according to the above description.

In one embodiment, the neoplastic disease is at least one selected from the group consisting of
    renal cell carcinoma
    osteosarcoma
    kidney cancer According to one aspect, a pharmaceutical composition comprising the antibody, derivative, modified format or fragment, the antibody drug conjugate or the CAR or cell according to the above description is provided, together with one or more pharmaceutically acceptable ingredients.

In another aspect, the invention provides methods of killing or inhibiting the growth of a cell expressing ROR2 in vitro or in a patient is provided, which method comprises administering to the cell a pharmaceutically effective amount or dosis of the antibody, derivative, modified format or fragment, the antibody drug conjugate or the CAR or cell according to the above description or the pharmaceutical composition according to the above description.

Preferably, the cell expressing ROR2 is a cancer cell.

The methods entail administering a therapeutically effective amount of an anti-ROR2 antibody, antibody-based binding protein, antibody fragment thereof, ADC or CAR disclosed herein to a subject in need of treatment. This enables killing or inhibiting the growth of the cell expressing ROR2 in the subject. In various embodiments, the cell expressing ROR2 is a tumor cell. In a related aspect, the invention provides methods of treating a disease or condition associated with elevated expression of ROR2 in a subject. These methods involve administering a therapeutically effective amount of an anti-ROR2 antibody, antibody-based binding protein, antibody fragment thereof. ADC or CAR of the invention to a subject that is afflicted with a disease or condition associated with elevated expression of ROR2. This enables treatment of the disease or condition in the subject. Some of these methods are directed to treating a cancer in the subject. Cancers that are amendable to treatment with methods of the invention include, e.g., neuroblastoma, sarcoma (and especially osteosarcoma), renal cell carcinoma, breast cancer, testicular cancer, ovarian cancer, pancreatic cancer, kidney cancer, renal cancer, gastric cancer, prostate cancer, head and neck cancer, melanoma, squamous cell carcinoma, multiple myeloma and other cancers.

In various embodiments, the administered anti-ROR2 antibody, antibody-based binding protein, antibody fragment thereof, or ADC or CAR based thereon, are F(ab)2, Fv, scFv, IgGACH2, F(ab')2, scFv2CH3, Fab, VL, VH, scFv4, scFv3, scFv2, dsFv, Fv, (scFv)2, or a synthetic IgG. In some embodiments, the administered anti-ROR2 antibody, antibody-based binding protein or antibody fragment thereof is conjugated to a synthetic molecule. In some of these embodiments, the anti-ROR2 antibody, antibody-based binding protein, antibody fragment thereof is conjugated to a transmembrane region and an intracellular T-cell receptor (TCR) signaling domain to form a chimeric antigen receptor (CAR). In some embodiments, the chimeric antigen receptor (CAR) is present on a T cell to be administered to the subject. In some other embodiments, the antibody can be conjugated to a cytotoxic agent, a radioisotope, or a liposome.

The terms "treating" or "treatment" used herein do not necessarily imply 100% or complete treatment. Rather, there are varying degrees of treatment recognized by one of ordinary skill in the art as having a potential benefit or therapeutic effect. In this respect, the inventive method can provide any amount of any level of treatment. Furthermore, the treatment provided by the inventive method can include the treatment of one or more conditions or symptoms of the disease being treated. In particular, the treatment may be administered as an intravenous infusion.

In one embodiment, the fully human anti-ROR2 antibody, antibody-based binding protein or antibody fragment thereof, bi- or multispecific antibody. ADC or CAR is administered as a monotherapy. In an alternative embodiment, the fully human anti-ROR2 antibody, antibody-based binding protein or antibody fragment thereof, bi- or multispecific antibody, ADC or CAR is administered as with or in parallel or series to further therapeutic agents.

In particular, the fully human anti-ROR2 antibody antibody-based binding protein or antibody fragment thereof, bi- or multispecific antibody. ADC or CAR may be administered at a dosage of about 0.1-20 mg/kg.

The term "subject" refers to human and non-human animals (especially non-human mammals), and preferably to human animals. In spite of the antibody, antibody-based binding protein or antibody fragment thereof, bi- or multispecific antibody, ADC or CAR binding to ROR2, they may also bind to ROR2 from other species making them effective for treatment of these species.

The present invention thus also refers to a method for treating a subject suffering from, being at risk of developing, and/or being diagnosed with a neoplastic disease, comprising administration of a fully human anti-ROR2 antibody, antibody-based binding protein or antibody fragment thereof, ADC or CAR, as described herein.

In particular, said neoplastic disease is selected from the group consisting of; neuroblastoma, sarcoma (and especially osteosarcoma), renal cell carcinoma, breast cancer, testicular cancer, ovarian cancer, pancreatic cancer, kidney cancer, renal cancer, gastric cancer, prostate cancer, head and neck cancer, melanoma, squamous cell carcinoma, multiple myeloma and other cancers.

In some related aspects, the invention provides pharmaceutical compositions or kits that contain a therapeutically effective amount of a fully human anti-ROR2 antibody or antibody, antibody-based binding protein or antibody fragment thereof, bi- or multispecific antibody, or ADC described herein and a pharmaceutically acceptable carrier. Some kits of the invention can additionally contain one or more immunoassay buffers.

In some embodiments, the compositions of the invention contain a carrier, desirably a pharmaceutically acceptable carrier. The pharmaceutically acceptable carrier can be one or more compatible solid or liquid fillers, diluents, other excipients, or encapsulating substances which are suitable for administration into a human or veterinary subject (e.g., a physiologically acceptable carrier or a pharmacologically acceptable carrier). The term "carrier" denotes an organic or inorganic ingredient, natural or synthetic, with which the active ingredient is combined to facilitate the use of the active ingredient, e.g., the administration of the active ingredient to a subject. The pharmaceutically acceptable carrier can be co-mingled with one or more of the active components, e.g., a hybrid molecule, and with each other, when more than one pharmaceutically acceptable carrier is present in the composition, in a manner so as not to substantially impair the desired pharmaceutical efficacy. Pharmaceutically acceptable materials typically are capable of administration to a subject, e.g., a patient, without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

Pharmaceutical compositions of the invention can additionally contain suitable buffering agents, including, for example, acetic acid in a salt, citric acid in a salt, boric acid in a salt, and phosphoric acid in a salt. The compositions can also optionally contain suitable preservatives, such as benzalkonium chloride, chlorobutanol, parabens, and thimerosal. Pharmaceutical compositions of the invention can be presented in unit dosage form and can be prepared by any suitable method, many of which are well known in the art of pharmacy. Such methods include the step of bringing the antibody or antigen-binding fragment of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in Remington's Pharmaceutical Sciences, Mack Publishing Co., Easton, PA.

Preparation of pharmaceutical compositions of the invention and their various routes of administration can be carried out in accordance with methods well known in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and triglycerides; hydrogel release systems; sylastic systems: peptide-based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The invention also provides kits suitable for carrying out the methods of the invention. Typically, the kits contain two or more components required for performing the therapeutic or diagnostic methods of the invention. Kit components include, but are not limited to, one or more antibodies or antigen-binding fragments of the invention, appropriate reagents, and/or equipment. In some embodiments, the kits can contain an antibody or antigen-binding fragment of the invention and an immunoassay buffer suitable for detecting ROR2 (e.g. by ELISA, flow cytometry, magnetic sorting, or FACS). The kit may also contain one or more microtiter plates, standards, assay diluents, wash buffers, adhesive plate covers, magnetic beads, magnets, and/or instructions for carrying out a method of the invention using the kit. The kit can include an antibody or antigen-binding fragment of the invention bound to a substrate (e.g., a multi-well plate or a chip), which is suitably packaged and useful to detect ROR2. In some embodiments, the kits include an antibody or antigen-binding fragment of the invention that is conjugated to a label, such as, a fluorescent label, a biologically active enzyme label, a luminescent label, or a chromophore label. The kits can further include reagents for visualizing the conjugated antibody, e.g., a substrate for the enzyme. In some embodiments, the kits include an antibody or antigen-binding fragment of the invention that is conjugated to a contrast agent and, optionally, one or more reagents or pieces of equipment useful for imaging the antibody in a subject.

Generally the antibody or antigen-binding fragment of the invention in a kit is suitably packaged, e.g., in a vial, pouch, ampoule, and/or any container appropriate for a therapeutic or detection method. Kit components can be provided as concentrates (including lyophilized compositions), which may be further diluted prior to use, or they can be provided at the concentration of use. For use of the antibody antibody, derivative, modified format or fragment of the invention in vivo, single dosages may be provided in sterilized containers having the desired amount and concentration of components.

Invention Aspects Relating to Methods of Detection

According to another aspect of the invention, a method of determining whether a suspected patient is
suffering from,
at risk of developing, and/or
diagnosed for a neoplastic disease or immune disease is provided, said method comprising the treatment of a sample taken from that subject with an antibody effector conjugate according to the above description.

In one embodiment, the neoplastic disease or immune disease is suitable for treatment with an anti ROR2 antibody, anti ROR2 antibody drug conjugate, or a CAR T cell comprising an anti ROR2 antibody.

In some other embodiments, the invention provides method for detecting in a biological sample an altered level of ROR2 (e.g., cell surface ROR2), for example, relative to a control, either by FACS, immunohistochemistry (IHC) or Western Blotting. Generally, the method includes contacting a biological sample with an antibody, antibody-based binding protein, antibody fragment thereof of the invention and determining the amount of antibody that selectively binds to material (e.g., cells) in the sample to thereby determine the level of ROR2 in the biological sample. A biological sample can be from a cell culture or from a test subject, e.g., a plasma or a tissue sample from a subject that has, is suspected to have, or is at risk of developing a disease or condition associated with elevated ROR2 in a subject. A control level desirably corresponds to the ROR2 level detected using the same antibody in a corresponding sample (s) from one or more control cultures or disease-free subjects. Methods of using the antibody of the invention to determine ROR2 levels can include any immunoassay such as immuno-(Western) blotting, enzyme-linked immunosorbent assay (ELISA), Immunohistochemistry (IHC) and flow cytometry, e.g., fluorescence-activated cell sorting (FACS) analysis.

The methods of detection can be used to screen for the presence of a disorder associated with elevated ROR2. The methods include obtaining a sample from a test subject in need of screening, e.g., a subject that has, is suspected to have, or is at risk of developing a disorder associated with elevated ROR2. The level of ROR2 (e.g., the amount or concentration) in the sample is measured using an antibody, antibody-based binding protein, antibody fragment thereof of the invention, and the level in the sample is compared to a control level of ROR2. The control level represents, for example, the mean level (e.g., the amount or concentration) in sample(s) from one or, preferably, multiple control group subjects that do not have a disorder associated with elevated ROR2. Alternatively, the control level can correspond to the level or mean level of ROR2 in one or more samples taken from the test subject at one or more prior times, such as when the test subject did not have or did not exhibit, a condition associated with elevated ROR2. A significantly higher level of ROR2 in the biological sample relative to the control level is indicative of a disorder associated with elevated ROR2 in the subject. In subjects such as humans, where cell surface ROR2 expression is largely restricted to embryonic development, a control level of ROR2 can be zero or none. Thus, in some embodiments of the method of detection provided by the invention, any significant and detectable amount of ROR2 in a biological sample can be indicative of a disorder associated with elevated ROR2 in the subject.

Additionally, the methods of detection can be used to monitor the progress of a disorder associated with elevated ROR2. The method includes obtaining a sample from a subject in need of screening, e.g., a subject having been diagnosed or suspected to have a disorder associated with elevated ROR2. The level of ROR2 in the sample is measured using an antibody, antibody-based binding protein, antibody fragment thereof of the invention, and the level in the sample is compared to a control level corresponding to the level or mean level of ROR2 in one or more samples taken from the test subject at one or more prior times. Levels of ROR2 that are significantly elevated or decreased relative to control indicate that the subject's disorder is deteriorating or improving, respectively. The foregoing methods of detection can be used to screen for the presence or to monitor the progress of disorders including, for example, CLL, ALL, mantle cell lymphoma, neuroblastoma, sarcoma, renal cell carcinoma, breast cancer, lung cancer, colon cancer, head and neck cancer, melanoma, and other cancers.

In some embodiments, the invention provides methods for screening a subject for an altered level of ROR2. Generally, the methods entail administering to the subject an antibody, antibody-based binding protein, antibody fragment thereof of the invention that is conjugated to a label (e.g., a contrast agent), imaging the subject in a manner suitable for detecting the label, and determining whether a region in the subject has an altered density or concentration of label as compared to the background level of label in proximal tissue. Alternatively, the methods include determining whether there is an altered density or concentration of label in a region as compared to the density or concentration of label previously detected in the same region of the subject. Methods of imaging a subject can include x-ray imaging, x-ray computed tomography (CT) imaging (e.g., CT angiography (CTA) imaging), magnetic resonance (MR) imaging, magnetic resonance angiography (MRA), nuclear medicine, ultrasound (US) imaging, optical imaging, elastography, infrared imaging, microwave imaging, and the like, as appropriate for detecting the label conjugated to the antibody. In a preferred embodiment, the subject has, is suspected to have, or is at risk of developing an ROR2-expressing tumor, such as CLL, ALL, mantle cell lymphoma, neuroblastoma, sarcoma, renal cell carcinoma, breast cancer, lung cancer, colon cancer, head and neck cancer, melanoma, and other cancers, and the method is used to screen for or detect the presence of the tumor. In another embodiment, the method can be used to monitor the size or density of a ROR2-expressing tumor over time, e.g., during a course of treatment.

The invention thus provides methods for detecting an altered ROR2 level in a subject. The methods involve (a) obtaining a biological sample from the subject, (b) contacting the sample with an anti-ROR2 antibody, antibody-based binding protein, antibody fragment thereof disclosed herein, (c) determining the level of ROR2 in the biological sample, and (d) comparing the level of ROR2 in the biological sample to a control level of ROR2. This allows determination of whether the ROR2 level in the biological sample is altered relative to the control level of ROR2. In these methods, an increased ROR2 level in the subject relative to the control level is indicative of a disease or condition associated with elevated expression of ROR2 in the subject. For example, detection of elevated ROR2 expression can be indicative of the presence of neuroblastoma, osteosarcoma, renal cell carcinoma, breast cancer, gastric cancer, prostate cancer, melanoma, squamous cell carcinoma, or multiple myeloma in the subject.

In still another aspect, the invention provides methods for detecting a ROR2-expressing tumor in a subject. These methods entail (a) administering an anti-ROR2 antibody, antibody-based binding protein, antibody fragment thereof of the invention to a subject that has, is suspected to have, or is at risk of developing an ROR2-expressing tumor, and (b) imaging the subject for a region of altered conjugated label density or concentration, wherein the density or concentration is relative to (i) background in proximal tissue or (ii) the density or concentration previously detected in the same region of the subject. The existence of a region of altered conjugated label density or concentration is an indication of the presence of a ROR2-expressing tumor in the subject.

Invention Aspects Relating Cells and T Cells

In some embodiments, the invention provides methods for treating a subject that has, is suspected to have, or is at risk of developing a disorder associated with elevated levels of ROR2 by adoptive transfer of the genetically engineered T-cells described herein, which express an antibody or antigen-binding fragment of the invention as a chimeric antigen receptor (CAR) that selectively binds ROR2. Recombinant technology can be used to introduce CAR-encoding genetic material into any suitable T-cells, e.g., central memory T-cells from the subject to be treated. The T cells carrying the genetic material can be expanded (e.g., in the presence of cytokines). The genetically engineered T-cells are transferred, typically by infusion, to the patient. The transferred T-cells of the invention can then mount an immune response against ROR2 expressing cells in the subject. The adoptive transfer method can be used, for example, to treat subjects that have or are suspected to have any of the cancers associated with ROR2, including CLL, ALL, mantle cell lymphoma, neuroblastoma, sarcoma, renal cell carcinoma, breast cancer, lung cancer, colon cancer, head and neck cancer, melanoma, and other cancers. In some embodiments, the foregoing methods of treatment can further include co-administering a second therapeutic agent for treating the disorder associated with elevated ROR2. For example, when the disorder to be treated involves an ROR2-expressing cancer, the method can further include co-administration of a cytotoxic, cystostatic, or antiangiogenic or immune-stimulatory agent (e.g. immune-checkpoint inhibitor antibodies, for instance, but not limited to, those binding to PD1, PDL1, CTLA4, OX40, TIM3, GITR, LAG3 and the like) suitable for treating the cancer. If the cancer is a B-cell malignancy, the method can further include, for example, co-administration of rituximab, alemtuzumab, ofatumumab, ocrelizumab, or a CHOP chemotherapeutic regimen.

The invention thus further provides eukaryotic or non-eukaryotic cells (e.g., T lymphocytes) that have been recombinantly engineered to produce the fully human anti-ROR2 antibodies or antigen-binding fragments of the invention. The eukaryotic or non-eukaryotic cells can be used as an expression system to produce the antibody of the invention. In some embodiments, the invention provides ROR2 targeted immune cells that are engineered to recombinantly express a ROR2-specific non-human or humanized antibody or antigen-binding fragment of the invention. For example, the invention provides a T cell engineered to express a human anti-ROR2 antibody or antigen-binding fragment of the invention (e.g., an scFv, scFv-Fc, or (scFv)2), which is linked to a synthetic molecule containing one or more of the following domains: a spacer or hinge region (e.g., a CD28 sequence or a IgG4 hinge-Fc sequence), a transmembrane region (e.g., a transmembrane canonical domain), and an intracellular T-cell receptor (TCR) signaling domain, thereby forming a chimeric antigen receptor (CAR) or T-body. Intracellular TCR signaling domains that can be included in a CAR (or T-body) include, but are not limited to, CD3ζ, FcR-γ, and Syk-PT signaling domains as well as the CD28, 4-1BB, and CD134 co-signaling domains. Methods for constructing T-cells expressing a CAR (or T-body)

are known in the art. See, e.g., Marcu-Malina et al., Expert Opinion on Biological Therapy, Vol. 9, No. 5 (posted online on Apr. 16, 2009).

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'→3'.

Example 1: Antibody Library Generation and Screening (FIG. 1)

hROR2-TwinStrep antigen expression. The EBNA expression vector pCB14b-hROR2-Thr-ECD-TwinStrep (where Thr is threonine), directing expression of the hROR2 extracellular domain (ECD), C-terminally tagged with a TwinStrep tag, was transfected into HEK293T using Lipofectamine® LTX with PLUS™ Reagent (Thermo Fisher Scientific, 15388100). Following a 1-day incubation (37° C., 5% $CO_2$, growth media: Dulbecco's Modified Eagle Medium (DMEM) High Glucose (4.5 g/L) with L-Glutamine with 10% (v/v) Fetal Calf Serum (FCS), 100 IU/mL of Pen-Strep-Fungizone and 2 mM L-glutamine (all Bioconcept)), cells were expanded under selection conditions (2 µg/mL of puromycin (Sigma-Aldrich, P8833-25 mg stock at 2 mg/mL)). Cells were split and further expanded (37° C., 5% $CO_2$); once confluency was reached, hyperflasks were coated with 20 µg/ml poly-L-Lysine (Sigma-Aldrich. P1524) for 2 hrs at 37° C. and washed twice with PBS. Then, cells were trypsinized, washed with PBS and plated onto poly-L-lysine-coated hyperflasks. After reaching confluency again, cells were washed with PBS followed by media replacement using production media (DMEM/F-12, Gibco-Thermo Fisher Scientific, 31330-038) supplemented with 1 µg/mL puromycin (Sigma-Aldrich, P8833), 100 IU/mL of Pen-Strep-Fungizone (Bioconcept, 4-02F00-H), 161 µg/mL of N-acetyl-L-cysteine (Sigma-Aldrich, A8199) and 10 µg/mL of L-glutathione reduced (Sigma-Aldrich. G6529). Supernatant, harvested bi-weekly and filtered (0.22 µm) to remove cells, was stored at 4° C. until purification. Removed supernatant was replaced with fresh production medium. ExpressPAGE of all harvests confirmed the presence of bands corresponding hROR2.

For purification, filtered supernatant was loaded onto a column suitable for binding strep tags; purification and elution was performed according to the manufacturer's protocol on an AEKTA pure (GE Healthcare). Fractions were analyzed for protein purity and integrity by SDS-PAGE. Protein-containing fractions were mixed and subjected to buffer exchange using Amicon filtration units (Millipore, Schaflhausen, Switzerland, UFC901008) to reach a dilution of ≥1:100 in PBS, and then sterile filtered using a low retention filter (0.20 µm, Carl Roth, Karlsruhe. Germany, PA 49.1).

H2L2 mouse immunization with hROR2-TwinStrep. Five transgenic humanized H2L2 mice (obtained from Harbour Biomed; H2L2 mice are a cross of the following mouse strains. F129, fvb/n and C57BL6, and on immunization produce antibodies with a human variable domain and a rat constant domain, disclosed in WO 2010/070263 A1), aged 6-10 weeks, were each immunized by two intraperitoneal (IP) injections followed by one intravenous injection of 100 µL of hROR2-TwinStrep (from Example 1), formulated as per Table 5.

TABLE 5

H2L2 mouse immunization schedule

| Day | hROR2-Twin Strep quantity | Formulation | Injected volume |
|---|---|---|---|
| 0 | 50 µg | 20 µg monophosphoryl lipid (MPLA, Sigma tlrl-mpls) and a 50:50 by volume mixture of Addavax adjuvant (Sigma, vac-adx-10) in PBS to reach 100 µL | 100 µL |
| 21 | 20 µg | 20 µg monophosphoryl lipid (MPLA, Sigma tlrl-mpls) and a 50:50 by volume mixture of Addavax adjuvant (Sigma, vac-adx-10) in PBS to reach 100 µL | 100 µL |
| 42 | 10 µg | PBS | 100 µL |

Blood samples were collected from each mouse by tail bleed on days: −7, 7 and 28 relative to the first injection, and by heart puncture on day 49. All procedures herein described involving animals were compliant with Swiss guidelines on animal care and handling.

Figure 2:
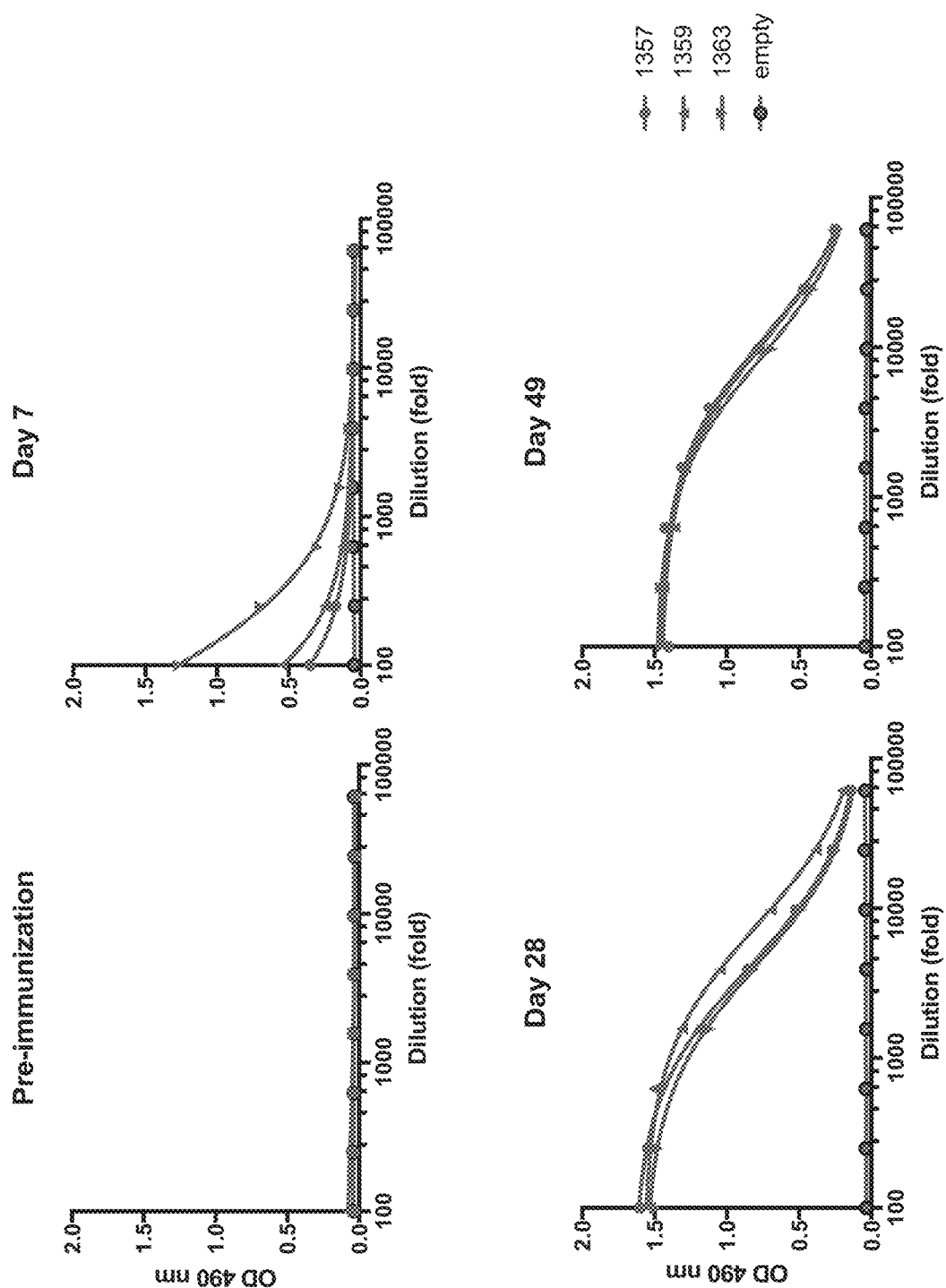
FIG. 2, anti-hROR2-ECD antibody titer detection following immunization of H2L2 mice referred to as 1357, 1368 and 1359 with ECD-hROR2-TwinStrep. Data for pre-immunization, and on days 7, 28 and 49 following initial immunization are shown.

Determination of antibody titers. Collected blood samples were incubated at room temperature for 15-60 minutes to allow clotting of the blood and subsequently centrifuged to obtain serum, in which antibody titers were evaluated. For this, ELISA plates were coated with 100 µL of 2 µg/ml hROR2-TwinStrep (from Example 1) in sodium bicarbonate coating buffer (0.1 M $Na_2CO_3$, 0.1M $NaHCO_3$, pH 9.6). Following 1-day incubation at 4° C., plates were washed with PBS supplemented with 0.05% (v/v) of Tween 20 and blocked with 150 µL of PBS supplemented with 0.05% (v/v) of Tween 20 and 3% of bovine serum albumin (BSA). Serum samples were diluted 100-fold, and a 2.5-fold dilution series prepared therefrom, adding 50 µL of each dilution to respective ELISA plate wells. Following 1 h incubation at 37° C., plates were washed with PBS supplemented with 0.05% (v/v) of Tween 20 before addition of HRP-conjugated anti-rat FC gamma fragment (Jackson Immunoresearch, 112-036-071). Following further plate washing, plates were developed with 50 µL of Sigmafast OPD Tablet set (Sigma. P9187) and the reaction stopped by addition of 2M sulfuric acid. Plates were read on an ELISA plate reader (OD 490), with results given in FIG. 2.

MACS isolation of hROR2 antigen specific B-cells from H2L2 mice. Mice were euthanized at 49-days following initial antigen injection, and mouse spleens were harvested. Spleens were transferred into a gentleMACS C-tube (cat. Nr. 130-093-237) containing 2.4 ml RPMI-10% FCS, and homogenized using the gentleMACS Octo Dissociator (Miltenyi Biotec) prior to filtration through a cell strainer (FACS tubes, BD Flacon, 734-0001) to get single cell suspensions.

Anti-hROR2-specific B cells from mouse splenocytes were then selected by MACS sorting: first, B cells were isolated using a mouse Pan B Cell Isolation Kit, human (Miltenyi Biotec, 130-095-813) by negative selection. For this, splenocyte cells were washed and suspended in MACS buffer (2-4×10$^6$ cells in 600 µL) prior to addition of 2 µL of mouse IgG (ChromPure, Jackson Immunoresearch, cat. No. 015-000-003, at 20 µg/mL), incubating on ice for 15 min. Cells were washed and re-suspended in 40 µL of cold MACS buffer. Non-B cells were magnetically-labeled by addition of 10 µL of Pan B cell Biotin Antibody Cocktail at 4° C., followed by 30 µL of cold MACS buffer and 20 µL of Anti-Biotin Microbeads. The final volume was adjusted to 500 µL with cold MACS buffer.

Non-B cells were removed by passing the cell suspension through an LD column (Miltenyi Biotec, 130-042-901) in a magnetic field using the QuadroMACS™ Separator (Miltenyi Biotec, 130-091-051), collecting flow through.

In parallel, hROR2-TwinStrep (12 µg, from Example 1) was incubated with Strep-Tactin Magnetic Nanobeads (IBA 6-5500-005, 50 µL at 7.044 mg/mL) and MACS buffer at 4° C., and loaded onto an LS column (Miltenyi Biotec, 130-042401) in a magnetic field to wash off unbound antigen. Antigen-loaded beads were then resuspended with the LD-column flow through (containing the B cells) and incubated 45 min on ice. After centrifugation and washing with MACS buffer, the mixture was placed in an LS column, washing under a magnetic field. Cells subsequently washed off the beads outside of the magnetic field are antigen-positive B cells.

Antibody cDNA library generation. Antigen-positive B cells were re-suspended in 500 µL TRI Reagent; 100 µL of chloroform was added following 5 min incubation. After vortex application and centrifugation, the clear upper phase was transferred to an Eppendorf tube, to which 1 µL of glycogen and 250 µL isopropanol were added. Following mixing, incubation, washing and centrifugation, supernatant was removed by decanting and 500 µL of ice-cold ethanol (75%) were added to the RNA pellet, mixing by inverting. The RNA pellet was then centrifuged and the supernatant decanted before air-drying.

RNA was reverse transcribed to cDNA using standard techniques. Variable domains were amplified in a PCR cycler with human primers in two steps: a first set of primers, as per Table 6, (a) complemented the 5' end of the variable domain, with inclusion of an upstream nucleotide sequence corresponding to part of a leader peptide, and (b) complemented the 5' end of the rat constant domain. A second set of primers included: (a) to complement the 5' end, nucleotide sequences allowing production of the full leader peptide, as well as the NotI restriction site: (b) to amplify the fully-human variable domain relative to the 3' end, using nucleotide sequence binding to the very 3' end of the J-domain, as well as NheI or BsiWI restriction sites for IgG and IgM, or IgK, respectively.

TABLE 6

Primers used or cDNA library generation.

| Primer name | Sequence | Reference |
|---|---|---|
| 1$^{st}$ step PCR IgG and IgM forward primer set | | |
| huVH4B-3'Leader-FR1 | CAGGTGCAGCTGCAGGAGTCSG | Sblattero and |
| huVH5B-3'Leader-FR1 | CAGGTACAGCTGCAGCAGTCA | Bradbury 1998 |
| huVH6B-3'Leader-FR1 | CAGGTGCAGCTACAGCAGTGGG | |
| huVH10Ba-3'Leader-FR1 | GAGGTGCAGCTGKTGGAGWCT | |
| huVH10Bb-3'Leader-FR1 | GAGGTGCAGCTGKTGGAGWCC | |
| huVH12B-3'Leader-FR1 | CAGGTCCAGCTKGTRCAGTCTGG | |
| huVH14B-3'Leader-FR1 | CAGRTCACCTTGAAGGAGTCTG | |
| huVH22B-3'Leader-FR1 | CAGGTGCAGCTGGTGSARTCTGG | |
| 1$^{st}$ step PCR IgG reverse primer | | |
| rat_IgG12abc_R | CAGGGTGACTGAGGGCGTAG | developed in house |
| 1$^{st}$ step PCR IgM reverse primer | | |
| rat_IgM_R | GTTGGGAAGGTTCTGACACC | developed in house |
| 1$^{st}$ step PCR IgK forward primer set | | |
| hu5'VK1-5_3'Leader-FR1 | GACATCCAGATGACCCAGTC | Tiller et al. 2008 |
| hu5'VK1-9_3'Leader-FR1 | GACATCCAGTTGACCCAGTCT | |
| hu5'VK1D-43_3'Leader-FR1 | GCCATCCGGATGACCCAGTC | |
| hu5'VK2-24_3'Leader-FR1 | GATATTGTGATGACCCAGAC | |
| hu5'VK2-28_3'Leader-FR1 | GATATTGTGATGACTCAGTC | |
| hu5'VK2-30_3'Leader-FR1 | GATGTTGTGATGACTCAGTC | |
| hu5'VK3-11_3'Leader-FR1 | GAAATTGTGTTGACACAGTC | |

TABLE 6-continued

Primers used or cDNA library generation.

| Primer name | Sequence | Reference |
|---|---|---|
| hu5'VK3-15_3'Leader-FR1 | GAAATAGTGATGACGCAGTC | |
| hu5'VK3-20_3'Leader-FR1 | GAAATTGTGTTGACGCAGTCT | |
| hu5'VK4-1_3'Leader-FR1 | GACATCGTGATGACCCAGTC | |
| *1st step PCR IgK reverse primer* | | |
| rat_CK_R | CTTGACACTGATGTCTCTGGG | developed in house |
| *2nd step PCR IgG and IgM reverse primer set* | | |
| hu3'_JH1245_NheI | TGAGGAGACGGTGACCAG | Tiller et al. 2008 |
| hu3'_JH3_NheI | TGAAGAGACGGTGACCATTG | |
| hu3'_JH6_NheI | TGAGGAGACGGTGACCGTG | |
| *2nd step PCR IgK reverse primer set* | | |
| huHSCJK2o-B_BsiWI | TTTGATCTCCAGCTTGGTCCC | Berry et al., 2003 |
| huHSCJK3o-B_BsiWI | TTTOATATCCACTTTGGTCCC | |
| huHSCJK5o-B_BsiWI | TTTAATCTCCAGTCGTGTCCC | |
| huHSCJK14O-B_BsiWI | TTTGATYTCCACCTTGGTCCC | |

Transposition-mediated generation of cellular libraries and library characterization. Antibody variable-domain encoding cDNA's were then cloned into vectors via the encoded restriction sites alongside nucleotides encoding the human constant domains, and between nucleotides encoding sequences functional with PiggyBac transposase, as well as ampicillin resistance. The library was characterized by Miniprep followed by sequencing. The library consisted of $6 \times 10^6$ to $5 \times 10^7$ members.

These were co-transfected into 63-12 murine A-MuLV transformed preB-cells with a second vector encoding the PiggyiBac transposase for transposition-mediated B-cell surface display and secretion of antibodies ("Transpo-mAb Display"), as described in Waidmeier et al., 2016.

Figure 3:
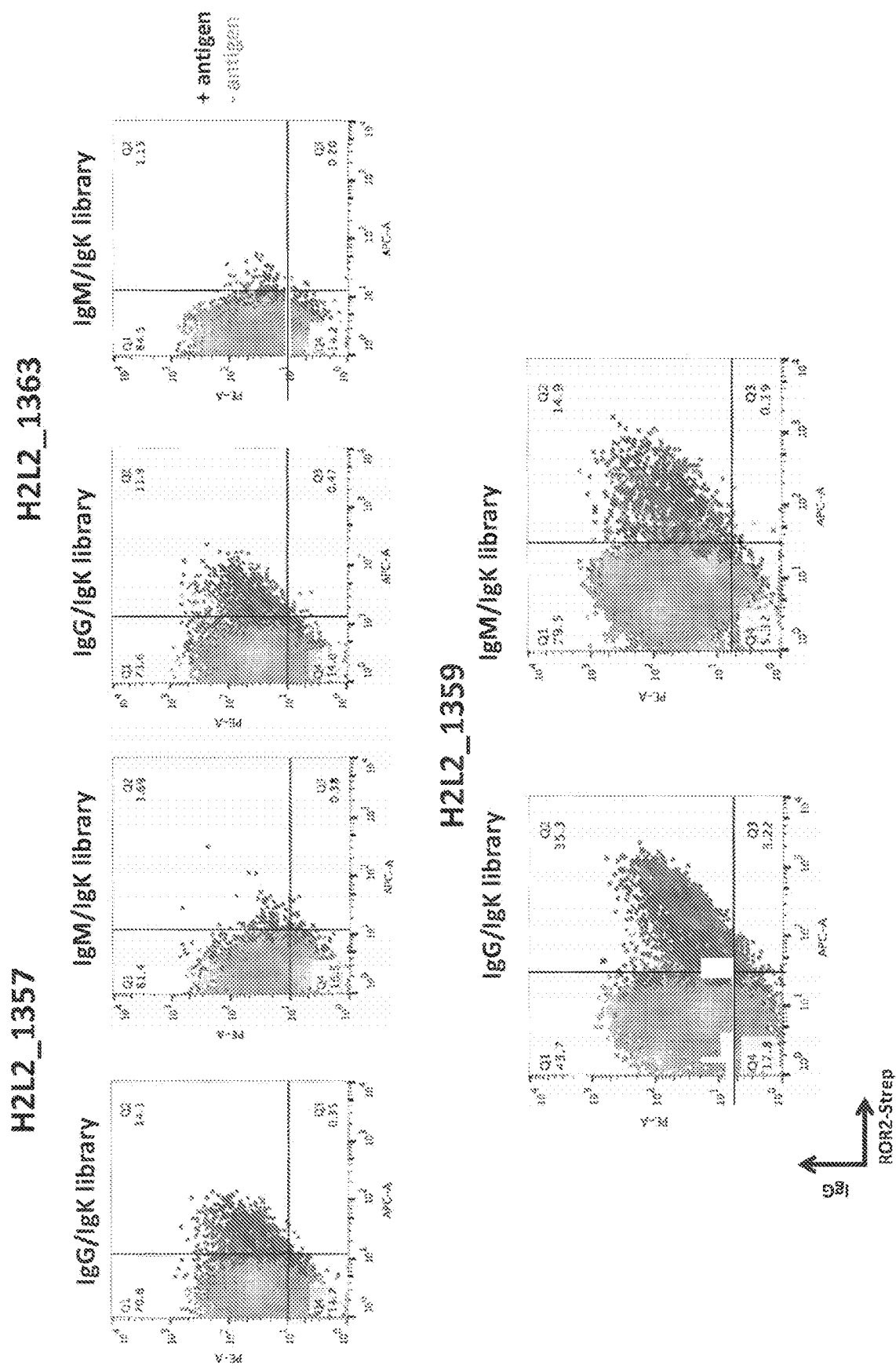
FIG. 3. Antigen-specific FACS sorting per mouse based on IgG/IgK and IgM/IgK libraries for H2L2 mouse 1357, H2L2 mouse 1363 and H2L2 mouse 1359.

Functional screening of clone supernatants and clone selection. B cells were single-cell FACS sorted with aFACSAria, and selected based on double-positive staining with an anti-Strep tag antibody (IBA, 2-1555-050) and a polyclonal anti-IgG-PE (ebioscience, 12-4998-82); up to 288 clones per IgG/IgK and IgM/IgK library per mouse were selected and grown in SF-IMDM Medium with 2% (v/v) Fetal Calf Serum (FCS), 100 IU/mL of Pen-Strep-Fungizone, 50 µM Beta-Mercaptoethanol and 2 mM L-glutamine (all Bioconcept. Allschwil, Switzerland)) at 37° C. and 7.5% $CO_2$ (FIG. 3). Antibodies in selected B-cell clone supernatants were then evaluated by two means: (1) for hROR2 binding by ELISA, and (2) for mediating killing of hROR2-overexpressing EMT-6 cells following hROR2 binding, using a secondary ADC binding to anti-ROR2 antibodies.

hROR2 binding by one-spot ELISA Half of the wells of 96-well plates were coated with 50 µL of 2 µg/mL of anti-human Fc (Jackson Immunoresearch, 109-006-008), and the other half with 50 µL of 2 µg/mL of hROR2-Twin-Strep (from Example 1), both in coating buffer (0.1M $Na_2CO_3$, 0.1M $NaHCO_3$, pH 9.6), and stored overnight at 4° C. After blocking each well with addition of 150 µL of PBS supplemented with 0.05% (v/v) of Tween 20 and 3% (w/v) bovine serum albumin (BSA) for 1 h at 37° C., 50 µL of diluted supernatants (diluted 5-fold in PBS supplemented with 1% (w/v) bovine serum albumin (BSA) and 0.05% (v/v) of Tween 20) were added to each well. For comparison, a serial 1:20 dilution of a purified anti-ROR2-antibody as well as an isotype control antibody starting at 0.5 µg/ml in PBS supplemented with 1% (w/v) bovine serum albumin (BSA) and 0.05% (v/v) of Tween 20 was added per plate. Following 1 h incubation at 37° C., plates were washed with PBS supplemented with 0.05% (v/v) of Tween 20 before addition of HRP-conjugated anti-human IgG (Jackson Immunoresearch, 109-036-008). Following further plate washing, plates were developed with 50 µL of Sigmafast OPD Tablet set (Sigma, P9187) and the reaction stopped by addition of 2M sulfuric acid. Plates were read on an ELISA plate reader (OD 490).

One-spot secondary killing assay: EMT6 cells engineered to overexpress hROR2 of Example 7 were plated at 1000 cells per 100 µl per well in DMEM complete (Dulbecco's Modified Eagle Medium (DMEM) High Glucose (4.5 g/L) with L-Glutamine with 10% (v/v) Fetal Calf Serum (FCS), 100 IU/mL of Pen-Strep-Fungizone and 2 mM L-glutamine (all Bioconcept, Allschwil, Switzerland)) and incubated at 37° C. and 5% $CO_2$. The following day, 15 µl undiluted supernatant or 15p of a 2-fold serial dilution of a purified anti-ROR2 antibody starting at 10 µg/ml were added to the cells. Following incubation for 30 min, 35 µl of anti-hu-IgG-CL-PNU (Moradec, AH-102PN-50) was added at 0.32 µg/ml. After an additional three days, plates were removed from the incubator and equilibrated to room temperature. After approximately 30 min, 50 µL was removed from each well, and then 50 µL of CellTiter-Glo® 2.0 Luminescent Solution (Promega. G9243) was added to each well. After shaking the plates at 750 rpm for 5 min followed by 20 min incubation without shaking, luminescence was measured on a Spark 10M plate reader with an integration time of 1 second per well.

Antibodies showing high ROR2-binding as well as low cell viability, thereby indicating being a good ADC candidate, were further analyzed in titrated ELISA and cell viability assays. In the titrated ELISA, the same set-up as described above in the one-spot ELISA was used, with the exception that the 5-fold diluted supernatant was serially diluted 3-fold for 8 wells total. In the titrated secondary killing assay, a similar set-up as described above was used. Here, IgG concentrations of all supernatants were adjusted to the IgG concentration of the lowest expressor (as measured by the titrated ELISA when coating with anti-IgG). From this concentration, all supernatants were serially diluted 2-fold for 6 dilutions total and thereof 15 µl were added to the plate. Analysis was performed using Graphpad Prism Software.

Example 2: Anti-ROR2 Antibody Expression and Purification

Expression vectors: Antibody sequences determined above to bind hROR2 were synthesized as DNA by GenScript (Piscataway, USA) and included within an expression vector containing suitable restriction sites and the appropriate constant domain.

Expression and purification of anti-ROR2 antibodies: Expression vectors were transfected into HEK293T cells using Lipofectamine® LTX Reagent with PLUS™ Reagent (Thermo Fisher Scientific, Reinach, Switzerland, 15388100); following a 1-day incubation (37° C., 5% $CO_2$, growth media: Dulbecco's Modified Eagle Medium (DMEM) High Glucose (4.5 g/L) with L-Glutamine with 10% (v/v) Fetal Calf Serum (FCS), 100 IU/mL of Pen-Strep-Fungizone and 2 mM L-glutamine (all Bioconcept, Allschwil, Switzerland)), cells were expanded under selection conditions (2 µg/mL of puromycin (Sigma-Aldrich. Buchs S G, Switzerland. P8833-25 mg stock at 2 mg/mL)). Cells were split and further expanded (37° C., 5% $CO_2$); once confluency was reached, tissue culture dishes were coated with 20 µg/ml poly-L-Lysine (Sigma-Aldrich, P1524) for 2 h at 37° C. and washed twice with PBS. Then, cells were trypsinized and split 1:3 onto poly-L-lysine-coated plates. Again after reaching confluency, cells were washed with PBS followed by media replacement to production media (DMEM/F-12, Gibco/Thermo Fisher Scientific, 31330-03) supplemented with 1 µg/mL puromycin (Sigma. P8833), 100 IU/mL of Pen-Strep-Fungizone (Bioconcept), 161 µg/mL of N-acetyl-L-cysteine (Sigma-Aldrich, A8199) and 10 µg/mL of L-glutathione reduced (Sigma-Aldrich, G6529). Supernatant, harvested bi-weekly and filtered (0.22 µm) to remove cells, was stored at 4° C. until purification.

For purification, filtered supernatant was loaded onto a PBS-equilibrated Protein A HiTrap column (GE Healthcare, Frankfurt am Main, Germany, 17-0405-01) or a JSR Amsphere™ Protein A column (JSR Life Sciences, Leuven, Belgium, JWT203CE) and washed with PBS: elution was performed using 0.1M glycine (pH 2.5) on an AEKTA pure (GE Healthcare). Fractions were immediately neutralized with 1 M Tris-HCl buffer (pH 8.0), and analyzed for protein purity and integrity by SDS-PAGE. Protein-containing fractions were mixed and subjected to buffer exchange using Amicon filtration units (Millipore, Schaffhausen, Switzerland, UFC901008) to reach a dilution of 1:100, and then sterile filtered using a low retention filter (0.20 µm, Carl Roth, Karlsruhe, Germany, PA 49.1).

The purity and integrity of the recombinant antibodies was analyzed by SDS-PAGE.

TABLE 7

Sequences of prior art anti-hROR1 isotype control antibody XBR1-402 and anti-CD30 isotype control antibody Ac10, with the constant domain underlined

| SEQ ID NO. | Amino Acid Sequence (with constant domain underlined) |
| --- | --- |
| SEQ ID NO. 131 XBR1-402 HC amino acid sequence | QEQQKESGGGLFKPTDTLTLTCTASGFDISSYYMSWVRQAPGNGLEWIGAIGI SGNAYYASWAKSRSTITRNTNLNTVTLKMTSLTAADTATYFCARDHPTYGMDL WGPGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCLVKG FYPSDIAVEWESNGQPENNYKTTPPVLDSDGSFPLYSKLTVDKSRWQQGNVFS CSVMHEALHNHYTQKSLSLSPGK |
| SEQ ID NO. 132 XBR1-402 LC amino acid sequence | SYELTQLPSVSVSLGQTARITCEGNNIGSKAVHWYQQKPGLAPGLLIYDDDER PSGVPDRFSGSNSGDTATLTISGAQAGDEADYYCQVWDSSAYVFGGGTQLTVT GQPKAAPSVTLFPPSSEELQANKATLVCLISDFYPGAVTVAWKADSSPVKAGV ETTTPSKQSNNKYAASSYLSLTPEQWKSHKSYSCQVTHEGSTVEKTVAPTECS |
| SEQ ID NO. 133 Ac10 HC amino acid secpence | QIQLQQSGPEVVKPGASVKISCKASGYTFTDYYITWVKQKPGQGLEWIGWIYP GSGNTKYNEKFKGKATLTVDTSSSTAFMQLSSLTSEDTAVYFCANYGNYWFAY WGQGTQVTVSAASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWLNGKE YKCKVSNKALPAPIEKTISKAKGQPREPQVYTLPPSRDELTKNQVSLTCLVKG FYPSDIAVEWESNGQPENNYKTTPPVLDSDGSFFLYSKLTVDKSRWQQGNVFS CSVMHEALHNHYTQKSLSLSPGK |
| SEQ ID NO. 134 Ac10 LC amino acid sequence | DIVLTQSPASLAVSLGQRATISCKASQSVDFDGDSYMNWYQQKPGQPPKVLIY AASNLESGIPARFSGSGSGTDFTLNIHPVEEEDAATYYCQQSNEDPWTFGGGT KLEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC |

Table 8 lists the protocols used for expression and purification of antibody batches used in the subsequent examples, along with their final concentration and buffer.

TABLE 8

Protocols and concentrations of mAbs used in the Examples

| Antibody (ref.) | Antibody SEQ ID HC/LC | C-Terminal Tags (HC: Heavy Chain, LC: Light Chain) | Buffer | Final concentration (mg/mL) |
|---|---|---|---|---|
| GK-1E5 (mAb270) | HC: SEQ ID NO. 6<br>LC: SEQ ID NO. 7 | HC: LPETG-Strep<br>LC: G$_5$SLPETG-Strep | PBS | 1.27 |
| GK-5A1 (mAb271) | HC: SEQ ID NO. 8<br>LC: SEQ ID NO. 9 | HC: LPETG-Strep<br>LC: G$_5$SLPETG-Strep | PBS | 4.5 |
| MK-3B12 (mAb272) | HC: SEQ ID NO. 2<br>LC: SEQ ID NO. 3 | HC: LPETG-Strep<br>LC: G$_5$SLPETG-Strep | PBS | 3.1 |
| GK-2G8 (mAb273) | HC: SEQ ID NO. 10<br>LC: SEQ ID NO. 11 | HC: LPETG-Strep<br>LC: G$_5$SLPETG-Strep | PBS | 0.3 |
| GK-6B10 (mAb279) | HC: SEQ ID NO. 14<br>LC: SEQ ID NO. 15 | HC: LPETG-Strep<br>LC: G$_5$SLPETG-Strep | PBS | 1.6 |
| GK-5E1 (mAb280) | HC: SEQ ID NO. 12<br>LC: SEQ ID NO. 13 | HC: LPETG-Strep<br>LC: G$_5$SLPETG-Strep | PBS | 2.6 |
| GK-5G12 (mAb281) | HC: SEQ ID NO. 16<br>LC: SEQ ID NO. 17 | HC: LPETG-Strep<br>LC: G$_5$SLPETG-Strep | PBS | 1.4 |
| MK-7C3 (mAb282) | HC: SEQ ID NO. 4<br>LC: SEQ ID NO. 5 | HC: LPETG-Strep<br>LC: G$_5$SLPETG-Strep | PBS | 1.3 |
| MK-3B12 (mAb328) | HC: SEQ ID NO. 2<br>LC: SEQ ID NO. 3 | HC: LPETG-TwinStrep<br>LC: G$_5$SLPETG-TwinStrep | PBS | 3.5 |
| GK-21D3 (mAb399) | HC: SEQ ID NO. 18<br>LC: SEQ ID NO. 19 | HC: LPETG-TwinStrep<br>LC: G$_5$SLPETG-TwinStrep | PBS | 0.9 |
| GK-21D3 (mAb417) | HC: SEQ ID NO. 18<br>LC: SEQ ID NO. 19 | HC: LPETG-TwinStrep<br>LC: G$_5$SLPETG-TwinStrep | PBS | 1.8 |
| MK-24C10 (mAb396) | HC: SEQ ID NO. 20<br>LC: SEQ ID NO. 21 | HC: LPETG-TwinStrep<br>LC: G$_5$SLPETG-TwinStrep | PBS | 6.3 |
| MK-24C10 (mAb428) | HC: SEQ ID NO. 20<br>LC: SEQ ID NO. 21 | HC: LPETG-TwinStrep<br>LC: G$_5$LPETG-TwinStrep | PBS | 2.4 |
| MK-24F9 (mAb416) | HC: SEQ ID NO. 22<br>LC: SEQ ID NO. 23 | HC: LPETG-TwinStrep<br>LC: G$_5$SLPETG-TwinStrep | PBS | 4.7 |
| GK-22G12 (mAb409) | HC: SEQ ID NO. 24<br>LC: SEQ ID NO. 25 | HC: LPETG-TwinStrep<br>LC: G$_5$SLPETG-TwinStrep | PBS | 3.0 |
| GK-22G12 (mAb418) | HC: SEQ ID NO. 24<br>LC: SEQ ID NO. 25 | HC: LPETG-TwinStrep<br>LC: G$_5$LPETG-TwinStrep | PBS | 3.0 |
| XBR1-402 (mAb003) | HC: SEQ ID NO. 71<br>LC: SEQ ID NO. 72 | HC: LPETG-Strep<br>LC: G$_5$SLPETG-Strep | PBS | 6.0 |
| Ac10 (mAb046) | HC: SEQ ID NO. 73<br>LC: SEQ ID NO. 74 | HC: LPETG-Strep<br>LC: G$_5$SLPETG-Strep | PBS | 7.9 |

Example 3: Antibody Binding to hROR2 by SPR

Surface plasmon resonance for the measurement of the affinities of anti-hROR2 antibodies to hROR2 was performed on a Biacore T200 instrument (GE Healthcare). Antibodies were captured using a CM5 Protein A sensor chip (GE Healthcare, 29127556) or Protein G was immobilized on a CM5 sensor chip. For affinity measurements, either purified anti-hROR2 antibodies or 293T supernatants containing anti-hROR2 antibodies were used. In all cases, anti-hROR2 antibodies were diluted to 1-3 μg/mL in 1×HBS-EP+ running buffer (10 mM HEPES, 150 mM NaCl, 3 mM EDTA (pH 7.4), and 0.05% (v/v) Tween 20) and captured for 30 s with a flow of 3 μL/min. hROR2-TwinStrep (from Example 1) was diluted in running buffer using 2-fold serial dilutions ranging from 40 nM to 2.5 nM.

Figure 4:
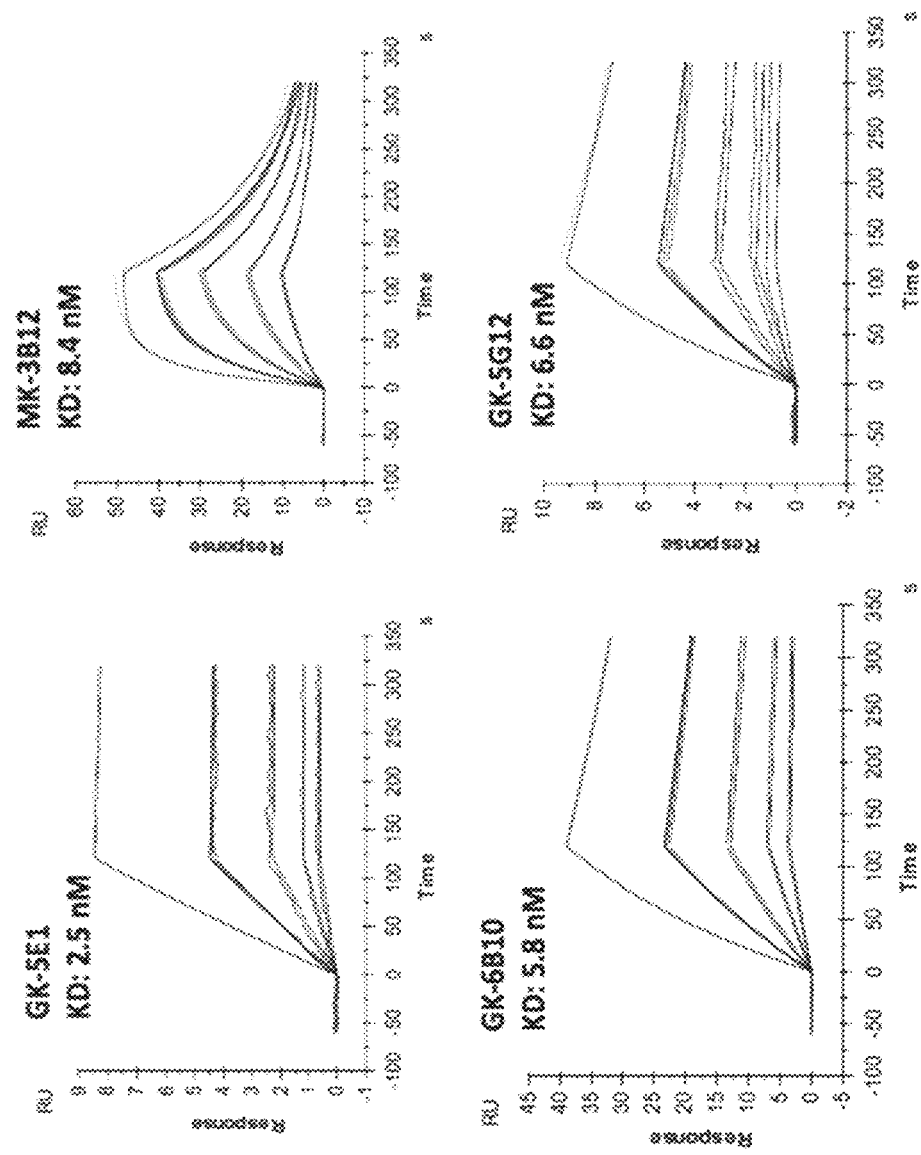
FIG. 4. Determination of binding affinities of individual monoclonal antibodies cloned and recombinantly expressed, as indicate, to hROR2-ECD as measured by surface plasmon resonance (SPR).
Figure 4:
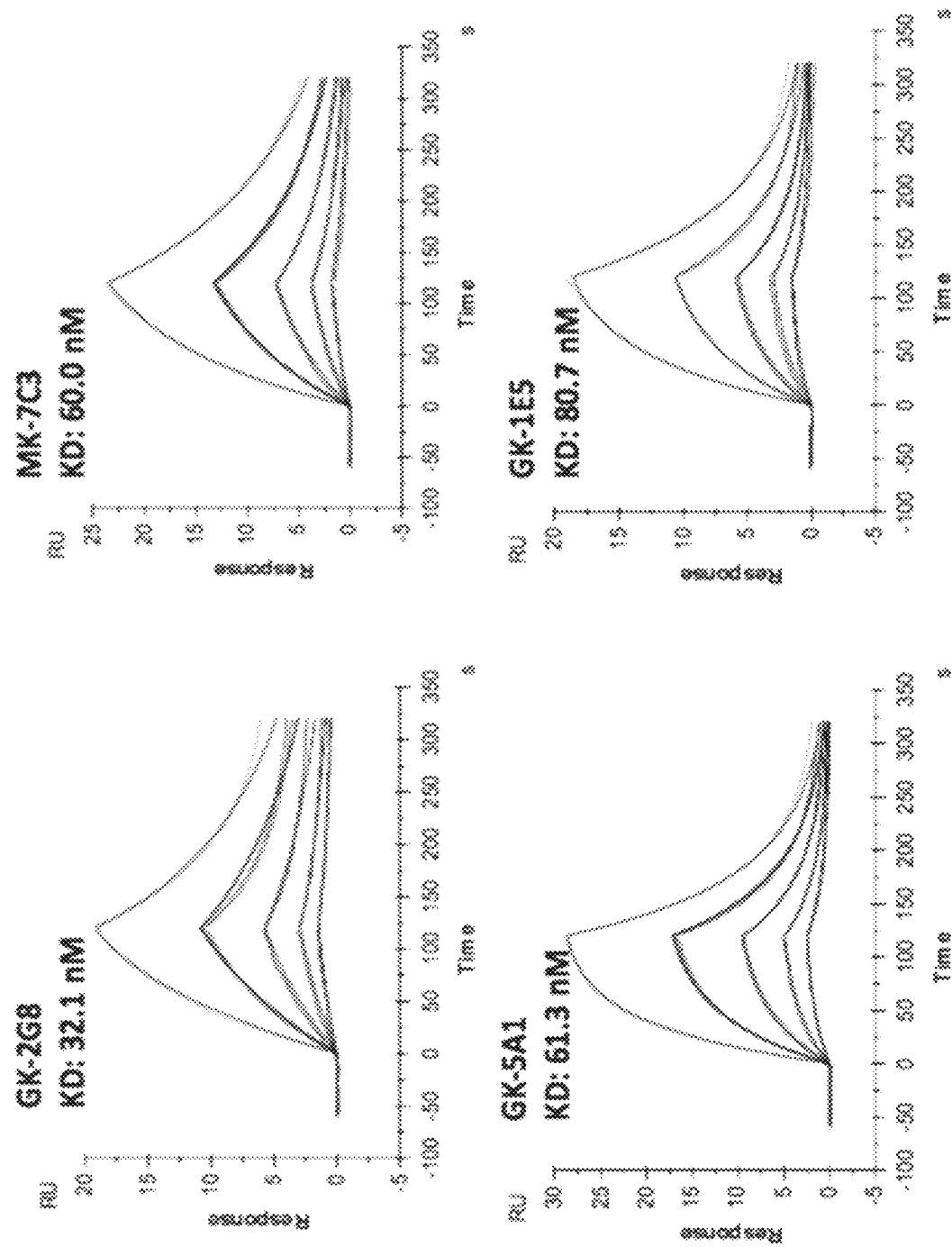

Association and dissociation were measured at a flow of 30 μL/min for 120 s and 200 s, respectively. Calculation of association ($k_{on}$) and dissociation ($k_{off}$) rate constants was based on a 1:1 Langmuir binding model. The equilibrium dissociation constant ($K_d$) was calculated from $k_{off}/k_{on}$. SPR sensorgrams for the antibodies of Table 9 are shown in FIG. 4, with $K_d$, $k_{on}$ and $k_{off}$ values reported in Table 9.

TABLE 9

Binding characteristics of anti-ROR2 antibodies as determined by SPR

| Antibody | $k_{on}$ (M$^{-1}$s$^{-1}$) | $k_{off}$ (s$^{-1}$) | $K_d$ (nM) |
|---|---|---|---|
| GK-1E5 (mAb270) | 4.83 × 10$^4$ | 1.23 × 10$^{-4}$ | 2.5 |
| GK-5A1 (mAb271) | 4.32 × 10$^5$ | 2.65 × 10$^{-2}$ | 68.4 |
| MK-3B12 (mAb272) | 1.21 × 10$^6$ | 1.02 × 10$^{-2}$ | 8.4 |
| MK-7C3 (mAb273) | 1.53 × 10$^5$ | 9.16 × 10$^{-3}$ | 60.0 |
| GK-2G8 (mAb279) | 8.93 × 10$^5$ | 2.86 × 10$^{-2}$ | 32.1 |
| GK-6B10 (mAb280) | 1.72 × 10$^5$ | 1.00 × 10$^{-3}$ | 5.8 |
| GK-5E1 (mAb281) | 1.82 × 10$^5$ | 1.47 × 10$^{-2}$ | 80.7 |
| GK-5G12 (mAb282) | 1.69 × 10$^5$ | 1.11 × 10$^{-3}$ | 6.6 |
| GK-21D3 (mAb399) | 6.55 × 10$^4$ | 2.28 × 10$^{-2}$ | 347 |
| MK-24C10 (mAb396) | 4.17 × 10$^5$ | 8.93 × 10$^{-3}$ | 21.4 |
| MK-24F9 (mAb416) | 3.88 × 10$^5$ | 4.65 × 10$^{-4}$ | 1.2 |
| GK-22G12 (mAb409) | 6.03 × 10$^5$ | 4.03 × 10$^{-4}$ | 0.7 |

Example 4: Expression of Mouse and Cynomolgus ROR2

Mouse ROR2 (mROR2) and cynomolgus ROR2 (cROR2) were each expressed according to an analogous protocol as given for hROR2 expression in Example 1.

Example 5: Cross-Reactivity of mAbs with Mouse and Cynomolgus ROR2

Binding of antibodies to hROR2, mouse ROR2 (mROR2) and cynomolgus ROR2 (cROR2) was evaluated in an ELISA-based assay. For this, ELISA plates were coated with 50 μL of 2 μg/ml, in sodium bicarbonate coating buffer (0.1M $Na_2CO_3$, 0.1M $NaHCO_3$, pH 9.6), of: (a) an anti-human Fc (Jackson Immunoresearch, 109-006-098), (b) hROR2-TwinStrep, (c) cynomolgus ROR2-TwinStrep or (d) mouse ROR2-TwinStrep. Following 1-2-days incubation at 4° C., plates were washed with PBS supplemented with 0.05% (v/v) of Tween 20 and blocked with 150 μL of PBS supplemented with 0.05% (v/v) of Tween 20 and 3% of bovine serum albumin (BSA). Thereafter, 3-fold or 4-fold dilutions of purified antibodies starting at 0.5 or 2 μg/ml, respectively, in PBS supplemented with 1% (w/v) bovine serum albumin (BSA) and 0.05% (v/v) of Tween 20 were added. Following 1 h incubation at 37° C., plates were washed with PBS supplemented with 0.05% (v/v) of Tween 20 prior to addition of HRP-conjugated anti-human IgG (Jackson Immunoresearch, 109-036-008). Following further plate washing, plates were developed with 50 μL of Sigma-fast OPD Tablet set (Sigma, P9187) and the reaction stopped by addition of 2M sulfuric acid. Plates were read on an ELISA plate reader (OD 490).

Figure 5:
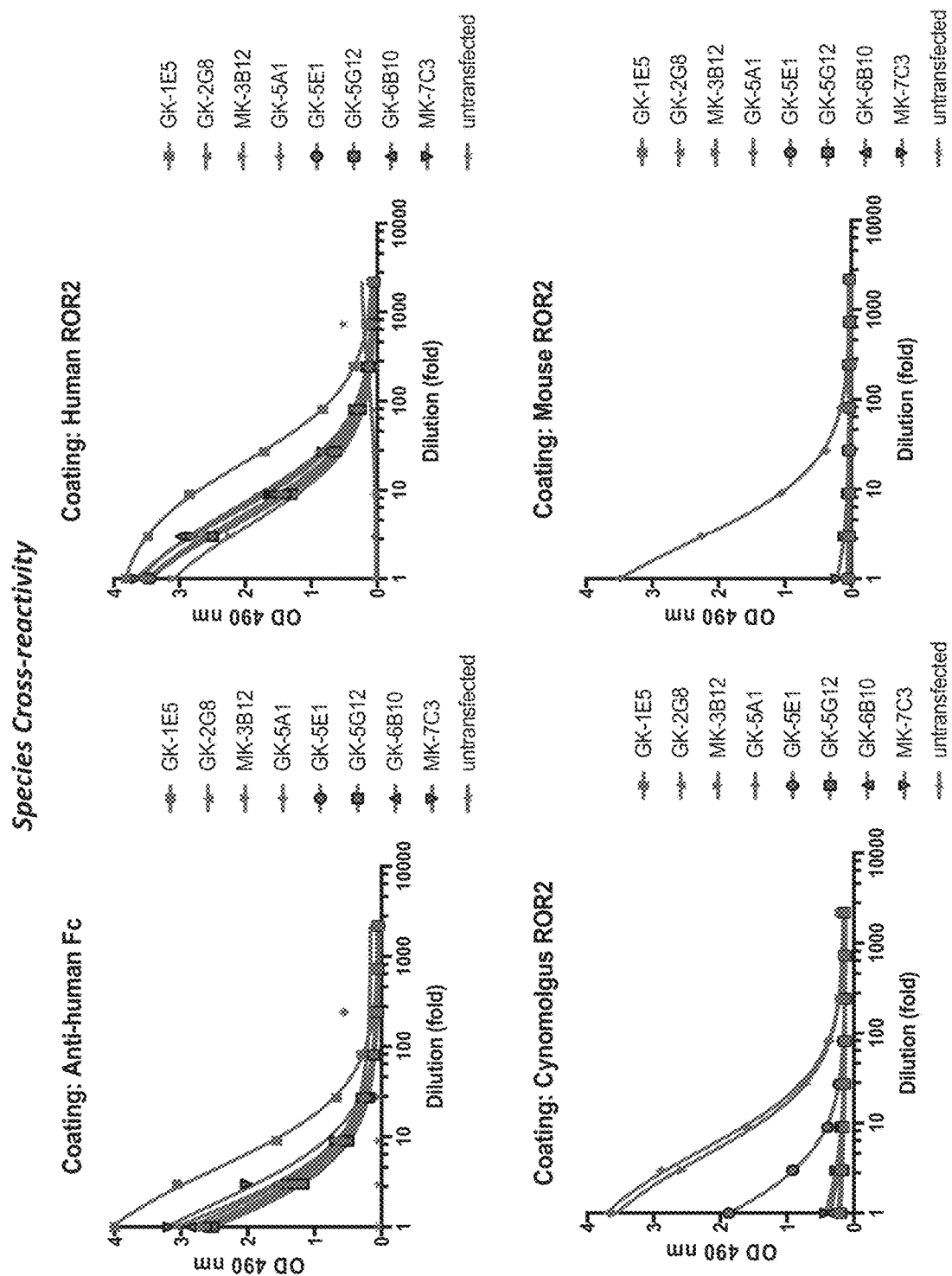
FIG. 5. Determination of species cross-reactivity of recombinant, monoclonal anti-hROR2 antibodies to mouse and cynomolgus ROR2 as evaluated by ELISA.
Figure 11:
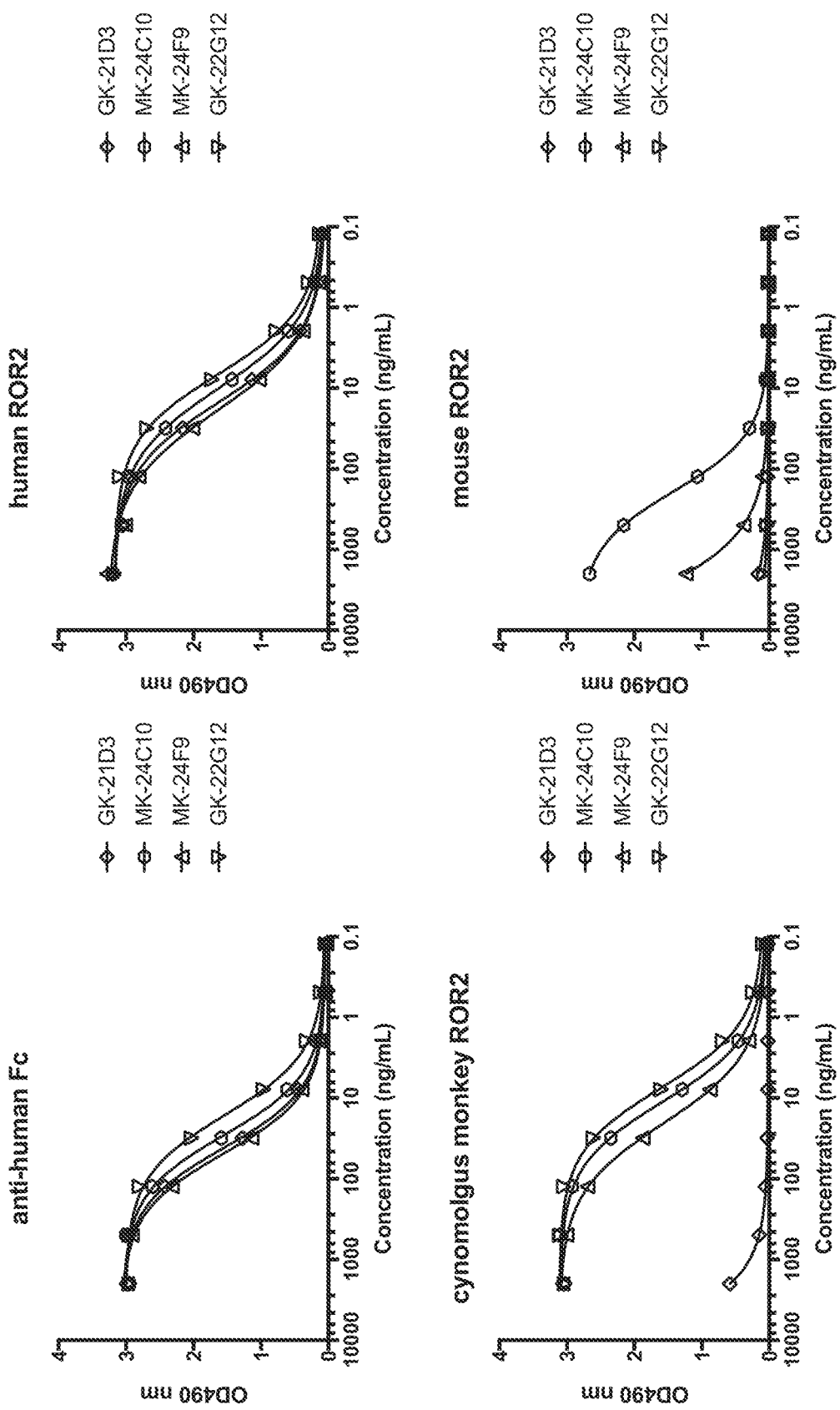
FIG. 11. Determination of species cross-reactivity of recombinant, monoclonal anti-hROR2 antibodies to mouse and cynomolgus ROR2 as evaluated by ELISA.

FIG. 5 and FIG. 11 show the ELISA profiles of the mAbs of Table 10. This table also summarizes the binding status of each mAb to ROR2 from each of the evaluated species.

TABLE 10

Results of ELISA-based evaluation of binding of mAbs to human ROR2 (hROR2), cynomolgus ROR2 (cROR2) and mouse ROR2 (mROR2)

| Antibody | hROR2 | cROR2 | mROR2 |
|---|---|---|---|
| GK-1E5 (mAb270) | Yes | No | No |
| GK-5A1 (mAb271) | Yes | Yes | Yes |
| MK-3B12 (mAb272) | Yes | Yes | No |
| MK-7C3 (mAb273) | Yes | No | No |
| GK-2G8 (mAb279) | Yes | No | No |
| GK-6B10 (mAb280) | Yes | No | No |
| GK-5E1 (mAb281) | Yes | Weak | No |
| GK-5G12 (mAb282) | Yes | No | No |
| GK-21D3 (mAb417) | Yes | Weak | No |
| MK-24C10 (mAb428) | Yes | Yes | Weak |
| MK-24F9 (mAb416) | Yes | Yes | Weak |
| GK-22G12 (mAb418) | Yes | Yes | No |

Example 6: Conjugation of mAbs with Glycine-Modified Toxins to Form ADCs Using SMAC-Technology™

Sortase A. Recombinant and affinity purified Sortase A enzyme from *Staphylococcus aureus* was produced in *E. coli* as disclosed in WO2014140317A1.

Figure 6:
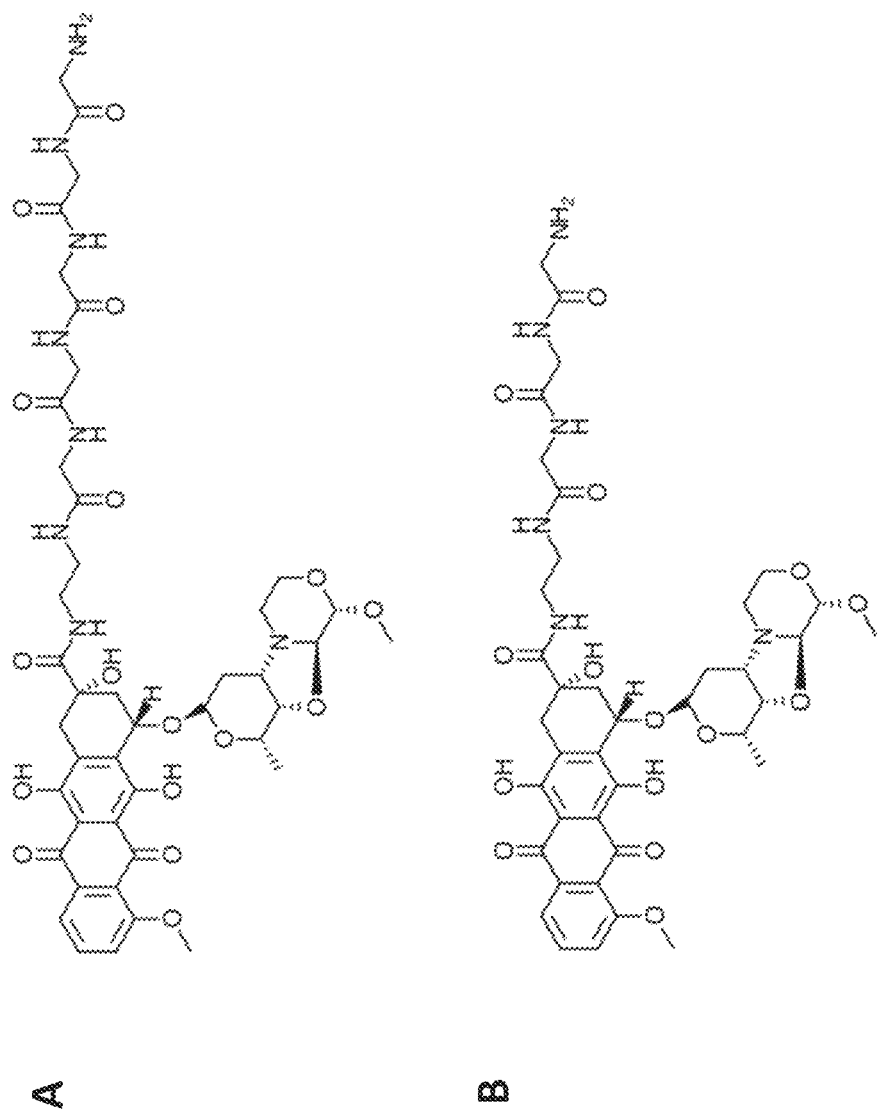
FIG. 6. (A) Chemical structures of pentaglycine-modified PNU derivative ("G5-PNU"), (B) triglycine-modified PNU derivative ("G3-PNU").

Generation of glycine-modified toxins. Pentaglycine-modified EDA-anthracycline derivative G5-PNU and triglycine-modified EDA-anthracycline derivative G3-PNU (FIGS. 6(A) and (B), respectively) were manufactured by Concortis, San Diego, U.S. The identity and the purity of the glycine-modified toxins were confirmed by mass-spectrometry and HPLC. Each of the glycine-modified toxins exhibited >95% purity, as determined by HPLC chromatography.

Sortase-mediated antibody conjugation. The above-mentioned toxins were conjugated to anti-ROR2 and comparative antibodies as per Table 7 by incubating LPETG-tagged mAbs [5-10 μM] with glycine-modified toxin [100-200 μM] and 2.5-3 μM Sortase A in the listed conjugation buffer for 3.5 h at 25° C. The reaction was stopped by passage through a BioRad Protein A GraviTrap column as per Table 11. Bound conjugate was eluted with 5 column volumes of elution buffer (0.1M glycine pH 2.5, 50 nM NaCl), with 1 column volume fractions collected into tubes containing 25% v/v 1M Tris-Base to neutralise the acid. Protein containing fractions were pooled and formulated in the formulation buffer of Table 11 using a ZebaSpin desalting column.

ADC analytics. DAR was assessed by Reverse Phase Chromatography performed on a Polymer Labs PLRP 2.1 mm×5 cm, 5 μm column run at 1 mL/min/80° C. with a 25 min linear gradient of 0.05 to 0.1% $TFA/H_2O$ and 0.04 to 0.1% $TFA/CH_3CN$. Samples were first reduced by incubation with DTT at pH 8.0 at 37° C. for 15 min. The DAR determined by Reverse Phase Chromatography is summarized in Table 7 below.

TABLE 11

Analytical summary of ADCs manufactured in this study. DAR, drug-to-antibody ratio, determined by reverse phase chromatography.

| ADC (ref.) | mAb (ref.) | Conjugation Buffer | Formulation Buffer | DAR |
|---|---|---|---|---|
| GK-1E5-G5-PNU (adc442) | GK-1E5 (mAb270) | 50 mM HEPES, pH 7.5, 1 mM $CaCl_2$, 10% Glycerol, 150 mM NaCl | PBS | ND |
| GK-5A1-G5-PNU (adc443) | GK-5A1 (mAb271) | 50 mM HEPES, pH 7.5, 1 mM $CaCl_2$, 10% Glycerol, 150 mM NaCl | PBS | ND |
| MK-3B12-G5-PNU (adc444) | MK-3B12 (mAb272) | 50 mM HEPES, pH 7.5, 1 mM $CaCl_2$, 10% Glycerol, 150 mM NaCl | PBS | ND |
| GK-2G8-G5-PNU (adc445) | GK-2G8 (mAb273) | 50 mM HEPES, pH 7.5, 1 mM $CaCl_2$, 10% Glycerol, 150 mM NaCl | PBS | 3.7 |
| GK-6B10-G5-PNU (adc446) | GK-6B10 (mAb279) | 50 mM HEPES, pH 7.5, 1 mM $CaCl_2$, 10% Glycerol, 150 mM NaCl | PBS | 3.6 |
| GK-5E1-G5-PNU (adc447) | GK-5E1 (mAb280) | 50 mM HEPES, pH 7.5, 1 mM $CaCl_2$, 10% Glycerol, 150 mM NaCl | PBS | 3.6 |

TABLE 11-continued

Analytical summary of ADCs manufactured in this study. DAR, drug-to-antibody ratio, determined by reverse phase chromatography.

| ADC (ref.) | mAb (ref.) | Conjugation Buffer | Formulation Buffer | DAR |
|---|---|---|---|---|
| GK-5G12-G5-PNU (adc448) | GK-5G12 (mAb281) | 50 mM HEPES, pH 7.5, 1 mM CaCl$_2$, 10% Glycerol, 150 mM NaCl | PBS | 3.8 |
| MK-7C3-G5-PNU (adc449) | MK-7C3 (mAb282) | 50 mM HEPES, pH 7.5, 1 mM CaCl$_2$, 10% Glycerol, 150 mM NaCl | PBS | ND |
| MK-3B12-G3-PNU (adc487) | MK-3B12 (mAb328) | 50 mM HEPES, pH 7.5, 1 mM CaCl$_2$, 10% Glycerol, 150 mM NaCl | PBS | 3.9 |
| GK-21D3-G5-PNU (adc701) | GK-21D3 (mAb399) | 50 mM HEPES, pH 7.5, 1 mM CaCl$_2$, 10% Glycerol, 150 mM NaCl | PBS | 3.3 |
| MK-24C10-G5-PNU (adc719) | MK-24C10 (mAb396) | 50 mM HEPES, pH 7.5, 1 mM CaCl$_2$, 10% Glycerol, 150 mM NaCl | PBS | 2.9 |
| MK-24F9-G5-PNU (adc718) | MK-24F9 (mAb416) | 50 mM HEPES, pH 7.5, 1 mM CaCl$_2$, 10% Glycerol, 150 mM NaCl | PBS | 3.7 |
| GK-22G12-G5-PNU (adc717) | GK-22G12 (mAb409) | 50 mM HEPES, pH 7.5, 1 mM CaCl$_2$, 10% Glycerol, 150 mM NaCl | PBS | 3.5 |
| XBR1-402-G5-PNU (adc096) | XBR1-402 (mAb003) | 10 mM sodium succinate, pH 5.0, 175 mM sucrose, 0.02% (w/v) Tween 20 | 10 mM sodium succinate, pH 5.0, 175 mM sucrose, 0.02% w/v Tween 20 | 3.6 |
| Ac10-G5-PNU (adc332) | Ac10 (mAb046) | 50 mM HEPES, pH 7.5, 1 mM CaCl$_2$, 10% Glycerol, 150 mM NaCl | PBS | 3.7 |

From these analyses it can be concluded that the SMAC-Technology™ conjugation has proceeded at high efficiency resulting in overall average DARs in the range of ca. 3.5 to 4.0 for each of the anti-hROR2 antibody-toxin combinations.

Example 7: EMT-6 Cell Engineering to Stably Express hROR2

EMT-6 cells cultured in DMEM complete (Dulbecco's Modified Eagle Medium (DMEM) High Glucose (4.5 g/L) with L-Glutamine with 10% (v/v) Fetal Calf Serum (FCS), 100 IU/mL of Pen-Strep-Fungizone and 2 mM L-glutamine (all Bioconcept, Allschwil, Switzerland)) at 37° C. and 5% CO$_2$ were centrifuged (6 min, 1200 rpm, 4° C.) and suspended in RPMI-1640 media (5×10$^6$ cells/mL). 400 μL of this cell suspension was then added to 400 μL of RPMI containing 10.2 μg of the transposable vector pPB-PGK-Puro-hROR2-Thr, directing co-expression of full-length ROR2 and the puromycin-resistance gene, and 3.6 μg of transposase-containing vector pCDNA3.1_hy_mPB. DNA/EMT-6 cell mixture was transferred to electroporation cuvettes (0.4 cm-gap, 165-2088, BioRad, Cressler, Switzerland) and electroporated using the Biorad Gene Pulser II with capacitance extender at 300V and 950 μF. Then, cells were incubated for 5-10 min at room temperature. Following the incubation, cells were centrifuged at 1200 rpm for 6 min, washed once and subsequently resuspended in DMEM complete prior to incubation at 37° C. in a humidified incubator at 5% CO$_2$ atmosphere. One day after electroporation, cell pools stably expressing hROR2 were selected based on puromycin resistance using 3 μg/mL of puromycin (Sigma-Aldrich, P8833-25 mg stock at 2 mg/mL).

ROR2 expression on selected EMT-6 ROR2 cells was confirmed by flow cytometry. Briefly, following trypsinization, 10$^6$ cells were centrifuged in FACS tubes; obtained pellets were resuspended in buffer (PBS with 2% (v/v) FCS). Cells were then incubated with anti-ROR2 mAb Orb38364 (Biorbyt; 30 min, 4° C., final concentration 2 μg/mL), followed by centrifugation and washing. Cells were then resuspended as previously and incubated with a mouse anti-rabbit IgG antibody PE (Abcam, ab99704) with a 1:250 dilution in the dark (30 min, 4° C.), prior to washing.

Figure 7:
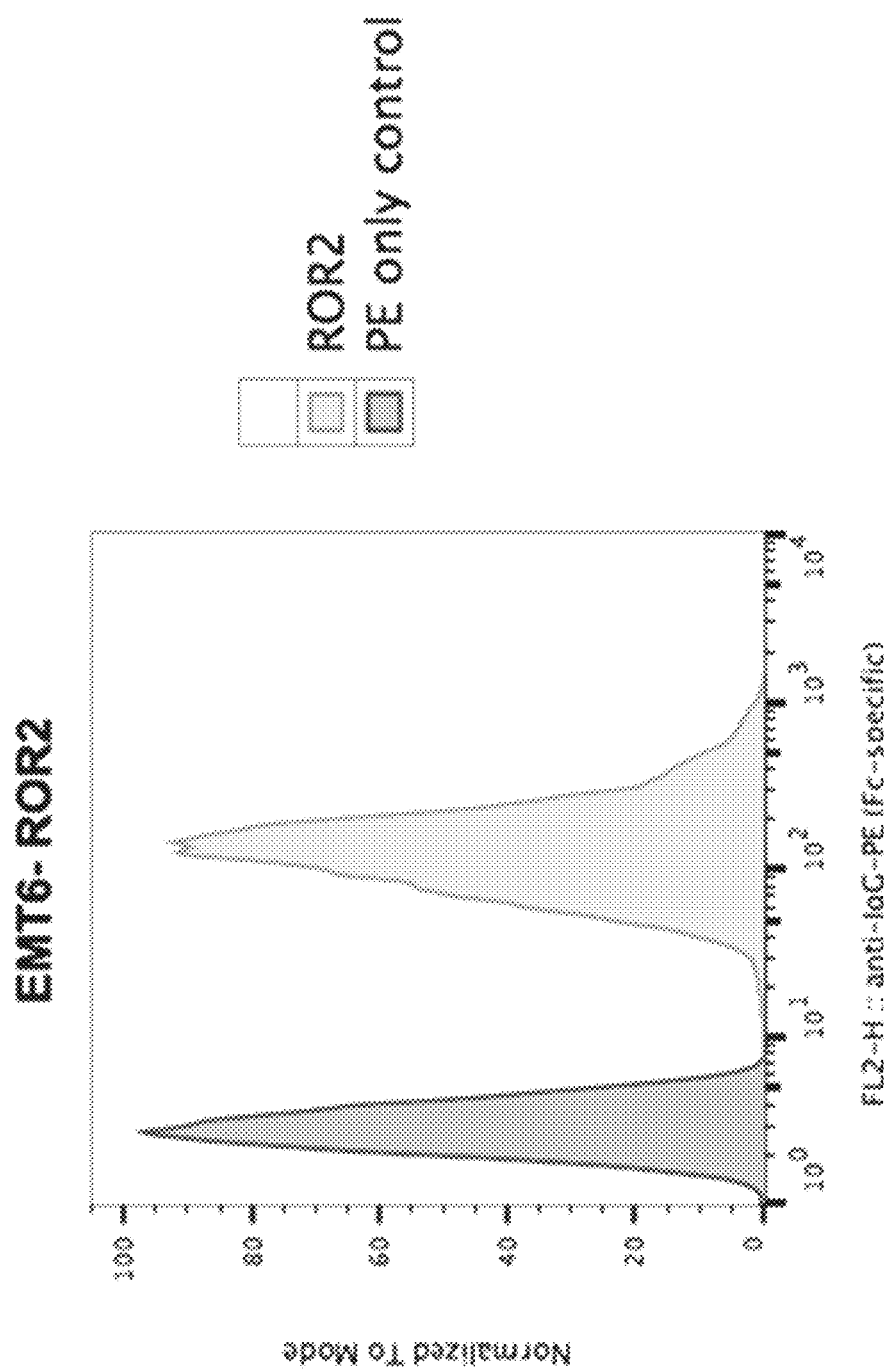
FIG. 7. FACS analysis for hROR2 expression of mouse breast cancer cell line EMT-6 engineered to stably overexpress hROR2.

Using a FACS Aria 11, cells were single cell sorted into a 96-well flat-bottom plate containing 200 μL of DMEM complete per well. This plate was incubated at 37° C. and expanded to 6 wells before screening. Cells were analyzed using a FACSCalibur instrument (BD Biosciences) and FlowJo analytical software (Tree Star, Ashland, OR). FIG. 7 shows the FACS analysis data of the high ROR2-expressing clone 14.

Example 8: In Vitro Cytotoxicity Assays of PNU-Based ADCs on hROR2-Expressing EMT-6 Cancer Cells Cytotoxicity of the anti-ROR2 ADCs of Table 12 were investigated using the EMT-6 engineered cell line of Example 7.

For this, 1000 engineered EMT6 cells (clone 14) per well were plated on 96-well plates (excluding edge wells, which contained water) in 75 μL DMEM supplemented with 10% by vol. FCS, 100 IU/mL Pen-Strep-Fungizone and 2 mM L-Glutamine at a density of 1.3×10$^5$ cells per well, and were grown at 37° C. in a humidified incubator at 5% CO$_2$ atmosphere. After a 1-day incubation, each ADC was added to respective wells in an amount of 25 μL of 3.5-fold serial dilutions in growth medium (starting ADC concentration of 80 μg/mL, giving final ADC concentrations ranging from around 20 μg/ml to 0.3 ng/ml). Each dilution was done in duplicate. After 4 additional days, plates were removed from the incubator and equilibrated to room temperature. After approximately 30 min, 50 μL was removed from each well, and then 50 μL of CellTiter-Glo® 2.0 Luminescent Solution (Promega, G9243) was added to each well. After shaking the plates at 750 rpm for 5 min followed by 20 min incubation without shaking, luminescence was measured on a Spark 10M plate reader with an integration time of 1 second per well. Curves of luminescence versus ADC concentration (ng/mL) were fitted with Graphpad Prism Software. The measurement was repeated twice. The IC$_{50}$ values, determined using the built-in "log(inhibitor) vs. response—Variable slope (four parameters)" $IC_{50}$ determination function of Prism Software, are reported in Table 12.

TABLE 12

In vitro cell killing by anti-ROR2 ADCs (ng/mL)

| ADC/Cell type | EMT-6 ROR2 |
|---|---|
| GK-1E5-G5-PNU (adc442) | 15.5 |
| GK-5A1-G5-PNU (adc443) | 341 |
| MK-3B12-G5-PNU (adc444) | 12.9 |
| GK-2G8-G5-PNU (adc445) | 15.6 |
| GK-6B10-G5-PNU (adc446) | 15.2 |
| GK-5E1-G5-PNU (adc447) | 6.5 |
| GK-5G12-G5-PNU (adc448) | 15.3 |
| MK-7C3-G5-PNU (adc449) | 46.7 |

Figure 8:
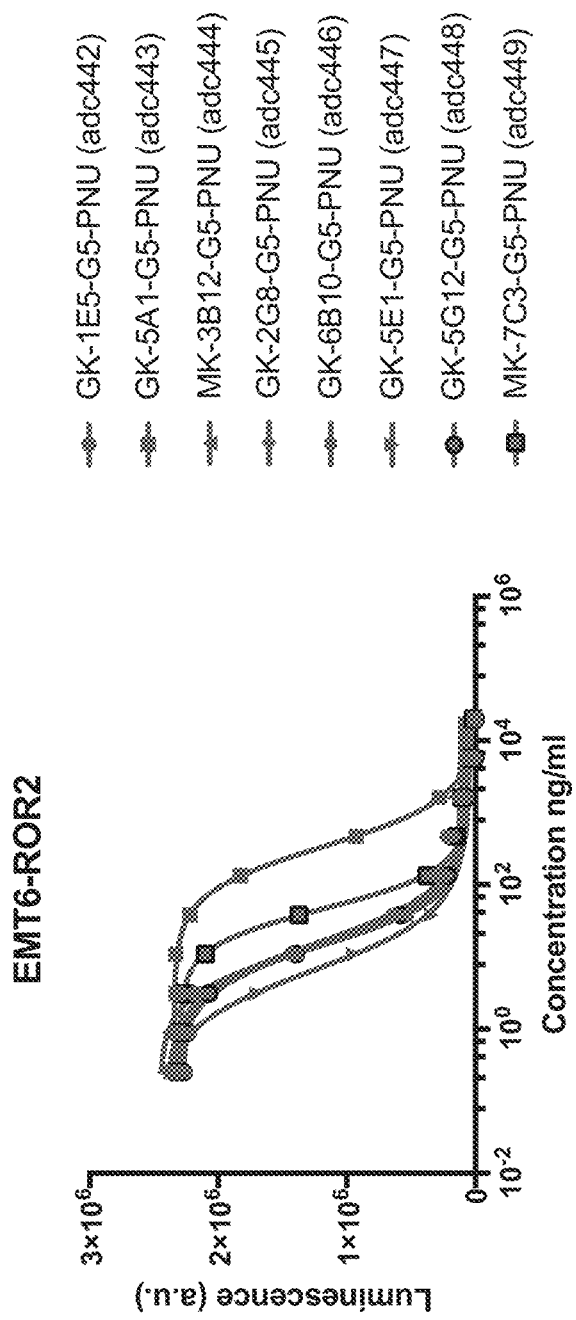
FIG. 8. Evaluation of in vitro cell killing activity of antibody drug conjugates comprising the PNU toxin (G5-PNU) site-specifically conjugated to the IgH and IgL chains of selected anti-hROR2 antibodies, as indicated, using EMT-6 cells engineered to stably express hROR2 according to Example 8.
Figure 9:
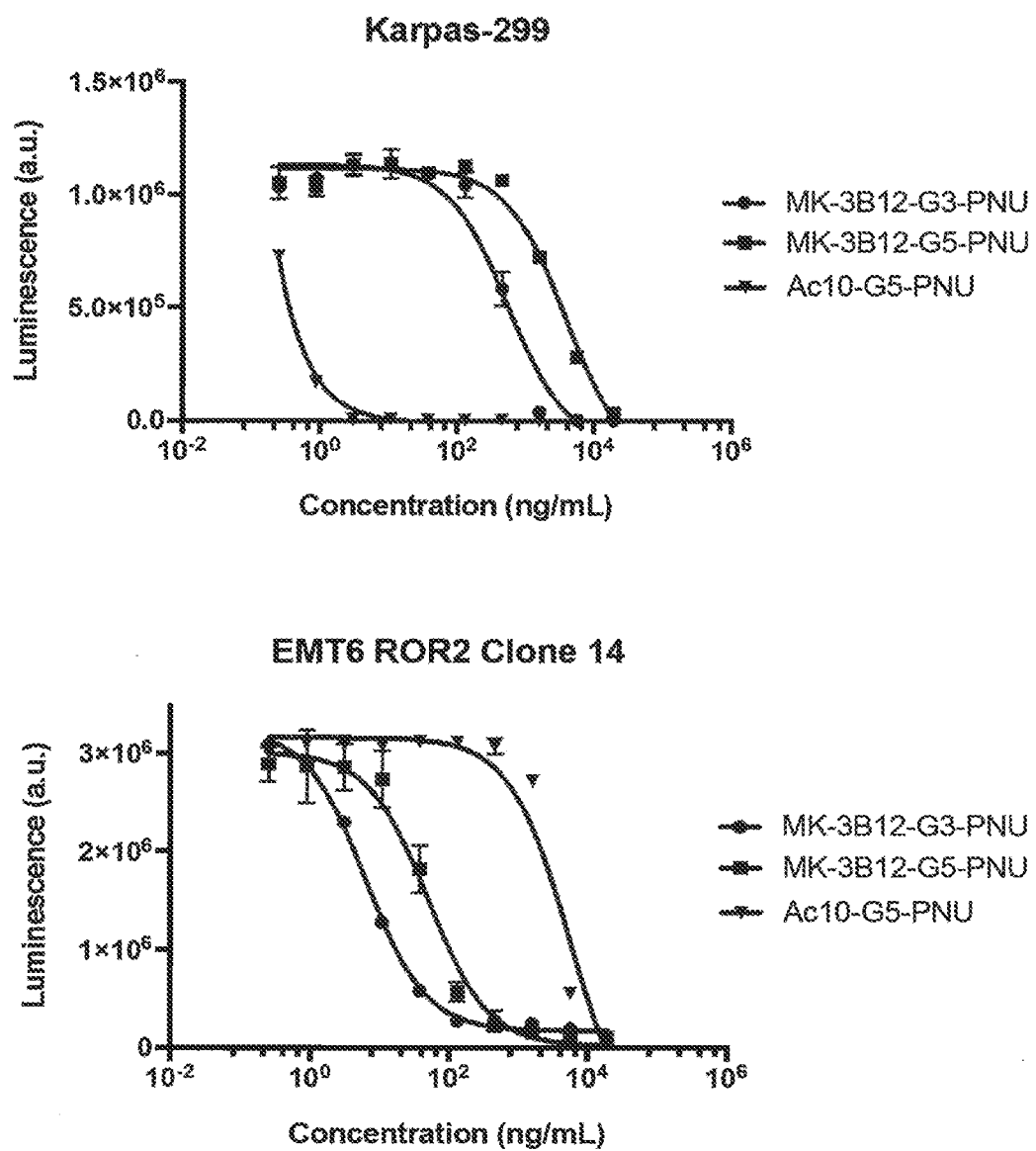
FIG. 9. Evaluation of in vitro cell killing activity of antibody drug conjugates comprising novel hROR2 monoclonal antibody clone MK-3B12 conjugated to either the PNU toxins G3-PNU or G5-PNU using EMT-6 cells engineered to stably express hROR2 according to Example 9. An isotype-matched control ADC comprising the CD30-specific antibody clone brentuximab (clone Ac10) and site-specifically conjugated to G5-PNU, as well as CD30 expressing Karpas-299 cells were used for control experiments, as indicated.
Figure 10:
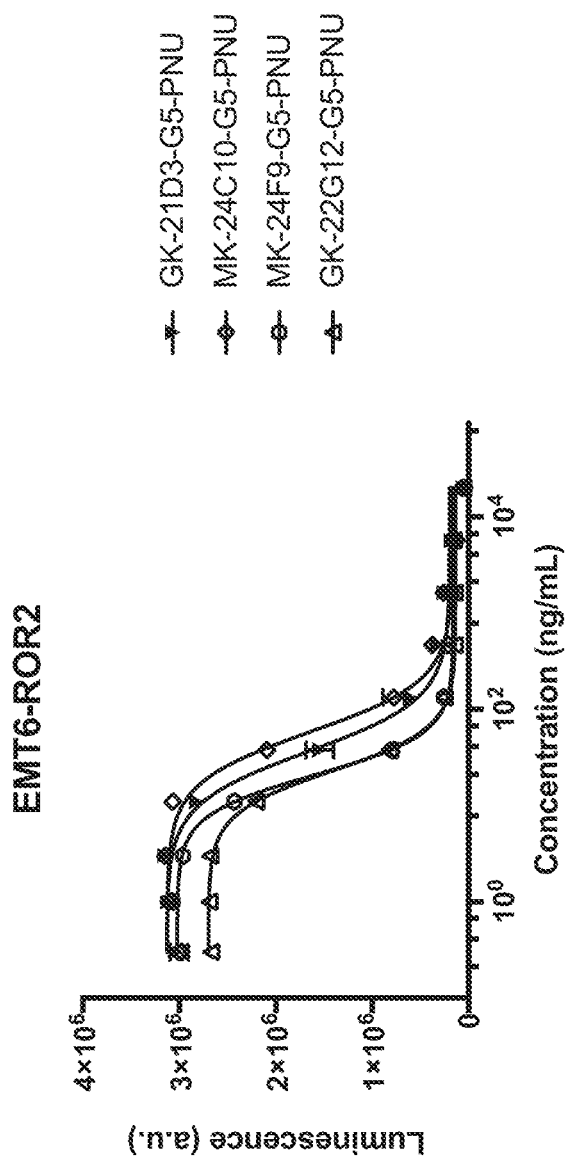
FIG. 10. Evaluation of in vitro cell killing activity of antibody drug conjugates comprising the PNU toxin (G5-PNU) site-specifically conjugated to the IgH and IgL chains of selected anti-hROR2 antibodies, as indicated, using EMT-6 cells engineered to stably express hROR2 according to Example 10.

FIG. 8 shows the dose-response curve of the in vitro cell killing assays on EMT-6 breast cancer cells stably expressing hROR2 with the PNU-based ADCs of Table 12. As per Table 12 and FIG. 8, ADCs based on the novel anti-ROR2 antibodies of the invention kill ROR2-expressing cells.

Example 9: In Vivo Cytotoxicity Assays of PNU-Based ADCs on hROR2-Expressing EMT-6 Breast Cancer Cells and on ROR2-Negative Cancer Cells Cytotoxicity of the anti-ROR2 ADCs of Table 13 were investigated using the EMT-6 engineered cell line of Example 7. Low ROR2 expressing human cell line Karpas-299 was used as control. ADC Ac10-G5-PNU was included as isotype control.

For this, $1 \times 10^3$ engineered EMT6-ROR2 (clone 14) and $2.5 \times 10^3$ Karpas-299 cells, per well, were each plated on 96-well plates (excluding edge wells, which contained water) in 75 µL DMEM supplemented with 10% by vol. FCS, 100 IU/mL Pen-Strep-Fungizone and 2 mM L-Glutamine at a density of $1.3 \times 10^5$ cells per well, and were grown at 37° C. in a humidified incubator at 5% $CO_2$ atmosphere. After a 1-day incubation, each ADC was added to respective wells in an amount of 25 µL of 3.5-fold serial dilutions in growth medium (starting ADC concentration of 80 µg/mL, giving final ADC concentrations ranging from 20 µg/ml to 0.89 ng/ml). Each dilution was done in duplicate. After 4 additional days, plates were removed from the incubator and equilibrated to room temperature. After approximately 30 min, 50 µL was removed from each well, and then 50 µL of CellTiter-Glo® 2.0 Luminescent Solution (Promega, G9243) was added to each well. After shaking the plates at 750 rpm for 5 min followed by 20 min incubation without shaking, luminescence was measured on a Spark 10M plate reader with an integration time of 1 second per well. Curves of luminescence versus ADC concentration (ng/mL) were fitted with Graphpad Prism Software. The $IC_{50}$ values, determined using the built-in "log(inhibitor) vs. response—Variable slope (four parameters)" $IC_{50}$ determination function of Prism Software, are reported in Table 13.

TABLE 13

In vitro cell killing by anti-ROR2 ADCs (ng/mL)

| ADC/Cell type<br>hROR2 expression status | EMT-6 ROR2<br>clone 14<br>Positive | Karpas-299<br>Low ROR2-<br>positive |
|---|---|---|
| MK-3B12-G5-PNU (adc444) | 50.5 | 3'930 |
| MK-3B12-G3-PNU (adc487) | 6.4 | 565 |
| AC10-G5-PNU (adc332) | 5'663 | $1.8 \times 10^5$ |

Example 10: In Vitro Cytotoxicity Assays of PNU-Based ADCs on hROR2-Expressing EMT-6 Cancer Cells Cytotoxicity of the anti-ROR2 ADCs of Table 14 were investigated using the EMT-6 engineered cell line of Example 7.

For this, $1 \times 10^3$ engineered EMT6-ROR2 (clone 14), per well, were each plated on 96-well plates (excluding edge wells, which contained water) in 75 µL DMEM supplemented with 10% by vol. FCS, 100 IU/mL Pen-Strep-Fungizone and 2 mM L-Glutamine at a density of $1.3 \times 10^5$ cells per well, and were grown at 37° C. in a humidified incubator at 5% $CO_2$ atmosphere. After a 1-day incubation, each ADC was added to respective wells in an amount of 25 µL of 3.5-fold serial dilutions in growth medium (starting ADC concentration of 80 µg/mL, giving final ADC concentrations ranging from 20 µg/ml to 0.89 ng/ml). Each dilution was done in duplicate. After 4 additional days, plates were removed from the incubator and equilibrated to room temperature. After approximately 30 min, 50 µL of CellTiter-Glo® 2.0 Luminescent Solution (Promega, G9243) was added to each well. After shaking the plates at 750 rpm for 5 min followed by 20 min incubation without shaking, luminescence was measured on a Spark 10M plate reader with an integration time of 1 second per well. Curves of luminescence versus ADC concentration (ng/mL) were fitted with Graphpad Prism Software. The $IC_{50}$ values, determined using the built-in "log(inhibitor) vs. response—Variable slope (four parameters)" $IC_{50}$ determination function of Prism Software, are reported in Table 14.

TABLE 14

In vitro cell killing by anti-ROR2 ADCs (ng/mL)

| ADC/Cell type | EMT-6 ROR2 |
|---|---|
| GK-21D3-G5-PNU (adc701) | 36.4 |
| MK-24C10-G5-PNU (adc719) | 58.1 |
| MK-24F9-G5-PNU (adc718) | 20.9 |
| GK-22G12-G5-PNU (adc717) | 22.9 |

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

Sequences

A WIPO ST 25 compatible electronic sequence listing is provided with this application, too. For the avoidance of doubt, if discrepancies exist between the sequences in the following table and the electronic sequence listing, the sequences in this table shall be deemed to be the correct ones.

| No | Qualifier | Sequence |
|----|-----------|----------|
| 1 | extracellular domain of human ROR2 | EVEVLDPNDPLGPLDGQDGPIPTLKGYFLNFLEPVNNITIVQGQTAILHCKV AGNPPPNVRWLKNDAPVVQEPRRIIRKTEYGSRLRIQDLDTTDGTYYQCV ATNGMKTITATGVLFVRLGPTHSPNHNFQDDYHEDGFCQPYRGIACARFIG NRTIYVDSLOMQGEIENRITAAFTMIGTSTHLSDQCSQFAIPSFCHFVFPLCD ARSRTPKPRELCRDECEVLESDLCRQEYTIARSNPLILMRLQLPKCEALPMPE SPDAANCMRIGIPAERLGRYHQCYNGSGMDYRGTASTTKSGHQCQPWAL QHPHSHHLSSTDFPELGGGHAYCRNPGGQMEGPWCFTQNKNVRMELCD VPSCSPRDSSKMG |
| 2 | MK-3B12 HC | EVQLVESGPGLLKPSETLSLTCAVSGYSISSGYYWGWIRQPPGKGLEWIGSIY QSGSTHYNPSLKSRVTISVDTSKNQFSLKLTSVTAADTAVYYCAREDRAGWY PFDCWGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNVNHKP SNTKVDKKVEPKSCDKTHTCPPCPAPELLGGPSVFLFPPKPKDTLMISRTPEV TCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKLTVD KSRWQQGNVFSCSVMHEALHNHYTQKSLSLSPGR |
| 3 | MK-3B12 LC | DIVMTQSPSTLSASVGDRVTITCRASQSISSWLAWYQQKPGKAPKLLIYKAS SLESGVPSRFSGSGSGTEFTLTISSLQPDDFATYYCQQYNNYWTFGQGTKVE IKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFN RGEC |
| 4 | MK-7C3 HC | EVQLLETGGGWVQPGRSLRLSCVASGFTFRSHGMHWVRQAPGKGLEWVA LIWYDGSKKYYADSVKGRFTISRDNSKNTLYLQMNSLRAEDTAVYYCARVG AGLYLDYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNVN HKPSNTKVDKKVEPKSCDKTHTCPPCPAPELLGGPSVFLFPPKPKDTLMISRT PEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSRDEL TKNQVSLTCLVKGFYPSDIAVEWESNGQPENNYKTTPPVLDSDGSFFLYSKL TVDKSRWQQGNVFSCSVMHEALHNHYTQKSLSLSPGK |
| 5 | MK-7C3 LC | AIRMTQSPSTLSASVGDRVTITCRASQTISNWLAWFQQKPGKAPKVLIYKAS SLESGVPSRFSGSGSGTEFTLTISSLQPDDFASYYCQQYNSYSYTFGQGTRLEL KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFN RGEC |
| 6 | GK-1E5 HC | EVQLVESGGGVVQPGRSLRLSCAASGFTFRSYGMHWVRQAPGKGLEWVA IIWYDGSKKYYTDSVQGRFTISRDNSKNTLYLQMNSLRAEDTAVYYCARPGI AMTGLDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 7 | GK-1E5 LC | DIQLTQSPSTLSASVGDRVTITCRASQSISSWLAWYQQKPGKAPKLLIYKASS LESGVPSRFSGSGSGTEFTLTISSLQPDDFATYYCQQYNNYWTFGQGTKVEI KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFN RGEC |
| 8 | GK-5A1 HC | QVQLVESGGGVVQPGRSLRLSCAASGFTFSSYGMYWVRQAPGKGLEWVA VIWNDGSNKYYADSVKGRFTISRDNSKNTLYLQMNSLRAEDTAVYYCAREG SGWYDYYYGMDVWGQGTTVTVSSASTKGPSVFPLAPSSKSTSGGTAALGC LVKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYNS TYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 9 | GK-5A1 LC | EIVLTQSPSTLSASVGDRVTITCRASQSISSWLAWYQQKPGKAPKLLIYKASS LESGVPSRFSGSGSGTEFTLTISSLQPDDFATYYCQQYNSYWTFGQGTKVDI KRTVAAPSVEIEPPSDEQLKSGTASVVCLLNNEYPREAKVQWKVDNALQSG NSQESVTEQDSKDSTYSLSSTLTLSKADYEKHKVYACEVTHQGLSSPVTKSFN RGEC |
| 10 | GK-2G8 HC | QVQLQESGGGVVQPGRSLRLSCAASGFTFRSYGMHWVRQAPGKGLEWV AIIWYDGSKKYYTDSVKGRFTISRDNSKNTLYLQMNSLRAEDTAVYYCARPG VAMTGLDLWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVS |

| No | Qualifier | Sequence |
|---|---|---|
| | | VLTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 11 | GK-2G8 LC | EIVMTQSPSTLSASVGDRVTITCRASQSISSWLAWYQQKPGKAPKLLIYKAS<br>SLESGVPSRFSGSGSGTEFTLTISSLQPDDFATYYCQQYNNYWTFGQGTKV<br>DIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKSF<br>NRGEC |
| 12 | GK-5E1 HC | QVTLKESGGDVVQPGRSLRLSCAASGFTFRTYGMHWVRQAPGKGPEWVA<br>LIWYDGSKKYYADSVKGRFTISRDNSKNTLYLQMNSLRAEDTAVYYCVRVRF<br>GELYFQHWGQGTLVTVSSASTKGPSVFPLAPSSKSTSGGTAALGCLVKDYFP<br>EPVTVSWNSGALTSGVHTFPAVLQSSGLYSLSSWTVPSSSLGTQTYICNVN<br>HKPSNTKVDKKVEPKSCDKTHTCPPCPAPELLGGPSVFLFPPKPKDTLMISRT<br>PEVTCVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKL<br>TVDKSRWQQGNVFSCSVMHEALHNHYTQKSLSLSPGK |
| 13 | GK-5E1 LC | DIVMTQSPSTLSASVGDRVTITCRASQSISSWLAWYQQKPGKAPKLLIYKAS<br>SLESGVPSRFSGSGSGTEFTLTISSLQPDDFATYYCQQYNSYSYSFGQGTKLEI<br>KRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFN<br>RGEC |
| 14 | GK-6B10 HC | QVQLVESGGGWQPGRSLRLSCAASGFTFSRYGMHWVRQAPGKGLEWV<br>ALIWYDGSNKYYADSVKGRFTISRDNSKNTLYLQMNSLRAEDTAVYYCARV<br>AAALHFYWGQGTLVTVSSASTKGPSVFPLAPSSKSTSGGTAALGCLVKDY<br>FPEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 15 | GK-6B10 LC | DIVMTQSPSTLSASVGDRVTITCRASQSIDNWLAWYQQKPGKAPKVLIYKA<br>SSLESGVPSRFSGSGSGTEFTLTISSLQPDDFATYYCQQYNSYSYTFGQGTKL<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKSF<br>NRGEC |
| 16 | GK-5G12 HC | QITLKESGGGVVQPGRSLRLSCAASGFTFRTYGMHWVRQAPGKGLEWVA<br>LIWYDGSNKYYADSVKGRFTISRDNSKNTLYLQMNSLRAEDTAVYYCIRVKF<br>GDLYFQHWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMIS<br>RTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSFFLYS<br>KLTVDKSRWQQGNVFSCSVMHEALHNHYTQKSLSLSPGK |
| 17 | GK-5G12 LC | EIVLTQSPSSLSASVGDRVTITCRASQGISNYLAWYQQKPGKVPKLLIYAAST<br>LQSGVPSRFSGSGSGTDFTLTISSLQPEDVATYYCQKYNSAPYTFGQGTKLEI<br>KRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFN<br>RGEC |
| 18 | GK-21D3 HC | QVQLVQSGGGVVQPGRSLRLSCAASGFTFSSYGMHWVRQAPGKGLEWV<br>AIIWYDGSNKYYADSVKGRFTISRDNSKNTLYLQMNSLRDEDTAVYYCARM<br>GAINRGGGGFDYWGQGTLVTVSSASTKGPSVFPLAPSSKSTSGGTAALGCL<br>VKDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREPQVYTL<br>PPSRDELTKNQVSLTCLVKGFYPSDIAVEWESNGQPENNYKTTPPVLDSDG<br>SFFLYSKLTVDKSRWQQGNVFSCSVMHEALHNHYTQKSLSLSPGK |
| 19 | GK-21D3 LC | DIQLTQSPSSLSASIGDRVTITCRASQGISNYLAWYQQKPGKVPKLLIYAASTL<br>QSGVPSRFSGSGSGTDFTLTISSLQPEDVSTYYCQKYNSAPWTFGQGTKVDI<br>KRTVAAPSVFIFPPSDEQLKSGTASVVCLLNNFYPREAKVQWKVDNALQSG<br>NSQESVTEQDSKDSTYSLSSTLTLSKADYEKHKVYACEVTHQGLSSPVTKSFN<br>RGEC |
| 20 | MK-24C10 HC | QVQLVESGGGVVQPGRSLRLSCAASGFTFSSYGMHWVRQAPGKGLEWV<br>AVIWFDTNKHYADSVKGRFTISRDNSKNTLYLQMNSLRAEDTAVYYCAR<br>DKGEWFGELRYYYYGMDVWGQGTTVTVSSASTKGPSVFPLAPSSKSTSGG |

| No | Qualifier | Sequence |
|---|---|---|
| | | TAALGCLVKDYFPEPVTVSWNSGALTSGVHTFPAVLQSSGLYSLSSVVTVPS<br>SSLGTQTYICNVNHKPSNTKVDKKVEPKSCDKTHTCPPCPAPELLGGPSVFL<br>FPPKPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPP<br>VLDSDGSFFLYSKLTVDKSRWQQGNVFSCSVMHEALHNHYTQKSLSLSPGK |
| 21 | MK-24C10 LC | EIVLTQSPLSLPVTPGEPASISCRSSQSLLHSNGYNYLDWYLQKPGQSPQLLIY<br>LGSNRASGVPDRFSGSGSGTDFTLKISRVEAEDVGVYYCMQALQTPYTFGQ<br>GTKLEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLSSP<br>VTKSFNRGEC |
| 22 | MK-24F9 HC | EVQLQQWGAGLLKPSETLSLTCAVYGGSFSGYYWSIRQPPGKGLEWIGD<br>INHSRTTNYNPSLKSRVTISVDTSKNQFSLKLSSVTAADTAVYYCARGGEQW<br>LVPFDYWDQGTLVTVSSASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTLMISRTP<br>EVTCVWDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPGK |
| 23 | MK-24F9 LC | EIVMTQSPSTLSASVGDRVTITCRASQSISHWLAWYQQKPGKAPKLLIYKAS<br>SLKSGVPSRFNGSGSGTEFTLTISSLQPDDFATYYCQHYNTYSRTFGQGTKV<br>DIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKSF<br>NRGEC |
| 24 | GK-22G12 HC | EVQLVESGGGLVQSGGSLRLSCAASGFTFSSQRLSWVRQAPGKGLEWVAN<br>IKQDGSEKNYVDSVRGRFHSRDIAKNSLYLQMNSLRAEDTAVYYCARDGYR<br>NGWHIPEDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMI<br>SRTPEVTCVWVDVSHEDPEVKFNWYVDGVEVHNAKTKPREEQYNSTYRVV<br>SVLTVLHQDWLNGKEYKCKVSNKALPAPIEKTISKAKGQPREPQVYTLPPSR<br>DELTKNQVSLTCLVKGFYPSDIAVEWESNGQPENNYKTTPPVLQSDGSFFLY<br>SKLTVDKSRWQQGNVFSCSVMHEALHNHYTQKSLSLSPGK |
| 25 | GK-22G12 LC | DIVMTQSPSSLSASVGDRVTITCRASQGISNYLAWYQQKPGKVPKLLIYAAS<br>TLQSGVPSRFSGSGSGTDFTLTISSLQPEDVSTYYCQKHNRAPWTFGQGTKL<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKSF<br>NRGEC |
| 26 | MK-3B12 HC CDR1 | GYSISSGYY |
| 27 | MK-3B12 HC CDR2 | IYQSGST |
| 28 | MK-3B12 HC CDR3 | CAREDRAGWYPFDCW |
| 29 | MK-3B12 LC CDR1; GK-1E5 LC CDR1; GK-5A1 LC CDR1; GK-2G8 LC CDR1; GK-5E1 LC CDR1; GK-1H2 LC CDR1; GK-2A9 LC CDR1; GK-5A6 LC CDR1 | QSISSW |
| 30 | MK-3B12 LC CDR3; GK-1E5 LC CDR3; GK-2G8 LC CDR3; GK-1H2 LC CDR3; GK-2A9 LC CDR3 | CQQYNNYWTF |
| 31 | MK-7C3 HC CDR1 | GFTFRSHG |
| 32 | MK-7C3 HC CDR2; GK-1E5 HC CDR2; GK-2G8 HC CDR2; GK-5E1 HC CDR2; GK-1H2 HC CDR2; GK-2A9 HC CDR2 | IWYDGSKK |
| 33 | MK-7C3 HC CDR3 | CARVGAGLYLDYW |
| 34 | MK-7C3 LC CDR1 | QTISNW |
| 35 | MK-7C3 LC CDR3; GK-6B10 LC CDR3; GK-5A6 LC CDR3 | CQQYNSYSYTF |
| 36 | GK-1E5 HC CDR1; GK-2G8 HC CDR1; GK-1H2 HC CDR1; GK-2A9 HC CDR1 | GFTFRSYG |
| 37 | GK-1E5 HC CDR3; GK-1H2 HC CDR3 | CARPGIAMTGLDYW |
| 38 | GK-5A1 HC CDR1; GK-21D3 HC CDR1; MK-24C10 HC CDR1; GK-21F1 HC CDR1; MK-24C12 HC CDR1 | GFTFSSYG |

-continued

| No | Qualifier | Sequence |
|---|---|---|
| 39 | GK-5A1 HC CDR2 | IWNDGSNK |
| 40 | GK-5A1 HC CDR3 | CAREGSGWYDYYYGMDVW |
| 41 | GK-5A1 LC CDR3 | CQQYNSYWTF |
| 42 | GK-5E1 LC CDR3 | CQQYNSYSYSF |
| 43 | GK-2G8 HC CDR3; GK-5E1 HC CDR1; GK-5G12 HC CDR1; GK-2A9 HC CDR3; GK-5A6 HC CDR1 | CARPGVAMTGLDLW |
| 44 | GK-5E1 HC CDR3 | CVRVRFGELYFQHW |
| 45 | GK-6B10 HC CDR1 | GFTFSRYG |
| 46 | GK-6B10 HC CDR2; GK-5G12 HC CDR2; GK-21D3 HC CDR2; GK-5A6 HC CDR2; GK-21F1 HC CDR2 | IWYDGSNK |
| 47 | GK-6B10 HC CDR3 | CARVAAALHFHYW |
| 48 | GK-6B10 LC CDR1 | QSIDNW |
| 49 | GK-5G12 HC CDR3; GK-5A6 HC CDR3 | CIRVKFGDLYFQHW |
| 50 | GK-5G12 LC CDR1; GK-21D3 LC CDR1; GK-22G12 LC CDR1; GK-21F1 LC CDR1; GK-21G5 LC CDR1; GK-21E6 LC CDR1; GK-22E12 LC CDR1 | QGISNY |
| 51 | GK-5G12 L CCDR3 | CQKYNSAPYTF |
| 52 | GK-21D3 HC CDR3; GK-21F1 HC CDR3 | CARMGAINRGGGGFDYW |
| 53 | GK-21D3 LC CDR3; GK-21F1 LC CDR3 | CQKYNSAPWTF |
| 54 | MK-24C10 HC CDR2; MK-24C12 HC CDR2 | IWFDGTNK |
| 55 | MK-24C10 HC CDR3; MK-24C12 HC CDR3 | CARDKGEWFGELRYYYYGMDVW |
| 56 | MK-24C10 LC CDR1; MK-24C12 LC CDR1 | QSLLHSNGYNY |
| 57 | MK-24C10 LC CDR3; MK-24C12 LC CDR3 | CMOALQTPYTF |
| 58 | MK-24F9 HC CDR1; GK-21G5 HC CDR1; GK-23A8 HC CDRI | GGSFSGYY |
| 59 | MK-24F9 HC CDR2 | INHSRTT |
| 60 | MK-24F9 HC CDR3 | CARGGEQWLVPFDYW |
| 61 | MK-24F9 LC CDR1; GK-23A8 LC CDR1 | QSISHW |
| 62 | MK-24F9 LC CDR3; GK-23A8 LC CDR3 | CQHYNTYSRTF |
| 63 | GK-22G12 HC CDR1; GK-21E6 HC CDR1; GK-22E12 HC CDR1 | GFTFSSQR |
| 64 | GK-22G12 HC CDR2; GK-21E6 HC CDR2; GK-22E12 HC CDR2 | IKQDGSEK |
| 65 | GK-22G12 HC CDR3; GK-21E6 HC CDR3; GK-22E12 HC CDR3 | CARDGYRNGWHIPEDYW |
| 66 | GK-22G12 LC CDR3; GK-21G5 LC CDR3; GK-21E6 LC CDR3; GK-22E12 LCCDR3 | CQKHNRAPWTF |
| 67 | CDR1; X1 = F or G, X2 = T or S, X3 = R or S, X4 = S, T, R or G, X5 = H, Y or Q, X6 = G, Y or R | $GX_1X_2FX_3X_4X_5X_6$ |
| 68 | CDR2; X7 = W or K, X8 = Y, N, F or Q, X9 = S or T, X10 = K, N or E | $IX_7X_8DGX_9X_{10}K$ |
| 69 | CDR1; X11 = S, T or G, X12 = S, N or H and X13 = W or Y | $QX_{11}ISX_{12}X_{13}$ |
| 70 | CDR3; X14 = Q or M, X15 = K, H or Q, X16 = H, Y or A, X17 = N or L, X18 = R, T, Q, S or N; X19 = A, Y or T; X20 = P, S or W, X21 = W, R, Y or absent, X22 = S or T. | $CX_{14}X_{15}X_{16}X_{17}X_{18}X_{19}X_{20}X_{21}X_{22}F$ |

| No | Qualifier | Sequence |
|---|---|---|
| 71 | CDR1; X3 = R or S, and X4 = S, T | GFTFX3X4YG |
| 72 | GK-5G12 LC CDR2; GK-21D3 LC CDR2; GK-22G12 LC CDR2; GK-21F1 LC CDR2; GK-21G5 LC CDR2; GK-21E6 LC CDR2; GK-22E12 LC CDR2 | AAS |
| 73 | MK-3B12 LC CDR2; MK-7C3 LC CDR2; GK-1E5 LC CDR2; GK-5A1 LC CDR2; GK-2G8 LC CDR2; GK-5E1 LC CDR2; GK-6B10 LC CDR2; MK-24F9 LC CDR2; GK-1H2 LC CDR2; GK-2A9 LC CDR2; GK-5A6 LC CDR2; GK-23A8 LC CDR2 | KAS |
| 74 | MK-24C10 LC CDR2, MK-24C12 LC CDR2 | LGS |
| 75 | GK-1H2 HC | EVQLLESGGGVVQPGRSLRLSCAASGFTFRSYGMHWVRQAPGKGLEWVA IIWYDGSKKYYTDSVKGRFTISRDNSKNTLYLQMNSLRAEDTAVYYCARPGI AMTGLDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 76 | GK-1H2 LC | EIVMTQSPSTLSASVGDRVTITCRASQSISSWLAWYQQKPGKAPKLLIYKAS SLESGVPSRFSGSGSGTEFTLTISSLQPDDFATYYCQQYNNYWTFGQGTKLEI KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFN RGEC |
| 77 | GK-2A9 HC | QVQLVQSGGGVVQPGRSLRLSCAASGFTFRSYGMHWVRQAPGKGLEWV AIIWYDGSKKYYTDSVKGRFTISRDNSKNTLYLQMNSLRAEDTAVYYCARPG VAMTGLDLWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 78 | GK-2A9 LC | EIVLTQSPSTLSASVGDRVTITCRASQSISSWLAWYQQKPGKAPKLLIYKASS LESGVPSRFSGSGSGTEFTLTISSLQPDDFATYYCQQYNNYWTFGQGTKVDI KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFN RGEC |
| 79 | GK-5A6 HC | EVQLQESGGGVVQPGRSLRLSCAASGFTFRTYGMHWVRQAPGKGLEWV ALIWYDGSNKYYADSVKGRFTISRDNSKNTLYLQMNSLRAEDTAVYYCIRVK FGDLYFQHWGQGTLVTVSSASTKGPSVFPLAPSSKSTSGGTAALGCLVKDY FPEPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 80 | GK-5A6 LC | DWMTQSPSTLSASVGDRVTITCRASQSISSWLAWYQQKPGKAPKLLIYKA SSLESGVPSRFSGSGSGTEFTLTISSLQPDDFATYYCQQYNSYSYTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSF NRGEC |
| 81 | GK-21F1 HC | QVQLVQSGGGVVQPGRSLRLSCAASGFTFSSYGMHWVRQAPGKGLEWV AIIWYDGSNKYYADSVKGRFTISRDNSKNTLYLQMNSLRDEDTAVYYCARM GAINRGGGGFDYWGQGTLVTVSSASTKGPSVFPLAPSSKSTSGGTAALGCL VKDYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKPKD TLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVYTL PPSRDELTKNQVSLTCLVKGFYPSDIAVEWESNGQPENNYKTTPPVLDSDG SFFLYSKLTVDKSRWQQGNVFSCSVMHEALHNHYTQKSLSLSPGK |
| 82 | GK-21F1 LC | DIQLTQSPSSLSASIGDRVTITCRASQGISNYLAWYQQKPGKVPKLLIYAASTL QSGVPSRFSGSGSGTDFTLTISSLQPEDVSTYYCQKYNSAPWTFGQGTKVDI KRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFN RGEC |

| No | Qualifier | Sequence |
|---|---|---|
| 83 | MK-24C12 HC | EVQLVESGGGVVQPGRSLRLSCAASGFTFSSYGMHWVRQAPGKGLEWVA VIWFDGTNKHYADSVKGRFTISRDNSKNTLYLQMNSLRAEDTAVYYCARDK GEWFGELRYYYYGMDVWGQGTTVTVSSASTKGPSVFPLAPSSKSTSGGTA ALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQ YNSTYRWSVLTVLHQDWLNGKEYKCKVSNKALPAPIEKTISKAKGQPREPQ VYTLPPSRDELTKNQVSLTCLVKGFYPSDIAVEWESNGQPENNYKTTPPVLQ SDGSFFLYSKLTVDKSRWQQGNVFSCSVMHEALHNHYTQKSLSLSPGK |
| 84 | MK-24C12 LC | EIVLTQSPLSLPVTPGEPASISCRSSQSLLHSNGYNYLDWYLQKPGQSPQLLIY LGSNRASGVPDRFSGSGSGTDFTLKISRVEAEDVGVYYCMQALQTPYTFGQ GTKLEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSP VTKSFNRGEC |
| 85 | GK-21G5 HC | QVQLQQWGAGLLKPSETLSLTCAVYGGSFSGYYWSWIRQPPGKGLEWIGE INHSGITNYNPSLKSRLTVSVDTSKNQFSLKLSSVTAADTAVYYCARGGDQW LVPFDNWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELT KNQVSLTCLVKGFYPSDIAVEWESNGQPENNYKTTPPVLDSDGSFFLYSKLT VDKSRWQQGNVFSCSVMHEALHNHYTQKSLSLSPGK |
| 86 | GK-21G5 LC | DIVMTQSPSSLSASVGDRVTITCRASQGISNYLAWYQQKPGKVPKLLIYAAS TLQSGVPSRFSGSGSGTDFTLTISSLQPEDVSTYYCQKHNRAPWTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSF NRGEC |
| 87 | GK-23A8 HC | QVQLQQWGAGLLKPSETLSLTCAVYGGSFSGYYWSWIRQPPGKGLEWIGE INHSGITNYNPSLKSRLTVSVDTSKNQFSLKLSSVTAADTAVYYCARGGDQW LVPFDNWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELT KNQVSLTCLVKGFYPSDIAVEWESNGQPENNYKTTPPVLDSDGSFFLYSKLT VDKSRWQQGNVFSCSVMHEALHNHYTQKSLSLSPGK |
| 88 | GK-23A8 LC | EIVMTQSPSTLSASVGDRVTITCRASQSISHWLAWYQQKPGKAPKLLIYKAS SLKSGVPSRFNGSGSGTEFTLTISSLQPDDFATYYCQHYNTYSRTFGQGTKV DIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSF NRGEC |
| 89 | GK-2156 HC | RVQLVQSGGGLVQGGSLRLSCAASGFTFSSQRLSWVRQAPGKGLEWVA NIKQDGSEKNYVDSVRGRFTISRDIAKNSLYLQMNSLRAEDTAVYYCARDG YRNGWHIPEDYWGQGTLVTVSSASTKGPSVFPLAPSSKSTSGGTAALGCLV KDYFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDTL MISRTPEVTCVVVDVSHEDPEVKFNWYVDGVEVHNAKTKPREEQYNSTYR VVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFF LYSKLTVDKSRWQQGNVFSCSVMHEALHNHYTQKSLSLSPGK |
| 90 | GK-21E6 LC | DVVMTQSPSSLSASVGDRVTITCRASQGISNYLAWYQQKPGKVPKLLIYAAS TLQSGVPSRFSGSGSGTDFTLTISSLQPEDVSTYYCQKHNRAPWTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSF NRGEC |
| 91 | GK-22E12 HC | EVQLLESGGGLVQGGSLRLSCAASGFTFSSQRLSWVRQAPGKGLEWVANI KQDGSEKNYVDSVRGRFTISRDIAKNSLYLQMNSLRAEDTAVYYCARDGYR NGWHIPEDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFLY SKLTVDKSRWQQGNVFSCSVMHEALHNHYTQKSLSLSPGK |

-continued

| No | Qualifier | Sequence |
|---|---|---|
| 92 | GK-22E12 LC | AIRMTQSPSSLSASVGDRVTITCRASQGISNYLAWYQQKPGKVPKLLIYAAS TLQSGVPSRFSGSGSGTDFTLTISSLQPEDVSTYYCQKHNRAPWTFGQGTK VEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKS FNRGEC |
| 93 | GK-21G5 HC CDR2, GK-23A8 HC CDR2 | INHSGIT |
| 94 | GK-5E1 HC CDR1; GK-5G12 HC CDR1; GK-5A6 HC CDR1 | GFTFRTYG |
| 95 | GK-21G5 HC CDR3, GK-23A8 HC CDR3 | CARGGDQWLVPFDNW |
| 96 | *Staphylococcus aureus* sortase A recognition sequence, with X being any amino acid | -LPXSG |
| 97 | *Staphylococcus aureus* sortase A recognition sequence, with X being any amino acid | -LPXAG |
| 98 | recognition sequence for *Staphylococcus aureus* sortase A or engineered sortase A 4S-9 from *Staphylococcus aureus*, with X being any amino acid | -LPXTG |
| 99 | recognition sequence for engineered sortase A 2A-9 from *Staphylococcus aureus*, with X being any amino acid | -LAXTG |
| 100 | recognition sequence for engineered sortase A 2A-9 from *Staphylococcus aureus* | -LAETG |
| 101 | *Streptococcus pyogenes* sortase A recognition sequence, with X being any amino acid | -LPXTA |
| 102 | *Staphylococcus aureus* sortase recognition sequence | -NPQTN |
| 103 | huVH4B-3'Leader-FR1 | CAGGTGCAGCTGCAGGAGTCSG |
| 104 | huVH5B-3'Leader-FR1 | CAGGTACAGCTGCAGCAGTCA |
| 105 | huVH6B-3'Leader-FR1 | CAGGTGCAGCTACAGCAGTGGG |
| 106 | huVH10Ba-3'Leader-FR1 | GAGGTGCAGCTGKTGGAGWCT |
| 107 | huVH10Bb-3'Leader-FR1 | GAGGTGCAGCTGKTGGAGWCC |
| 108 | huVH12B-3'Leader-FR1 | CAGGTCCAGCTKGTRCAGTCTGG |
| 109 | huVH14B-3'Leader-FR1 | CAGRTCACCTTGAAGGAGTCTG |
| 110 | huVH22B-3'Leader-FR1 | CAGGTGCAGCTGGTGSARTCTGG |
| 111 | rat_IgG12abc_R | CAGGGTGACTGAGGGCGTAG |
| 112 | rat_IgM_R | GTTGGGAAGGTTCTGACACC |
| 113 | hu5'VK1-5_3'Leader-FR1 | GACATCCAGATGACCCAGTC |
| 114 | hu5'VK1-9_3'Leader-FR1 | GACATCCAGTTGACCCAGTCT |
| 115 | hu5'VK1D-43_3'Leader-FR1 | GCCATCCGGATGACCCAGTC |
| 116 | hu5'VK2-24_3'Leader-FR1 | GATATTGTGATGACCCAGAC |
| 117 | hu5'VK2-28_3'Leader-FR1 | GATATTGTGATGACTCAGTC |
| 118 | hu5'VK2-30_3'Leader-FR1 | GATGTTGTGATGACTCAGTC |
| 119 | hu5'VK3-11_3'Leader-FR1 | GAAATTGTGTTGACACAGTC |
| 120 | hu5'VK3-15_3'Leader-FR1 | GAAATAGTGATGACGCAGTC |
| 121 | hu5'VK3-20_3'Leader-FR1 | GAAATTGTGTTGACGCAGTCT |
| 122 | hu5'VK4-1_3'Leader-FR1 | GACATCGTGATGACCCAGTC |
| 123 | rat_CK_R | CTTGACACTGATGTCTCTGGG |
| 124 | hu3'_JH1245_NheI | TGAGGAGACGGTGACCAG |

| No | Qualifier | Sequence |
|---|---|---|
| 125 | hu3'_JH3_NheI | TGAAGAGACGGTGACCATTG |
| 126 | hu3'_JH6_NheI | TGAGGAGACGGTGACCGTG |
| 127 | huHSCJK20-B_BsiWI | TTTGATCTCCAGCTTGGTCCC |
| 12.8 | huHSCJK3o-B_BsiWI | TTTGATATCCACTTTGGTCCC |
| 129 | huHSCJK5o-B_BsiWI | TTTAATCTCCAGTCGTGTCCC |
| 130 | huHSCJK14o-B_BsiWI | TTTGATYTCCACCTTGGTCCC |
| 131 | XBR1-402 LC | SYELTQLPSVSVSLGQTARITCEGNNIGSKAVHWYQQKPGLAPGLLIYDDDE RPSGVPDRFSGSNSGDTATLTISGAQAGDEADYYCQVWDSSAYVFGGGTQ LTVTGQPKAAPSVTLFPPSSEELQANKATLVCLISDFYPGAVTVAWKADSSP VKAGVETTTPSKQSNNKYAASSYLSLTPEQWKSHKSYSCQVTHEGSTVEKT VAPTECS |
| 132 | XBR1-402 HC | QEQQKESGGGLFKPTDTLTLTCTASGFDISSYYMSWVRQAPGNGLEWIGAI GISGNAYYASWAKSRSTITRNTNLNTVTLKMTSLTAADTATYFCARDHPTY GMDLWGPGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSRDELTK NQVSLTCLVKGFYPSDIAVEWESNGQPENNYKTTPPVLDSDGSFFLYSKLTV DKSRWQQGNVFSCSVMHEALHNHYTQKSLSLSPGK |
| 133 | Ac10 LC | QIQLQQSGPEVVKPGASVKISCKASGYTFTDYYITWVKQKPGQGLEWIGWI YPGSGNTKYNEKFKGKATLTVDTSSSTAFMQLSSLTSEDTAVYFCANYGNY WFAYWGQGTQVTVSAASTKGPSVFPLAPSSKSTSGGTAALGCLVKDYFPEP VTVSWNSGALTSGVHTFPAVLQSSGLYSLSSVVTVPSSSLGTQTYICNVNHK PSNTKVDKKVEPKSCDKTHTCPPCPAPELLGGPSVFLFPPKPKDTLMISRTPE VTCVVVDVSHEDPEVKFNWYVDGVEVHNAKTKPREEQYNSTYRVVSVLTV LHQQWLNGKEYKCKVSNKALPAPIEKTISKAKGQPREPQVYTLPPSRDELTK NQVSLTCLVKGFYPSDIAVEWESNGQPENNYKTTPPVLDSDGSFFLYSKLTV DKSRWQQGNVFSCSVMHEALHNHYTQKSLSLSPGK |
| 134 | Ac10 LC | DIVLTQSPASLAVSLGQRATISCKASQSVDFDGDSYMNWYQQKPGQPPKV LIYAASNLESGIPARFSGSGSGTDFTLNIHPVEEEDAATYYCQQSNEDPWTF GGGTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQGLS SPVTKSFNRGEC |
| 135 | Linker derived from *Staphylococcus aureus* sortase A recognition sequence, with X being any amino acid and n ≥ 1 and ≥21 | -LPT(Gn)- |
| 136 | Linker derived from *Staphylococcus aureus* sortase A recognition sequence, with X being any amino acid and n ≥ 1 and ≥21 | -LPXA(Gn)- |
| 137 | Linker derived from recognition sequence for *Staphylococcus aureus* sortase A or engineered sortase A 4S-9 from *Staphylococcus aureus*, with X being any amino acid and n ≥ 1 and ≥21 | -LPXS(Gn)- |
| 138 | Linker derived from recognition sequence for engineered sortase A 2A-9 from *Staphylococcus aureus*, with X being any amino acid and n ≥ 1 and ≥21 | -LAXT(Gn)- |
| 139 | Linker derived from *Streptococcus pyogenes* sortase A recognition sequence, with X being any amino acid and n ≥ 1 and ≥21 | -LPXT(Gn)-or-LPXT(An)- |
| 140 | Linker derived from *Staphylococcus aureus* sortase recognition sequence, with n ≥ 1 and ≥21 | -NPQT(Gn)- |
| 141 | extracellular domain of cynomolgus ROR2 (cROR2) | EVEVPDPNDPLGPLDGQD GPIPTLKGYFLNFLEPVNNIT IVQGQTAILHCKVAGNPPP NVRWLKNDAPVVQEPRRIII RKTEYGSRLRIQDLDTTDTG YYQCVATNGMKTITATGVL FVRLGPTHSPNHNFQDDYH EDGFCQPYRGIACARFIGNR TIYVDSLQMQGEIENRITAA |

| No | Qualifier | Sequence |
|---|---|---|
| | | FTMIGTSTHLSDQCSQFAIP<br>SFCHFVFPLCDARSRAPKPR<br>ELCRDECEVLESDLCRQEYTI<br>ARSNPLILMRLQLPKCEALP<br>MPESPDAANCMRIGIPAER<br>LGRYHQCYNGSGTDYRGTA<br>STTKSGHQCQPWALQHPH<br>SHHLSSTDFPELGGGHAYC<br>RNPGGQMEGPWCFTQNK<br>NVRMELCDVPSCSPRDSSK<br>MG |
| 142 | extracellular domain of murine ROR2 (mROR2) | EVEDSEAIDTLGQPDGPDSP<br>LPTLKGYFLNFLEPVNNITIV<br>QGQTAILHCKVAGNPPPNV<br>RWLKNDAPVVQEPRRVIIR<br>KTEYGSRLRIQDLDTTDTGY<br>YQCVATNGLKTITATGVLYV<br>RLGPTHSPNHNFQDDDQE<br>DGFCQPYRGIACARFIGNRT<br>IYVDSLOMQGEIENRITAAF<br>TMIGTSTQLSDQCSQFAIPS<br>FCHFVFPLCDARSRAPKPRE<br>LCRDECEVLENDLCRQEYTI<br>ARSNPLILMRLQLPKCEALP<br>MPESPDAANCMRIGIPAER<br>LGRYHQCYNGSGADYRGM<br>ASTTKSGHQCQPWALQHP<br>HSHRLSSTEFPELGGGHAYC<br>RNPGGQMEGPWCFTQNK<br>NVRVELCDVPPCSPRDGSK<br>MG |

REFERENCES

Non Patent Literature

Abbott M. et al., "Current approaches to fine mapping of antigen-antibody interactions": Immunology, 2014: 142 (4): 526-35.
Altschul et al., J. Mol. Biol. 215:403-410, 1990
Altschul et al., Nuc. Acids Res. 25:3389-3402, 1977
Balakrishnan et al. (2016) Clin Cancer Res. doi: 10.1158/1078-0432
Beaucage et al., Tetra. Lett., 22:1859, 1981
Beerli et al. (2015) PloS One 10, e131177
Bendas, BioDrugs, 15: 215-224, 2001
Beraud et al., Inflamm. Allergy Drug Targets. 10:32242, 2011
Berry et al., 2003 Hybridoma and Hybridomics 329(1-2): 112-124
Bird et al., Science 242:423-426, 1988;
Bittner et al., Meth. Enzymol., 153:516, 1987
Bond et al., J. Mol. Biol. 332:643-55, 2003
Brent et al., Current Protocols in Molecular Biology, John Wiley & Sons, Inc. (Ringbou ed., 2003).
Brown et al., Meth. Enzymol. 68:109, 1979
Cai and Garen, Proc. Natl. Acad. Sci. USA 93:6280-85, 1996
Chen et al., "A general strategy for the evolution of bond-forming enzymes using yeast display": PNAS 2011; 108 (28); 113'9-11404.
Dorr B M et al., "Reprogramming the specificity of sortase enzymes": PNAS 2014; 111, 13343-8.
Dumoulin et al., Nat. Struct. Biol. 11:500-515, 2002
Dyba et al., Curr. Pharm. Des. 10:2311-34, 2004
Elliot and O'Hare, Cell 88:223, 1997
Ghahroudi et al., FEBS Letters 414:521-526, 1997
Harlow & Lane, Using Antibodies, A Laboratory Manual, Cold Spring Harbor Laboratory Press, Cold Spring Harbor, New York, 1998.
Lefranc M P et al. "IMGT®, the International ImMunoGeneTics information System® 25 years on"; Nucleic Acids Res 2015; 43; D413-22.
Harrington et al., Nat. Genet. 15:345, 1997
Huston et al., Proc. Natl. Acad. Sci. USA 85:5879-5883, 1988
Mattila et al., Nucleic Acids Res. 19:967, 1991; and Eckert et al., PCR Methods and Applications 1:17, 1991.
Kuyucak et al., Future Med. Chem. 6:1645-58, 2014
Marcu-Malina et al., Expert Opinion on Biological Therapy, Vol. 9. No. 5
Middlebrook et al., Microbiol. Rev. 48:199-221, 1984
Morioka et al., Cancer Sci. 100: 1227-1233, 2009
Narang et al., Meth. Enzymol. 68:90, 1979
Needleman and Wunsch, J. Mol. Biol. 48:443, 1970
Pearson and Lipman, Proc. Nat'l. Acad. Sci. USA 85:2444, 1988
Quintieri et al., Clin. Cancer Res 11:1608-1617 (2005)
Rebagay et al. (2012) Front Oncol. 2(34)
Reiter et al., Int. J. Cancer 67:113-23, 1996
Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978.
Remington's Pharmaceutical Sciences, Mack Publishing Co., Easton, PA
Rosenfeld et al., Cell 68:143, 1992
Russell et al, J. Mol. Biol., 244: 332-350 (1994)
Sblattero and Bradbury 1998 Immunotechnology 3, 271-278
Scharf et al., Results Probl. Cell Differ. 20:125, 1994;
Skerra and Plackthun, Science 240:103841, 1988
Smith and Waterman, Adv. Appl. Math. 2:482c, 1970

Smith, Annu. Rev. Microbiol. 49:807, 1995
Tiller et al., J Immunol Methods. 2008 May 20; 334(1-2): 142
Waldmeier L et al. "Transpo-mAb display: Transposition-mediated B cell display and functional screening of full-length IgG antibody libraries"; MAbs 2016; 8(4), 726-40.
Ward et al., Nature 341:544-546, 1989
Ward et al., Nature 341:544-546, 1989
Winnacker, From Genes to Clones, VCH Publishers, N.Y., N.Y., 1987
Wu et al., Nat. Biotechnol, 23: 1 137-1 146 (2005)

PATENT LITERATURE

U.S. Pat. No. 5,075,109
U.S. Pat. No. 4,452,775
U.S. Pat. No. 4,667,014
U.S. Pat. No. 4,748,034
U.S. Pat. No. 5,239,660
U.S. Pat. No. 3,832,253
U.S. Pat. No. 3,854,480
U.S. Pat. No. 4,458,066.
U.S. Pat. No. 8,916,159
WO 2010/070263 A1
WO 2014/013026 A1
WO 2014/140317 A1
WO 2016/102679 A1
WO 2013/103637 A1
WO 2016/142768 A1
WO 2014/140317 A1

What is claimed is:

1. An antibody drug conjugate (ADC) having the general formula A -(L)n-(T)m, in which
   A is a fully human antibody, or antigen-binding fragment thereof, which specifically binds to the extracellular domain of receptor tyrosine kinase-like orphan receptor 2 (ROR2),
   which comprises one of the following CDR sets:
   a) heavy chain CDRs 1-3 as set forth in SEQ ID NOs 38, 39 and 40, respectively, and light chain CDRs 1 and 3 as set forth in SEQ ID NOs 29 and 41, respectively, with light chain CDR 2 having the sequence KAS;
   b) heavy chain CDRs 1-3 as set forth in SEQ ID NOs 26-28, respectively, and light chain CDRs 1-3 as set forth in SEQ ID NOs 29, 73 and 30, respectively;
   c) heavy chain CDRs 1-3 as set forth in SEQ ID NOs 94, 32 and 44, respectively, and light chain CDRs 1 and 3 as set forth in SEQ ID NOs 29 and 42, respectively, with light chain CDR 2 having the sequence KAS;
   d) heavy chain CDRs 1-3 as set forth in SEQ ID NOs 38, 46 and 52, respectively, and light chain CDRs 1 and 3 as set forth in SEQ ID NOs 50 and 53, respectively, with light chain CDR 2 having the sequence AAS;
   e) heavy chain CDRs 1-3 as set forth in SEQ ID NOs 38, 54 and 55, respectively, and light chain CDRs 1 and 3 as set forth in SEQ ID NOs 56 and 57, respectively, with light chain CDR 2 having the sequence LGS;
   f) heavy chain CDRs 1-3 as set forth in SEQ ID NOs 58-60, respectively, and light chain CDRs 1 and 3 as set forth in SEQ ID NOs 61, and 62, respectively, with light chain CDR 2 having the sequence KAS;
   g) heavy chain CDRs 1-3 as set forth in SEQ ID NOs 63-65, respectively, with light chain CDRs 1 and 3 as set forth in SEQ ID NOs 50 and 66, respectively, with light chain CDR 2 having the sequence AAS; and
   L is a linker,
   T is a cytotoxic or cytostatic payload,
   and in which n and m are integers between >1 and <10.

2. The conjugate according to claim 1, wherein the linker comprises, or consists of at least one selected from the group consisting of
   an oligopeptide linker
   a maleimide linker, optionally comprising cleavable spacers, that can be cleaved by changes in pH, redox potential and or specific intracellular enzymes.

3. The conjugate according to claim 1, wherein the linker has at least one of the following amino acid sequences: -LPXTGn-, -LPXAGn-, -LPXSGn-, -LAXTGn-, -LPXTAn- or -NPQTGn-, with Gn being an oligo- or polyglycine with n being an integer between ≥1 and ≤21, An being an oligo- or polyalanine with n being an integer between ≥1 and ≤21, and X being any conceivable amino acid.

4. The conjugate according to claim 1, wherein, prior to conjugation,
   the antibody, or antigen-binding fragment thereof bears a sortase recognition motif fused or conjugated to the C-terminus of the antibody, or antigen-binding fragment thereof, and
   the toxin comprises a glycine stretch with a length of between ≥1 and ≤21 glycine residues.

5. The antibody drug conjugate according to claim 1, wherein the toxin is at least one selected from the group consisting of:
   maytansinoid,
   auristatin,
   anthracycline,
   calcheamicin,
   tubulysin,
   duocarmycin,
   radioisotope,
   liposome comprising a toxic payload,
   protein toxin,
   taxane,
   indilino-benzodiazepine pseudodimer, and
   pyrrolobenzodiazepine.

6. The conjugate according to claim 1, which is created by sortase-mediated conjugation of (i) an antibody carrying one or more sortase recognition motifs and (ii) one or more toxins carrying an oligoglycine tag.

7. An antibody drug conjugate (ADC) having the general formula A -(L)n-(T)m, in which A is a fully human antibody, or antigen-binding fragment thereof, which specifically binds to the extracellular domain of receptor tyrosine kinase-like orphan receptor 2 (ROR2), wherein said antibody or antigen-binding fragment thereof comprises an Ig heavy chain variable region sequence and an Ig light chain variable region sequence, respectively, shown in:
(i) SEQ ID NO:2 and SEQ ID NO:3;
(ii) SEQ ID NO:4 and SEQ ID NO:5;
(iii) SEQ ID NO:6 and SEQ ID NO:7;
(iv) SEQ ID NO:8 and SEQ ID NO:9;
(v) SEQ ID NO:10 and SEQ ID NO:11;
(vi) SEQ ID NO: 12 and SEQ ID NO: 13;
(vii) SEQ ID NO:14 and SEQ ID NO:15;
(vii) SEQ ID NO: 16 and SEQ ID NO: 17;
(ix) SEQ ID NO: 18 and SEQ ID NO:19;
(x) SEQ ID NO:20 and SEQ ID NO:21;
(xi) SEQ ID NO:22 and SEQ ID NO:23; or
(xii) SEQ ID NO:24 and SEQ ID NO:25; and
L is a linker,
T is a cytotoxic or cytostatic payload,
and in which n and m are integers between >1 and <10.

8. An antibody drug conjugate (ADC) having the general formula A -(L)n-(T)m, in which
A is the antibody, or antigen-binding fragment thereof, according to claim 1, which comprises one of the following sequence pairs:
a) the heavy chain variable region sequence of antibody GK-5A1 shown in SEQ ID NO. 8 and the light chain variable region sequence of antibody GK-5A1 shown in SEQ ID NO. 9,
b) the heavy chain variable region sequence of antibody MK-3B12 shown in SEQ ID NO. 2 and the light chain variable region sequence of antibody MK-3B12 shown in SEQ ID NO. 3,
c) the heavy chain variable region sequence of antibody GK-5E1 shown in SEQ ID NO. 12 and the light chain variable region sequence of antibody GK-5E1 shown in SEQ ID NO. 13,
d) the heavy chain variable region sequence of antibody GK-21D3 shown in SEQ ID NO. 18 and the light chain variable region sequence of antibody GK-5E1 shown in SEQ ID NO. 19,
e) the heavy chain variable region sequence of antibody MK-24C10 shown in SEQ ID NO. 20 and the light chain variable region sequence of antibody MK-24C10 shown in SEQ ID NO. 21,
f) the heavy chain variable region sequence of antibody MK-24F9 shown in SEQ ID NO. 22 and the light chain variable region sequence of antibody MK-24F9 shown in SEQ ID NO. 23,
g) the heavy chain variable region sequence of antibody GK-22G12 shown in SEQ ID NO. 24 and the light chain variable region sequence of antibody GK-22G12 shown in SEQ ID NO. 25, and
L is a linker,
T is a cytotoxic or cytostatic payload,
and in which n and m are integers between >1 and <10.

9. The antibody drug conjugate according to claim 5, wherein the anthracycline is PNU-159682 derived anthracycline.

* * * * *

```
                             SEQUENCE LISTING

Sequence total quantity: 142
SEQ ID NO: 1            moltype = AA  length = 370
FEATURE                 Location/Qualifiers
REGION                  1..370
                        note = synthetic construct; peptide
source                  1..370
                        mol_type = protein
                        organism = synthetic construct
SEQUENCE: 1
EVEVLDPNDP LGPLDGQDGP IPTLKGYFLN FLEPVNNITI VQGQTAILHC KVAGNPPPNV   60
RWLKNDAPVV QEPRRIIIRK TEYGSRLRIQ DLDTTDTGYY QCVATNGMKT ITATGVLFVR  120
LGPTHSPNHN FQDDYHEDGF CQPYRGIACA RFIGNRTIYV DSLQMQGEIE NRITAAFTMI  180
GTSTHLSDQC SQFAIPSFCH FVFPLCDARS RTPKPRELCR DECEVLESDL CRQEYTIARS  240
NPLILMRLQL PKCEALPMPE SPDAANCMRI GIPAERLGRY HQCYNGSGMD YRGTASTTKS  300
GHQCQPWALQ HPHSHHLSST DFPELGGGHA YCRNPGGQME GPWCFTQNKN VRMELCDVPS  360
CSPRDSSKMG                                                        370

SEQ ID NO: 2            moltype = AA  length = 450
FEATURE                 Location/Qualifiers
REGION                  1..450
                        note = synthetic construct; peptide
source                  1..450
                        mol_type = protein
                        organism = synthetic construct
SEQUENCE: 2
EVQLVESGPG LLKPSETLSL TCAVSGYSIS SGYYWGWIRQ PPGKGLEWIG SIYQSGSTHY   60
NPSLKSRVTI SVDTSKNQFS LKLTSVTAAD TAVYYCARED RAGWYPFDCW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGR                                  450

SEQ ID NO: 3            moltype = AA  length = 213
FEATURE                 Location/Qualifiers
REGION                  1..213
                        note = synthetic construct; peptide
source                  1..213
                        mol_type = protein
                        organism = synthetic construct
SEQUENCE: 3
DIVMTQSPST LSASVGDRVT ITCRASQSIS SWLAWYQQKP GKAPKLLIYK ASSLESGVPS   60
RFSGSGSGTE FTLTISSLQP DDFATYYCQQ YNNYWTFGQG TKVEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                              213

SEQ ID NO: 4            moltype = AA  length = 448
FEATURE                 Location/Qualifiers
REGION                  1..448
                        note = synthetic construct; peptide
source                  1..448
                        mol_type = protein
                        organism = synthetic construct
SEQUENCE: 4
EVQLLETGGG VVQPGRSLRL SCVASGFTFR SHGMHWVRQA PGKGLEWVAL IWYDGSKKYY   60
```

```
ADSVKGRFTI SRDNSKNTLY LQMNSLRAED TAVYYCARVG AGLYLDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPSRDELT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGK                                     448

SEQ ID NO: 5             moltype = AA  length = 214
FEATURE                  Location/Qualifiers
REGION                   1..214
                         note = synthetic construct; peptide
source                   1..214
                         mol_type = protein
                         organism = synthetic construct
SEQUENCE: 5
AIRMTQSPST LSASVGDRVT ITCRASQTIS NWLAWFQQKP GKAPKVLIYK ASSLESGVPS     60
RFSGSGSGTE FTLTISSLQP DDFASYYCQQ YNSYSYTFGQ GTRLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 6             moltype = AA  length = 449
FEATURE                  Location/Qualifiers
REGION                   1..449
                         note = synthetic construct; peptide
source                   1..449
                         mol_type = protein
                         organism = synthetic construct
SEQUENCE: 6
EVQLVESGGG VVQPGRSLRL SCAASGFTFR SYGMHWVRQA PGKGLEWVAI IWYDGSKKYY     60
TDSVQGRFTI SRDNSKNTLY LQMNSLRAED TAVYYCARPG IAMTGLDYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                    449

SEQ ID NO: 7             moltype = AA  length = 213
FEATURE                  Location/Qualifiers
REGION                   1..213
                         note = synthetic construct; peptide
source                   1..213
                         mol_type = protein
                         organism = synthetic construct
SEQUENCE: 7
DIQLTQSPST LSASVGDRVT ITCRASQSIS SWLAWYQQKP GKAPKLLIYK ASSLESGVPS     60
RFSGSGSGTE FTLTISSLQP DDFATYYCQQ YNNYWTFGQG TKVEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                213

SEQ ID NO: 8             moltype = AA  length = 453
FEATURE                  Location/Qualifiers
REGION                   1..453
                         note = synthetic construct; peptide
source                   1..453
                         mol_type = protein
                         organism = synthetic construct
SEQUENCE: 8
QVQLVESGGG VVQPGRSLRL SCAASGFTFS SYGMYWVRQA PGKGLEWVAV IWNDGSNKYY     60
ADSVKGRFTI SRDNSKNTLY LQMNSLRAED TAVYYCAREG SGWYDYYYGM DVWGQGTTVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEL    240
LGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGK                                453

SEQ ID NO: 9             moltype = AA  length = 213
FEATURE                  Location/Qualifiers
REGION                   1..213
                         note = synthetic construct; peptide
source                   1..213
                         mol_type = protein
                         organism = synthetic construct
SEQUENCE: 9
EIVLTQSPST LSASVGDRVT ITCRASQSIS SWLAWYQQKP GKAPKLLIYK ASSLESGVPS     60
RFSGSGSGTE FTLTISSLQP DDFATYYCQQ YNSYWTFGQG TKVDIKRTVA APSVFIFPPS    120
DEQLKSGTAS VVCLLNNFYP REAKVQWKVD NALQSGNSQE SVTEQDSKDS TYSLSSTLTL    180
```

SKADYEKHKV YACEVTHQGL SSPVTKSFNR GEC                                    213

SEQ ID NO: 10              moltype = AA  length = 449
FEATURE                    Location/Qualifiers
REGION                     1..449
                           note = synthetic construct; peptide
source                     1..449
                           mol_type = protein
                           organism = synthetic construct
SEQUENCE: 10
QVQLQESGGG VVQPGRSLRL SCAASGFTFR SYGMHWVRQA PGKGLEWVAI IWYDGSKKYY        60
TDSVKGRFTI SRDNSKNTLY LQMNSLRAED TAVYYCARPG VAMTGLDLWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYNS       300
TYRVVSVLTV LHQDWLNGKE YKCKVSNKAL PAPIEKTISK AKGQPREPQV YTLPPSRDEL       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPGK                                        449

SEQ ID NO: 11              moltype = AA  length = 213
FEATURE                    Location/Qualifiers
REGION                     1..213
                           note = synthetic construct; peptide
source                     1..213
                           mol_type = protein
                           organism = synthetic construct
SEQUENCE: 11
EIVMTQSPST LSASVGDRVT ITCRASQSIS SWLAWYQQKP GKAPKLLIYK ASSLESGVPS        60
RFSGSGSGTE FTLTISSLQP DDFATYYCQQ YNNYWTFGQG TKVDIKRTVA APSVFIFPPS       120
DEQLKSGTAS VVCLLNNFYP REAKVQWKVD NALQSGNSQE SVTEQDSKDS TYSLSSTLTL       180
SKADYEKHKV YACEVTHQGL SSPVTKSFNR GEC                                    213

SEQ ID NO: 12              moltype = AA  length = 449
FEATURE                    Location/Qualifiers
REGION                     1..449
                           note = synthetic construct; peptide
source                     1..449
                           mol_type = protein
                           organism = synthetic construct
SEQUENCE: 12
QVTLKESGGD VVQPGRSLRL SCAASGFTFR TYGMHWVRQA PGKGPEWVAL IWYDGSKKYY        60
ADSVKGRFTI SRDNSKNTLY LQMNSLRAED TAVYYCVRVR FGELYFQHWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYNS       300
TYRVVSVLTV LHQDWLNGKE YKCKVSNKAL PAPIEKTISK AKGQPREPQV YTLPPSRDEL       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPGK                                        449

SEQ ID NO: 13              moltype = AA  length = 214
FEATURE                    Location/Qualifiers
REGION                     1..214
                           note = synthetic construct; peptide
source                     1..214
                           mol_type = protein
                           organism = synthetic construct
SEQUENCE: 13
DIVMTQSPST LSASVGDRVT ITCRASQSIS SWLAWYQQKP GKAPKLLIYK ASSLESGVPS        60
RFSGSGSGTE FTLTISSLQP DDFATYYCQQ YNSYSYSFGQ GTKLEIKRTV AAPSVFIFPP       120
SDEQLKSGTA SVVCLLNNFY PREAKVQWKV DNALQSGNSQ ESVTEQDSKD STYSLSSTLT       180
LSKADYEKHK VYACEVTHQG LSSPVTKSFN RGEC                                   214

SEQ ID NO: 14              moltype = AA  length = 448
FEATURE                    Location/Qualifiers
REGION                     1..448
                           note = synthetic construct; peptide
source                     1..448
                           mol_type = protein
                           organism = synthetic construct
SEQUENCE: 14
QVQLVESGGG VVQPGRSLRL SCAASGFTFS RYGMHWVRQA PGKGLEWVAL IWYDGSNKYY        60
ADSVKGRFTI SRDNSKNTLY LQMNSLRAED TAVYYCARVA AALHFHYWGQ GTLVTVSSAS       120
TKGPSVFPLA PSSKSTSGGT AALGCLVKDY FPEPVTVSWN SGALTSGVHT FPAVLQSSGL       180
YSLSSVVTVP SSSLGTQTYI CNVNHKPSNT KVDKKVEPKS CDKTHTCPPC PAPELLGGPS       240
VFLFPPKPKD TLMISRTPEV TCVVVDVSHE DPEVKFNWYV DGVEVHNAKT KPREEQYNST       300
YRVVSVLTVL HQDWLNGKEY KCKVSNKALP APIEKTISKA KGQPREPQVY TLPPSRDELT       360
KNQVSLTCLV KGFYPSDIAV EWESNGQPEN NYKTTPPVLD SDGSFFLYSK LTVDKSRWQQ       420
GNVFSCSVMH EALHNHYTQK SLSLSPGK                                         448

```
SEQ ID NO: 15            moltype = AA   length = 214
FEATURE                  Location/Qualifiers
REGION                   1..214
                         note = synthetic construct; peptide
source                   1..214
                         mol_type = protein
                         organism = synthetic construct
SEQUENCE: 15
DIVMTQSPST LSASVGDRVT ITCRASQSID NWLAWYQQKP GKAPKVLIYK ASSLESGVPS   60
RFSGSGSGTE FTLTISSLQP DDFATYYCQQ YNSYSYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 16            moltype = AA   length = 449
FEATURE                  Location/Qualifiers
REGION                   1..449
                         note = synthetic construct; peptide
source                   1..449
                         mol_type = protein
                         organism = synthetic construct
SEQUENCE: 16
QITLKESGGG VVQPGRSLRL SCAASGFTFR TYGMHWVRQA PGKGLEWVAL IWYDGSNKYY   60
ADSVKGRFTI SRDNSKNTLY LQMNSLRAED TAVYYCIRVK FGDLYFQHWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 17            moltype = AA   length = 214
FEATURE                  Location/Qualifiers
REGION                   1..214
                         note = synthetic construct; peptide
source                   1..214
                         mol_type = protein
                         organism = synthetic construct
SEQUENCE: 17
EIVLTQSPSS LSASVGDRVT ITCRASQGIS NYLAWYQQKP GKVPKLLIYA ASTLQSGVPS   60
RFSGSGSGTD FTLTISSLQP EDVATYYCQK YNSAPYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 18            moltype = AA   length = 452
FEATURE                  Location/Qualifiers
REGION                   1..452
                         note = synthetic construct; peptide
source                   1..452
                         mol_type = protein
                         organism = synthetic construct
SEQUENCE: 18
QVQLVQSGGG VVQPGRSLRL SCAASGFTFS SYGMHWVRQA PGKGLEWVAI IWYDGSNKYY   60
ADSVKGRFTI SRDNSKNTLY LQMNSLRDED TAVYYCARMG AINRGGGFD YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 19            moltype = AA   length = 214
FEATURE                  Location/Qualifiers
REGION                   1..214
                         note = synthetic construct; peptide
source                   1..214
                         mol_type = protein
                         organism = synthetic construct
SEQUENCE: 19
DIQLTQSPSS LSASIGDRVT ITCRASQGIS NYLAWYQQKP GKVPKLLIYA ASTLQSGVPS   60
RFSGSGSGTD FTLTISSLQP EDVSTYYCQK YNSAPWTFGQ GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 20            moltype = AA   length = 457
FEATURE                  Location/Qualifiers
REGION                   1..457
                         note = synthetic construct; peptide
source                   1..457
                         mol_type = protein
```

```
                         organism = synthetic construct
SEQUENCE: 20
QVQLVESGGG  VVQPGRSLRL  SCAASGFTFS  SYGMHWVRQA  PGKGLEWVAV  IWFDGTNKHY   60
ADSVKGRFTI  SRDNSKNTLY  LQMNSLRAED  TAVYYCARDK  GEWFGELRYY  YYGMDVWGQG  120
TTVTVSSAST  KGPSVFPLAP  SSKSTSGGTA  ALGCLVKDYF  PEPVTVSWNS  GALTSGVHTF  180
PAVLQSSGLY  SLSSVVTVPS  SSLGTQTYIC  NVNHKPSNTK  VDKKVEPKSC  DKTHTCPPCP  240
APELLGGPSV  FLFPPKPKDT  LMISRTPEVT  CVVVDVSHED  PEVKFNWYVD  GVEVHNAKTK  300
PREEQYNSTY  RVVSVLTVLH  QDWLNGKEYK  CKVSNKALPA  PIEKTISKAK  GQPREPQVYT  360
LPPSRDELTK  NQVSLTCLVK  GFYPSDIAVE  WESNGQPENN  YKTTPPVLDS  DGSFFLYSKL  420
TVDKSRWQQG  NVFSCSVMHE  ALHNHYTQKS  LSLSPGK                             457

SEQ ID NO: 21            moltype = AA  length = 219
FEATURE                  Location/Qualifiers
REGION                   1..219
                         note = synthetic construct; peptide
source                   1..219
                         mol_type = protein
                         organism = synthetic construct
SEQUENCE: 21
EIVLTQSPLS  LPVTPGEPAS  ISCRSSQSLL  HSNGYNYLDW  YLQKPGQSPQ  LLIYLGSNRA   60
SGVPDRFSGS  GSGTDFTLKI  SRVEAEDVGV  YYCMQALQTP  YTFGQGTKLE  IKRTVAAPSV  120
FIFPPSDEQL  KSGTASVVCL  LNNFYPREAK  VQWKVDNALQ  SGNSQESVTE  QDSKDSTYSL  180
SSTLTLSKAD  YEKHKVYACE  VTHQGLSSPV  TKSFNRGEC                           219

SEQ ID NO: 22            moltype = AA  length = 449
FEATURE                  Location/Qualifiers
REGION                   1..449
                         note = synthetic construct; peptide
source                   1..449
                         mol_type = protein
                         organism = synthetic construct
SEQUENCE: 22
EVQLQQWGAG  LLKPSETLSL  TCAVYGGSFS  GYYWSWIRQP  PGKGLEWIGD  INHSRTTNYN   60
PSLKSRVTIS  VDTSKNQFSL  KLSSVTAADT  AVYYCARGGE  QWLVPFDYWD  QGTLVTVSSA  120
STKGPSVFPL  APSSKSTSGG  TAALGCLVKD  YFPEPVTVSW  NSGALTSGVH  TFPAVLQSSG  180
LYSLSSVVTV  PSSSLGTQTY  ICNVNHKPSN  TKVDKKVEPK  SCDKTHTCPP  CPAPELLGGP  240
SVFLFPPKPK  DTLMISRTPE  VTCVVVDVSH  EDPEVKFNWY  VDGVEVHNAK  TKPREEQYNS  300
TYRVVSVLTV  LHQDWLNGKE  YKCKVSNKAL  PAPIEKTISK  AKGQPREPQV  YTLPPSRDEL  360
TKNQVSLTCL  VKGFYPSDIA  VEWESNGQPE  NNYKTTPPVL  DSDGSFFLYS  KLTVDKSRWQ  420
QGNVFSCSVM  HEALHNHYTQ  KSLSLSPGK                                       449

SEQ ID NO: 23            moltype = AA  length = 214
FEATURE                  Location/Qualifiers
REGION                   1..214
                         note = synthetic construct; peptide
source                   1..214
                         mol_type = protein
                         organism = synthetic construct
SEQUENCE: 23
EIVMTQSPST  LSASVGDRVT  ITCRASQSIS  HWLAWYQQKP  GKAPKLLIYK  ASSLKSGVPS   60
RFNGSGSGTE  FTLTISSLQP  DDFATYYCQH  YNTYSRTFGQ  GTKVDIKRTV  AAPSVFIFPP  120
SDEQLKSGTA  SVVCLLNNFY  PREAKVQWKV  DNALQSGNSQ  ESVTEQDSKD  STYSLSSTLT  180
LSKADYEKHK  VYACEVTHQG  LSSPVTKSFN  RGEC                                214

SEQ ID NO: 24            moltype = AA  length = 452
FEATURE                  Location/Qualifiers
REGION                   1..452
                         note = synthetic construct; peptide
source                   1..452
                         mol_type = protein
                         organism = synthetic construct
SEQUENCE: 24
EVQLVESGGG  LVQSGGSLRL  SCAASGFTFS  SQRLSWVRQA  PGKGLEWVAN  IKQDGSEKNY   60
VDSVRGRFTI  SRDIAKNSLY  LQMNSLRAED  TAVYYCARDG  YRNGWHIPED  YWGQGTLVTV  120
SSASTKGPSV  FPLAPSSKST  SGGTAALGCL  VKDYFPEPVT  VSWNSGALTS  GVHTFPAVLQ  180
SSGLYSLSSV  VTVPSSSLGT  QTYICNVNHK  PSNTKVDKKV  EPKSCDKTHT  CPPCPAPELL  240
GGPSVFLFPP  KPKDTLMISR  TPEVTCVVVD  VSHEDPEVKF  NWYVDGVEVH  NAKTKPREEQ  300
YNSTYRVVSV  LTVLHQDWLN  GKEYKCKVSN  KALPAPIEKT  ISKAKGQPRE  PQVYTLPPSR  360
DELTKNQVSL  TCLVKGFYPS  DIAVEWESNG  QPENNYKTTP  PVLDSDGSFF  LYSKLTVDKS  420
RWQQGNVFSC  SVMHEALHNH  YTQKSLSLSP  GK                                  452

SEQ ID NO: 25            moltype = AA  length = 214
FEATURE                  Location/Qualifiers
REGION                   1..214
                         note = synthetic construct; peptide
source                   1..214
                         mol_type = protein
                         organism = synthetic construct
SEQUENCE: 25
```

```
DIVMTQSPSS LSASVGDRVT ITCRASQGIS NYLAWYQQKP GKVPKLLIYA ASTLQSGVPS    60
RFSGSGSGTD FTLTISSLQP EDVSTYYCQK HNRAPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 26           moltype = AA   length = 9
FEATURE                 Location/Qualifiers
REGION                  1..9
                        note = synthetic construct; peptide
source                  1..9
                        mol_type = protein
                        organism = synthetic construct
SEQUENCE: 26
GYSISSGYY                                                             9

SEQ ID NO: 27           moltype = AA   length = 7
FEATURE                 Location/Qualifiers
REGION                  1..7
                        note = synthetic construct; peptide
source                  1..7
                        mol_type = protein
                        organism = synthetic construct
SEQUENCE: 27
IYQSGST                                                               7

SEQ ID NO: 28           moltype = AA   length = 15
FEATURE                 Location/Qualifiers
REGION                  1..15
                        note = synthetic construct; peptide
source                  1..15
                        mol_type = protein
                        organism = synthetic construct
SEQUENCE: 28
CAREDRAGWY PFDCW                                                     15

SEQ ID NO: 29           moltype = AA   length = 6
FEATURE                 Location/Qualifiers
REGION                  1..6
                        note = synthetic construct; peptide
source                  1..6
                        mol_type = protein
                        organism = synthetic construct
SEQUENCE: 29
QSISSW                                                                6

SEQ ID NO: 30           moltype = AA   length = 10
FEATURE                 Location/Qualifiers
REGION                  1..10
                        note = synthetic construct; peptide
source                  1..10
                        mol_type = protein
                        organism = synthetic construct
SEQUENCE: 30
CQQYNNYWTF                                                           10

SEQ ID NO: 31           moltype = AA   length = 8
FEATURE                 Location/Qualifiers
REGION                  1..8
                        note = synthetic construct; peptide
source                  1..8
                        mol_type = protein
                        organism = synthetic construct
SEQUENCE: 31
GFTFRSHG                                                              8

SEQ ID NO: 32           moltype = AA   length = 8
FEATURE                 Location/Qualifiers
REGION                  1..8
                        note = synthetic construct; peptide
source                  1..8
                        mol_type = protein
                        organism = synthetic construct
SEQUENCE: 32
IWYDGSKK                                                              8

SEQ ID NO: 33           moltype = AA   length = 13
FEATURE                 Location/Qualifiers
REGION                  1..13
                        note = synthetic construct; peptide
```

```
source                   1..13
                         mol_type = protein
                         organism = synthetic construct
SEQUENCE: 33
CARVGAGLYL DYW                                                          13

SEQ ID NO: 34            moltype = AA   length = 6
FEATURE                  Location/Qualifiers
REGION                   1..6
                         note = synthetic construct; peptide
source                   1..6
                         mol_type = protein
                         organism = synthetic construct
SEQUENCE: 34
QTISNW                                                                   6

SEQ ID NO: 35            moltype = AA   length = 11
FEATURE                  Location/Qualifiers
REGION                   1..11
                         note = synthetic construct; peptide
source                   1..11
                         mol_type = protein
                         organism = synthetic construct
SEQUENCE: 35
CQQYNSYSYT F                                                            11

SEQ ID NO: 36            moltype = AA   length = 8
FEATURE                  Location/Qualifiers
REGION                   1..8
                         note = synthetic construct; peptide
source                   1..8
                         mol_type = protein
                         organism = synthetic construct
SEQUENCE: 36
GFTFRSYG                                                                 8

SEQ ID NO: 37            moltype = AA   length = 14
FEATURE                  Location/Qualifiers
REGION                   1..14
                         note = synthetic construct; peptide
source                   1..14
                         mol_type = protein
                         organism = synthetic construct
SEQUENCE: 37
CARPGIAMTG LDYW                                                         14

SEQ ID NO: 38            moltype = AA   length = 8
FEATURE                  Location/Qualifiers
REGION                   1..8
                         note = synthetic construct; peptide
source                   1..8
                         mol_type = protein
                         organism = synthetic construct
SEQUENCE: 38
GFTFSSYG                                                                 8

SEQ ID NO: 39            moltype = AA   length = 8
FEATURE                  Location/Qualifiers
REGION                   1..8
                         note = synthetic construct; peptide
source                   1..8
                         mol_type = protein
                         organism = synthetic construct
SEQUENCE: 39
IWNDGSNK                                                                 8

SEQ ID NO: 40            moltype = AA   length = 18
FEATURE                  Location/Qualifiers
REGION                   1..18
                         note = synthetic construct; peptide
source                   1..18
                         mol_type = protein
                         organism = synthetic construct
SEQUENCE: 40
CAREGSGWYD YYYGMDVW                                                     18

SEQ ID NO: 41            moltype = AA   length = 10
FEATURE                  Location/Qualifiers
REGION                   1..10
```

```
                       note = synthetic construct; peptide
source                 1..10
                       mol_type = protein
                       organism = synthetic construct
SEQUENCE: 41
CQQYNSYWTF                                                                   10

SEQ ID NO: 42          moltype = AA   length = 11
FEATURE                Location/Qualifiers
REGION                 1..11
                       note = synthetic construct; peptide
source                 1..11
                       mol_type = protein
                       organism = synthetic construct
SEQUENCE: 42
CQQYNSYSYS F                                                                 11

SEQ ID NO: 43          moltype = AA   length = 14
FEATURE                Location/Qualifiers
REGION                 1..14
                       note = synthetic construct; peptide
source                 1..14
                       mol_type = protein
                       organism = synthetic construct
SEQUENCE: 43
CARPGVAMTG LDLW                                                              14

SEQ ID NO: 44          moltype = AA   length = 14
FEATURE                Location/Qualifiers
REGION                 1..14
                       note = synthetic construct; peptide
source                 1..14
                       mol_type = protein
                       organism = synthetic construct
SEQUENCE: 44
CVRVRFGELY FQHW                                                              14

SEQ ID NO: 45          moltype = AA   length = 8
FEATURE                Location/Qualifiers
REGION                 1..8
                       note = synthetic construct; peptide
source                 1..8
                       mol_type = protein
                       organism = synthetic construct
SEQUENCE: 45
GFTFSRYG                                                                      8

SEQ ID NO: 46          moltype = AA   length = 8
FEATURE                Location/Qualifiers
REGION                 1..8
                       note = synthetic construct; peptide
source                 1..8
                       mol_type = protein
                       organism = synthetic construct
SEQUENCE: 46
IWYDGSNK                                                                      8

SEQ ID NO: 47          moltype = AA   length = 13
FEATURE                Location/Qualifiers
REGION                 1..13
                       note = synthetic construct; peptide
source                 1..13
                       mol_type = protein
                       organism = synthetic construct
SEQUENCE: 47
CARVAAALHF HYW                                                               13

SEQ ID NO: 48          moltype = AA   length = 6
FEATURE                Location/Qualifiers
REGION                 1..6
                       note = synthetic construct; peptide
source                 1..6
                       mol_type = protein
                       organism = synthetic construct
SEQUENCE: 48
QSIDNW                                                                        6

SEQ ID NO: 49          moltype = AA   length = 14
FEATURE                Location/Qualifiers
```

```
REGION                  1..14
                        note = synthetic construct; peptide
source                  1..14
                        mol_type = protein
                        organism = synthetic construct
SEQUENCE: 49
CIRVKFGDLY FQHW                                                       14

SEQ ID NO: 50           moltype = AA  length = 6
FEATURE                 Location/Qualifiers
REGION                  1..6
                        note = synthetic construct; peptide
source                  1..6
                        mol_type = protein
                        organism = synthetic construct
SEQUENCE: 50
QGISNY                                                                6

SEQ ID NO: 51           moltype = AA  length = 11
FEATURE                 Location/Qualifiers
REGION                  1..11
                        note = synthetic construct; peptide
source                  1..11
                        mol_type = protein
                        organism = synthetic construct
SEQUENCE: 51
CQKYNSAPYT F                                                          11

SEQ ID NO: 52           moltype = AA  length = 17
FEATURE                 Location/Qualifiers
REGION                  1..17
                        note = synthetic construct; peptide
source                  1..17
                        mol_type = protein
                        organism = synthetic construct
SEQUENCE: 52
CARMGAINRG GGGFDYW                                                    17

SEQ ID NO: 53           moltype = AA  length = 11
FEATURE                 Location/Qualifiers
REGION                  1..11
                        note = synthetic construct; peptide
source                  1..11
                        mol_type = protein
                        organism = synthetic construct
SEQUENCE: 53
CQKYNSAPWT F                                                          11

SEQ ID NO: 54           moltype = AA  length = 8
FEATURE                 Location/Qualifiers
REGION                  1..8
                        note = synthetic construct; peptide
source                  1..8
                        mol_type = protein
                        organism = synthetic construct
SEQUENCE: 54
IWFDGTNK                                                              8

SEQ ID NO: 55           moltype = AA  length = 22
FEATURE                 Location/Qualifiers
REGION                  1..22
                        note = synthetic construct; peptide
source                  1..22
                        mol_type = protein
                        organism = synthetic construct
SEQUENCE: 55
CARDKGEWFG ELRYYYYGMD VW                                              22

SEQ ID NO: 56           moltype = AA  length = 11
FEATURE                 Location/Qualifiers
REGION                  1..11
                        note = synthetic construct; peptide
source                  1..11
                        mol_type = protein
                        organism = synthetic construct
SEQUENCE: 56
QSLLHSNGYN Y                                                          11

SEQ ID NO: 57           moltype = AA  length = 11
```

```
                        -continued

FEATURE              Location/Qualifiers
REGION               1..11
                     note = synthetic construct; peptide
source               1..11
                     mol_type = protein
                     organism = synthetic construct
SEQUENCE: 57
CMQALQTPYT F                                                             11

SEQ ID NO: 58        moltype = AA   length = 8
FEATURE              Location/Qualifiers
REGION               1..8
                     note = synthetic construct; peptide
source               1..8
                     mol_type = protein
                     organism = synthetic construct
SEQUENCE: 58
GGSFSGYY                                                                  8

SEQ ID NO: 59        moltype = AA   length = 7
FEATURE              Location/Qualifiers
REGION               1..7
                     note = synthetic construct; peptide
source               1..7
                     mol_type = protein
                     organism = synthetic construct
SEQUENCE: 59
INHSRTT                                                                   7

SEQ ID NO: 60        moltype = AA   length = 15
FEATURE              Location/Qualifiers
REGION               1..15
                     note = synthetic construct; peptide
source               1..15
                     mol_type = protein
                     organism = synthetic construct
SEQUENCE: 60
CARGGEQWLV PFDYW                                                         15

SEQ ID NO: 61        moltype = AA   length = 6
FEATURE              Location/Qualifiers
REGION               1..6
                     note = synthetic construct; peptide
source               1..6
                     mol_type = protein
                     organism = synthetic construct
SEQUENCE: 61
QSISHW                                                                    6

SEQ ID NO: 62        moltype = AA   length = 11
FEATURE              Location/Qualifiers
REGION               1..11
                     note = synthetic construct; peptide
source               1..11
                     mol_type = protein
                     organism = synthetic construct
SEQUENCE: 62
CQHYNTYSRT F                                                             11

SEQ ID NO: 63        moltype = AA   length = 8
FEATURE              Location/Qualifiers
REGION               1..8
                     note = synthetic construct; peptide
source               1..8
                     mol_type = protein
                     organism = synthetic construct
SEQUENCE: 63
GFTFSSQR                                                                  8

SEQ ID NO: 64        moltype = AA   length = 8
FEATURE              Location/Qualifiers
REGION               1..8
                     note = synthetic construct; peptide
source               1..8
                     mol_type = protein
                     organism = synthetic construct
SEQUENCE: 64
IKQDGSEK                                                                  8
```

```
SEQ ID NO: 65          moltype = AA   length = 17
FEATURE                Location/Qualifiers
REGION                 1..17
                       note = synthetic construct; peptide
source                 1..17
                       mol_type = protein
                       organism = synthetic construct
SEQUENCE: 65
CARDGYRNGW HIPEDYW                                                  17

SEQ ID NO: 66          moltype = AA   length = 11
FEATURE                Location/Qualifiers
REGION                 1..11
                       note = synthetic construct; peptide
source                 1..11
                       mol_type = protein
                       organism = synthetic construct
SEQUENCE: 66
CQKHNRAPWT F                                                        11

SEQ ID NO: 67          moltype =    length =
SEQUENCE: 67
000

SEQ ID NO: 68          moltype = AA   length = 8
FEATURE                Location/Qualifiers
REGION                 1..8
                       note = synthetic construct; peptide
SITE                   2
                       note = Xaa - Xaa = W or K
SITE                   3
                       note = Xaa - Xaa = Y, N, F or Q
SITE                   6
                       note = Xaa - Xaa = S or T
SITE                   7
                       note = Xaa - Xaa = K, N or E
source                 1..8
                       mol_type = protein
                       organism = synthetic construct
SEQUENCE: 68
IXXDGXXK                                                             8

SEQ ID NO: 69          moltype =    length =
SEQUENCE: 69
000

SEQ ID NO: 70          moltype =    length =
SEQUENCE: 70
000

SEQ ID NO: 71          moltype = AA   length = 8
FEATURE                Location/Qualifiers
REGION                 1..8
                       note = synthetic construct; peptide
SITE                   5
                       note = Xaa - Xaa=R or S
SITE                   6
                       note = Xaa - Xaa=S or T
source                 1..8
                       mol_type = protein
                       organism = synthetic construct
SEQUENCE: 71
GFTFXXYG                                                             8

SEQ ID NO: 72          moltype =    length =
SEQUENCE: 72
000

SEQ ID NO: 73          moltype =    length =
SEQUENCE: 73
000

SEQ ID NO: 74          moltype =    length =
SEQUENCE: 74
000

SEQ ID NO: 75          moltype = AA   length = 449
FEATURE                Location/Qualifiers
REGION                 1..449
```

```
                              note = synthetic construct; peptide
source                        1..449
                              mol_type = protein
                              organism = synthetic construct
SEQUENCE: 75
EVQLLESGGG VVQPGRSLRL SCAASGFTFR SYGMHWVRQA PGKGLEWVAI IWYDGSKKYY    60
TDSVKGRFTI SRDNSKNTLY LQMNSLRAED TAVYYCARPG IAMTGLDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 76                 moltype = AA  length = 213
FEATURE                       Location/Qualifiers
REGION                        1..213
                              note = synthetic construct; peptide
source                        1..213
                              mol_type = protein
                              organism = synthetic construct
SEQUENCE: 76
EIVMTQSPST LSASVGDRVT ITCRASQSIS SWLAWYQQKP GKAPKLLIYK ASSLESGVPS    60
RFSGSGSGTE FTLTISSLQP DDFATYYCQQ YNNYWTFGQG TKLEIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 77                 moltype = AA  length = 449
FEATURE                       Location/Qualifiers
REGION                        1..449
                              note = synthetic construct; peptide
source                        1..449
                              mol_type = protein
                              organism = synthetic construct
SEQUENCE: 77
QVQLVQSGGG VVQPGRSLRL SCAASGFTFR SYGMHWVRQA PGKGLEWVAI IWYDGSKKYY    60
TDSVKGRFTI SRDNSKNTLY LQMNSLRAED TAVYYCARPG VAMTGLDLWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 78                 moltype = AA  length = 213
FEATURE                       Location/Qualifiers
REGION                        1..213
                              note = synthetic construct; peptide
source                        1..213
                              mol_type = protein
                              organism = synthetic construct
SEQUENCE: 78
EIVLTQSPST LSASVGDRVT ITCRASQSIS SWLAWYQQKP GKAPKLLIYK ASSLESGVPS    60
RFSGSGSGTE FTLTISSLQP DDFATYYCQQ YNNYWTFGQG TKVDIKRTVA APSVFIFPPS   120
DEQLKSGTAS VVCLLNNFYP REAKVQWKVD NALQSGNSQE SVTEQDSKDS TYSLSSTLTL   180
SKADYEKHKV YACEVTHQGL SSPVTKSFNR GEC                                213

SEQ ID NO: 79                 moltype = AA  length = 449
FEATURE                       Location/Qualifiers
REGION                        1..449
                              note = synthetic construct; peptide
source                        1..449
                              mol_type = protein
                              organism = synthetic construct
SEQUENCE: 79
EVQLQESGGG VVQPGRSLRL SCAASGFTFR TYGMHWVRQA PGKGLEWVAL IWYDGSNKYY    60
ADSVKGRFTI SRDNSKNTLY LQMNSLRAED TAVYYCIRVK FGDLYFQHWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 80                 moltype = AA  length = 214
FEATURE                       Location/Qualifiers
REGION                        1..214
                              note = synthetic construct; peptide
source                        1..214
```

```
                        mol_type = protein
                        organism = synthetic construct
SEQUENCE: 80
DVVMTQSPST LSASVGDRVT ITCRASQSIS SWLAWYQQKP GKAPKLLIYK ASSLESGVPS   60
RFSGSGSGTE FTLTISSLQP DDFATYYCQQ YNSYSYTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 81           moltype = AA  length = 452
FEATURE                 Location/Qualifiers
REGION                  1..452
                        note = synthetic construct; peptide
source                  1..452
                        mol_type = protein
                        organism = synthetic construct
SEQUENCE: 81
QVQLVQSGGG VVQPGRSLRL SCAASGFTFS SYGMHWVRQA PGKGLEWVAI IWYDGSNKYY   60
ADSVKGRFTI SRDNSKNTLY LQMNSLRDED TAVYYCARMG AINRGGGFD YWGQGTLVTV   120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 82           moltype = AA  length = 214
FEATURE                 Location/Qualifiers
REGION                  1..214
                        note = synthetic construct; peptide
source                  1..214
                        mol_type = protein
                        organism = synthetic construct
SEQUENCE: 82
DIQLTQSPSS LSASIGDRVT ITCRASQGIS NYLAWYQQKP GKVPKLLIYA ASTLQSGVPS   60
RFSGSGSGTD FTLTISSLQP EDVSTYYCQK YNSAPWTFGQ GTKVDIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 83           moltype = AA  length = 457
FEATURE                 Location/Qualifiers
REGION                  1..457
                        note = synthetic construct; peptide
source                  1..457
                        mol_type = protein
                        organism = synthetic construct
SEQUENCE: 83
EVQLVESGGG VVQPGRSLRL SCAASGFTFS SYGMHWVRQA PGKGLEWVAV IWFDGTNKHY   60
ADSVKGRFTI SRDNSKNTLY LQMNSLRAED TAVYYCARDK GEWFGELRYY YYGMDVWGQG  120
TTVTVSSAST KGPSVFPLAP SSKSTSGGTA ALGCLVKDYF PEPVTVSWNS GALTSGVHTF  180
PAVLQSSGLY SLSSVVTVPS SSLGTQTYIC NVNHKPSNTK VDKKVEPKSC DKTHTCPPCP  240
APELLGGPSV FLFPPKPKDT LMISRTPEVT CVVVDVSHED PEVKFNWYVD GVEVHNAKTK  300
PREEQYNSTY RVVSVLTVLH QDWLNGKEYK CKVSNKALPA PIEKTISKAK GQPREPQVYT  360
LPPSRDELTK NQVSLTCLVK GFYPSDIAVE WESNGQPENN YKTTPPVLDS DGSFFLYSKL  420
TVDKSRWQQG NVFSCSVMHE ALHNHYTQKS LSLSPGK                           457

SEQ ID NO: 84           moltype = AA  length = 219
FEATURE                 Location/Qualifiers
REGION                  1..219
                        note = synthetic construct; peptide
source                  1..219
                        mol_type = protein
                        organism = synthetic construct
SEQUENCE: 84
EIVLTQSPLS LPVTPGEPAS ISCRSSQSLL HSNGYNYLDW YLQKPGQSPQ LLIYLGSNRA   60
SGVPDRFSGS GSGTDFTLKI SRVEAEDVGV YYCMQALQTP YTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 85           moltype = AA  length = 449
FEATURE                 Location/Qualifiers
REGION                  1..449
                        note = synthetic construct; peptide
source                  1..449
                        mol_type = protein
                        organism = synthetic construct
SEQUENCE: 85
QVQLQQWGAG LLKPSETLSL TCAVYGGSFS GYYWSWIRQP PGKGLEWIGE INHSGITNYN   60
PSLKSRLTVS VDTSKNQFSL KLSSVTAADT AVYYCARGGD QWLVPFDNWG QGTLVTVSSA  120
STKGPSVFPL APSSKSTSGG TAALGCLVKD YFPEPVTVSW NSGALTSGVH TFPAVLQSSG  180
```

```
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                     449

SEQ ID NO: 86           moltype = AA  length = 214
FEATURE                 Location/Qualifiers
REGION                  1..214
                        note = synthetic construct; peptide
source                  1..214
                        mol_type = protein
                        organism = synthetic construct
SEQUENCE: 86
DIVMTQSPSS LSASVGDRVT ITCRASQGIS NYLAWYQQKP GKVPKLLIYA ASTLQSGVPS    60
RFSGSGSGTD FTLTISSLQP EDVSTYYCQK HNRAPWTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 87           moltype = AA  length = 449
FEATURE                 Location/Qualifiers
REGION                  1..449
                        note = synthetic construct; peptide
source                  1..449
                        mol_type = protein
                        organism = synthetic construct
SEQUENCE: 87
QVQLQQWGAG LLKPSETLSL TCAVYGGSFS GYYWSWIRQP PGKGLEWIGE INHSGITNYN    60
PSLKSRLTVS VDTSKNQFSL KLSSVTAADT AVYYCARGGD QWLVPFDNWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYNS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                     449

SEQ ID NO: 88           moltype = AA  length = 214
FEATURE                 Location/Qualifiers
REGION                  1..214
                        note = synthetic construct; peptide
source                  1..214
                        mol_type = protein
                        organism = synthetic construct
SEQUENCE: 88
EIVMTQSPST LSASVGDRVT ITCRASQSIS HWLAWYQQKP GKAPKLLIYK ASSLKSGVPS    60
RFNGSGSGTE FTLTISSLQP DDFATYYCQH YNTYSRTFGQ GTKVDIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 89           moltype = AA  length = 452
FEATURE                 Location/Qualifiers
REGION                  1..452
                        note = synthetic construct; peptide
source                  1..452
                        mol_type = protein
                        organism = synthetic construct
SEQUENCE: 89
RVQLVQSGGG LVQSGGSLRL SCAASGFTFS SQRLSWVRQA PGKGLEWVAN IKQDGSEKNY    60
VDSVRGRFTI SRDIAKNSLY LQMNSLRAED TAVYYCARDG YRNGWHIPED YWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                 452

SEQ ID NO: 90           moltype = AA  length = 214
FEATURE                 Location/Qualifiers
REGION                  1..214
                        note = synthetic construct; peptide
source                  1..214
                        mol_type = protein
                        organism = synthetic construct
SEQUENCE: 90
DVVMTQSPSS LSASVGDRVT ITCRASQGIS NYLAWYQQKP GKVPKLLIYA ASTLQSGVPS    60
RFSGSGSGTD FTLTISSLQP EDVSTYYCQK HNRAPWTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214
```

```
SEQ ID NO: 91              moltype = AA  length = 452
FEATURE                    Location/Qualifiers
REGION                     1..452
                           note = synthetic construct; peptide
source                     1..452
                           mol_type = protein
                           organism = synthetic construct
SEQUENCE: 91
EVQLLESGGG LVQSGGSLRL SCAASGFTFS SQRLSWVRQA PGKGLEWVAN IKQDGSEKNY   60
VDSVRGRFTI SRDIAKNSLY LQMNSLRAED TAVYYCARDG YRNGWHIPED YWGQGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 92              moltype = AA  length = 214
FEATURE                    Location/Qualifiers
REGION                     1..214
                           note = synthetic construct; peptide
source                     1..214
                           mol_type = protein
                           organism = synthetic construct
SEQUENCE: 92
AIRMTQSPSS LSASVGDRVT ITCRASQGIS NYLAWYQQKP GKVPKLLIYA ASTLQSGVPS   60
RFSGSGSGTD FTLTISSLQP EDVSTYYCQK HNRAPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 93              moltype = AA  length = 7
FEATURE                    Location/Qualifiers
REGION                     1..7
                           note = synthetic construct; peptide
source                     1..7
                           mol_type = protein
                           organism = synthetic construct
SEQUENCE: 93
INHSGIT                                                              7

SEQ ID NO: 94              moltype = AA  length = 8
FEATURE                    Location/Qualifiers
REGION                     1..8
                           note = synthetic construct; peptide
source                     1..8
                           mol_type = protein
                           organism = synthetic construct
SEQUENCE: 94
GFTFRTYG                                                             8

SEQ ID NO: 95              moltype = AA  length = 15
FEATURE                    Location/Qualifiers
REGION                     1..15
                           note = synthetic construct; peptide
source                     1..15
                           mol_type = protein
                           organism = synthetic construct
SEQUENCE: 95
CARGGDQWLV PFDNW                                                    15

SEQ ID NO: 96              moltype = AA  length = 5
FEATURE                    Location/Qualifiers
REGION                     1..5
                           note = synthetic construct; peptide
SITE                       3
                           note = Xaa - Xaa = any amino acid
source                     1..5
                           mol_type = protein
                           organism = synthetic construct
SEQUENCE: 96
LPXSG                                                                5

SEQ ID NO: 97              moltype = AA  length = 5
FEATURE                    Location/Qualifiers
REGION                     1..5
                           note = synthetic construct; peptide
SITE                       3
                           note = Xaa - Xaa = any amino acid
source                     1..5
```

```
                        mol_type = protein
                        organism = synthetic construct
SEQUENCE: 97
LPXAG                                                                     5

SEQ ID NO: 98           moltype = AA   length = 5
FEATURE                 Location/Qualifiers
REGION                  1..5
                        note = synthetic construct; peptide
SITE                    3
                        note = Xaa - Xaa = any amino acid
source                  1..5
                        mol_type = protein
                        organism = synthetic construct
SEQUENCE: 98
LPXTG                                                                     5

SEQ ID NO: 99           moltype = AA   length = 5
FEATURE                 Location/Qualifiers
REGION                  1..5
                        note = synthetic construct; peptide
SITE                    3
                        note = Xaa - Xaa = any amino acid
source                  1..5
                        mol_type = protein
                        organism = synthetic construct
SEQUENCE: 99
LAXTG                                                                     5

SEQ ID NO: 100          moltype = AA   length = 5
FEATURE                 Location/Qualifiers
REGION                  1..5
                        note = synthetic construct; peptide
source                  1..5
                        mol_type = protein
                        organism = synthetic construct
SEQUENCE: 100
LAETG                                                                     5

SEQ ID NO: 101          moltype = AA   length = 5
FEATURE                 Location/Qualifiers
REGION                  1..5
                        note = synthetic construct; peptide
SITE                    3
                        note = Xaa - Xaa = any amino acid
source                  1..5
                        mol_type = protein
                        organism = synthetic construct
SEQUENCE: 101
LPXTA                                                                     5

SEQ ID NO: 102          moltype = AA   length = 5
FEATURE                 Location/Qualifiers
REGION                  1..5
                        note = synthetic construct; peptide
source                  1..5
                        mol_type = protein
                        organism = synthetic construct
SEQUENCE: 102
NPQTN                                                                     5

SEQ ID NO: 103          moltype = DNA   length = 22
FEATURE                 Location/Qualifiers
misc_feature            1..22
                        note = synthetic construct; nucleic acid sequence
source                  1..22
                        mol_type = other DNA
                        organism = synthetic construct
SEQUENCE: 103
caggtgcagc tgcaggagtc sg                                                 22

SEQ ID NO: 104          moltype = DNA   length = 21
FEATURE                 Location/Qualifiers
misc_feature            1..21
                        note = synthetic construct; nucleic acid sequence
source                  1..21
                        mol_type = other DNA
                        organism = synthetic construct
SEQUENCE: 104
```

```
caggtacagc tgcagcagtc a                                          21

SEQ ID NO: 105          moltype = DNA   length = 22
FEATURE                 Location/Qualifiers
misc_feature            1..22
                        note = synthetic construct; nucleic acid sequence
source                  1..22
                        mol_type = other DNA
                        organism = synthetic construct
SEQUENCE: 105
caggtgcagc tacagcagtg gg                                         22

SEQ ID NO: 106          moltype = DNA   length = 21
FEATURE                 Location/Qualifiers
misc_feature            1..21
                        note = synthetic construct; nucleic acid sequence
source                  1..21
                        mol_type = other DNA
                        organism = synthetic construct
SEQUENCE: 106
gaggtgcagc tgktggagwc t                                          21

SEQ ID NO: 107          moltype = DNA   length = 21
FEATURE                 Location/Qualifiers
misc_feature            1..21
                        note = synthetic construct; nucleic acid sequence
source                  1..21
                        mol_type = other DNA
                        organism = synthetic construct
SEQUENCE: 107
gaggtgcagc tgktggagwc c                                          21

SEQ ID NO: 108          moltype = DNA   length = 23
FEATURE                 Location/Qualifiers
misc_feature            1..23
                        note = synthetic construct; nucleic acid sequence
source                  1..23
                        mol_type = other DNA
                        organism = synthetic construct
SEQUENCE: 108
caggtccagc tkgtrcagtc tgg                                        23

SEQ ID NO: 109          moltype = DNA   length = 22
FEATURE                 Location/Qualifiers
misc_feature            1..22
                        note = synthetic construct; nucleic acid sequence
source                  1..22
                        mol_type = other DNA
                        organism = synthetic construct
SEQUENCE: 109
cagrtcacct tgaaggagtc tg                                         22

SEQ ID NO: 110          moltype = DNA   length = 23
FEATURE                 Location/Qualifiers
misc_feature            1..23
                        note = synthetic construct; nucleic acid sequence
source                  1..23
                        mol_type = other DNA
                        organism = synthetic construct
SEQUENCE: 110
caggtgcagc tggtgsartc tgg                                        23

SEQ ID NO: 111          moltype = DNA   length = 20
FEATURE                 Location/Qualifiers
misc_feature            1..20
                        note = synthetic construct; nucleic acid sequence
source                  1..20
                        mol_type = other DNA
                        organism = synthetic construct
SEQUENCE: 111
cagggtgact gagggcgtag                                            20

SEQ ID NO: 112          moltype = DNA   length = 20
FEATURE                 Location/Qualifiers
misc_feature            1..20
                        note = synthetic construct; nucleic acid sequence
source                  1..20
                        mol_type = other DNA
                        organism = synthetic construct
```

```
SEQUENCE: 112
gttgggaagg ttctgacacc                                               20

SEQ ID NO: 113          moltype = DNA  length = 20
FEATURE                 Location/Qualifiers
misc_feature            1..20
                        note = synthetic construct; nucleic acid sequence
source                  1..20
                        mol_type = other DNA
                        organism = synthetic construct
SEQUENCE: 113
gacatccaga tgacccagtc                                               20

SEQ ID NO: 114          moltype = DNA  length = 21
FEATURE                 Location/Qualifiers
misc_feature            1..21
                        note = synthetic construct; nucleic acid sequence
source                  1..21
                        mol_type = other DNA
                        organism = synthetic construct
SEQUENCE: 114
gacatccagt tgacccagtc t                                             21

SEQ ID NO: 115          moltype = DNA  length = 20
FEATURE                 Location/Qualifiers
misc_feature            1..20
                        note = synthetic construct; nucleic acid sequence
source                  1..20
                        mol_type = other DNA
                        organism = synthetic construct
SEQUENCE: 115
gccatccgga tgacccagtc                                               20

SEQ ID NO: 116          moltype = DNA  length = 20
FEATURE                 Location/Qualifiers
misc_feature            1..20
                        note = synthetic construct; nucleic acid sequence
source                  1..20
                        mol_type = other DNA
                        organism = synthetic construct
SEQUENCE: 116
gatattgtga tgacccagac                                               20

SEQ ID NO: 117          moltype = DNA  length = 20
FEATURE                 Location/Qualifiers
misc_feature            1..20
                        note = synthetic construct; nucleic acid sequence
source                  1..20
                        mol_type = other DNA
                        organism = synthetic construct
SEQUENCE: 117
gatattgtga tgactcagtc                                               20

SEQ ID NO: 118          moltype = DNA  length = 20
FEATURE                 Location/Qualifiers
misc_feature            1..20
                        note = synthetic construct; nucleic acid sequence
source                  1..20
                        mol_type = other DNA
                        organism = synthetic construct
SEQUENCE: 118
gatgttgtga tgactcagtc                                               20

SEQ ID NO: 119          moltype = DNA  length = 20
FEATURE                 Location/Qualifiers
misc_feature            1..20
                        note = synthetic construct; nucleic acid sequence
source                  1..20
                        mol_type = other DNA
                        organism = synthetic construct
SEQUENCE: 119
gaaattgtgt tgacacagtc                                               20

SEQ ID NO: 120          moltype = DNA  length = 20
FEATURE                 Location/Qualifiers
misc_feature            1..20
                        note = synthetic construct; nucleic acid sequence
source                  1..20
                        mol_type = other DNA
```

```
                        organism = synthetic construct
SEQUENCE: 120
gaaatagtga tgacgcagtc                                                    20

SEQ ID NO: 121          moltype = DNA   length = 21
FEATURE                 Location/Qualifiers
misc_feature            1..21
                        note = synthetic construct; nucleic acid sequence
source                  1..21
                        mol_type = other DNA
                        organism = synthetic construct
SEQUENCE: 121
gaaattgtgt tgacgcagtc t                                                  21

SEQ ID NO: 122          moltype = DNA   length = 20
FEATURE                 Location/Qualifiers
misc_feature            1..20
                        note = synthetic construct; nucleic acid sequence
source                  1..20
                        mol_type = other DNA
                        organism = synthetic construct
SEQUENCE: 122
gacatcgtga tgacccagtc                                                    20

SEQ ID NO: 123          moltype = DNA   length = 21
FEATURE                 Location/Qualifiers
misc_feature            1..21
                        note = synthetic construct; nucleic acid sequence
source                  1..21
                        mol_type = other DNA
                        organism = synthetic construct
SEQUENCE: 123
cttgacactg atgtctctgg g                                                  21

SEQ ID NO: 124          moltype = DNA   length = 18
FEATURE                 Location/Qualifiers
misc_feature            1..18
                        note = synthetic construct; nucleic acid sequence
source                  1..18
                        mol_type = other DNA
                        organism = synthetic construct
SEQUENCE: 124
tgaggagacg gtgaccag                                                      18

SEQ ID NO: 125          moltype = DNA   length = 20
FEATURE                 Location/Qualifiers
misc_feature            1..20
                        note = synthetic construct; nucleic acid sequence
source                  1..20
                        mol_type = other DNA
                        organism = synthetic construct
SEQUENCE: 125
tgaagagacg gtgaccattg                                                    20

SEQ ID NO: 126          moltype = DNA   length = 19
FEATURE                 Location/Qualifiers
misc_feature            1..19
                        note = synthetic construct; nucleic acid sequence
source                  1..19
                        mol_type = other DNA
                        organism = synthetic construct
SEQUENCE: 126
tgaggagacg gtgaccgtg                                                     19

SEQ ID NO: 127          moltype = DNA   length = 21
FEATURE                 Location/Qualifiers
misc_feature            1..21
                        note = synthetic construct; nucleic acid sequence
source                  1..21
                        mol_type = other DNA
                        organism = synthetic construct
SEQUENCE: 127
tttgatctcc agcttggtcc c                                                  21

SEQ ID NO: 128          moltype = DNA   length = 21
FEATURE                 Location/Qualifiers
misc_feature            1..21
                        note = synthetic construct; nucleic acid sequence
source                  1..21
```

```
                            mol_type = other DNA
                            organism = synthetic construct
SEQUENCE: 128
tttgatatcc actttggtcc c                                                   21

SEQ ID NO: 129              moltype = DNA   length = 21
FEATURE                     Location/Qualifiers
misc_feature                1..21
                            note = synthetic construct; nucleic acid sequence
source                      1..21
                            mol_type = other DNA
                            organism = synthetic construct
SEQUENCE: 129
tttaatctcc agtcgtgtcc c                                                   21

SEQ ID NO: 130              moltype = DNA   length = 21
FEATURE                     Location/Qualifiers
misc_feature                1..21
                            note = synthetic construct; nucleic acid sequence
source                      1..21
                            mol_type = other DNA
                            organism = synthetic construct
SEQUENCE: 130
tttgatytcc accttggtcc c                                                   21

SEQ ID NO: 131              moltype = AA   length = 212
FEATURE                     Location/Qualifiers
REGION                      1..212
                            note = synthetic construct; peptide
source                      1..212
                            mol_type = protein
                            organism = synthetic construct
SEQUENCE: 131
SYELTQLPSV SVSLGQTARI TCEGNNIGSK AVHWYQQKPG LAPGLLIYDD DERPSGVPDR    60
FSGSNSGDTA TLTISGAQAG DEADYYCQVW DSSAYVFGGG TQLTVTGQPK AAPSVTLFPP   120
SSEELQANKA TLVCLISDFY PGAVTVAWKA DSSPVKAGVE TTTPSKQSNN KYAASSYLSL   180
TPEQWKSHKS YSCQVTHEGS TVEKTVAPTE CS                                 212

SEQ ID NO: 132              moltype = AA   length = 447
FEATURE                     Location/Qualifiers
REGION                      1..447
                            note = synthetic construct; peptide
source                      1..447
                            mol_type = protein
                            organism = synthetic construct
SEQUENCE: 132
QEQQKESGGG LFKPTDTLTL TCTASGFDIS SYYMSWVRQA PGNGLEWIGA IGISGNAYYA    60
SWAKSRSTIT RNTNLNTVTL KMTSLTAADT ATYFCARDHP TYGMDLWGPG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 133              moltype = AA   length = 447
FEATURE                     Location/Qualifiers
REGION                      1..447
                            note = synthetic construct; peptide
source                      1..447
                            mol_type = protein
                            organism = synthetic construct
SEQUENCE: 133
QIQLQQSGPE VVKPGASVKI SCKASGYTFT DYYITWVKQK PGQGLEWIGW IYPGSGNTKY    60
NEKFKGKATL TVDTSSSTAF MQLSSLTSED TAVYFCANYG NYWFAYWGQG TQVTVSAAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 134              moltype = AA   length = 218
FEATURE                     Location/Qualifiers
REGION                      1..218
                            note = synthetic construct; peptide
source                      1..218
                            mol_type = protein
                            organism = synthetic construct
```

-continued

```
SEQUENCE: 134
DIVLTQSPAS LAVSLGQRAT ISCKASQSVD FDGDSYMNWY QQKPGQPPKV LIYAASNLES      60
GIPARFSGSG SGTDFTLNIH PVEEEDAATY YCQQSNEDPW TFGGGTKLEI KRTVAAPSVF     120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 135          moltype = AA   length = 5
FEATURE                 Location/Qualifiers
REGION                  1..5
                        note = synthetic construct; peptide
SITE                    3
                        note = Xaa - Xaa = any amino acid
source                  1..5
                        mol_type = protein
                        organism = synthetic construct
SEQUENCE: 135
LPXTG                                                                  5

SEQ ID NO: 136          moltype = AA   length = 5
FEATURE                 Location/Qualifiers
REGION                  1..5
                        note = synthetic construct; peptide
SITE                    3
                        note = Xaa - Xaa = any amino acid
source                  1..5
                        mol_type = protein
                        organism = synthetic construct
SEQUENCE: 136
LPXAG                                                                  5

SEQ ID NO: 137          moltype = AA   length = 5
FEATURE                 Location/Qualifiers
REGION                  1..5
                        note = synthetic construct; peptide
SITE                    3
                        note = Xaa - Xaa = any amino acid
source                  1..5
                        mol_type = protein
                        organism = synthetic construct
SEQUENCE: 137
LPXSG                                                                  5

SEQ ID NO: 138          moltype = AA   length = 5
FEATURE                 Location/Qualifiers
REGION                  1..5
                        note = synthetic construct; peptide
SITE                    3
                        note = Xaa - Xaa = any amino acid
source                  1..5
                        mol_type = protein
                        organism = synthetic construct
SEQUENCE: 138
LAXTG                                                                  5

SEQ ID NO: 139          moltype = AA   length = 5
FEATURE                 Location/Qualifiers
REGION                  1..5
                        note = synthetic construct; peptide
SITE                    3
                        note = Xaa - Xaa = any amino acid
source                  1..5
                        mol_type = protein
                        organism = synthetic construct
SEQUENCE: 139
LPXTG                                                                  5

SEQ ID NO: 140          moltype = AA   length = 5
FEATURE                 Location/Qualifiers
REGION                  1..5
                        note = synthetic construct; peptide
source                  1..5
                        mol_type = protein
                        organism = synthetic construct
SEQUENCE: 140
NPQTG                                                                  5

SEQ ID NO: 141          moltype = AA   length = 370
FEATURE                 Location/Qualifiers
REGION                  1..370
```

```
                        note = synthetic construct; peptide
source                  1..370
                        mol_type = protein
                        organism = synthetic construct
SEQUENCE: 141
EVEVPDPNDP  LGPLDGQDGP  IPTLKGYFLN  FLEPVNNITI  VQGQTAILHC  KVAGNPPPNV   60
RWLKNDAPVV  QEPRRIIIRK  TEYGSRLRIQ  DLDTTDTGYY  QCVATNGMKT  ITATGVLFVR  120
LGPTHSPNHN  FQDDYHEDGF  CQPYRGIACA  RFIGNRTIYV  DSLQMQGEIE  NRITAAFTMI  180
GTSTHLSDQC  SQFAIPSFCH  FVFPLCDARS  RAPKPRELCR  DECEVLESDL  CRQEYTIARS  240
NPLILMRLQL  PKCEALPMPE  SPDAANCMRI  GIPAERLGRY  HQCYNGSGTD  YRGTASTTKS  300
GHQCQPWALQ  HPHSHHLSST  DFPELGGGHA  YCRNPGGQME  GPWCFTQNKN  VRMELCDVPS  360
CSPRDSSKMG                                                              370

SEQ ID NO: 142          moltype = AA   length = 370
FEATURE                 Location/Qualifiers
REGION                  1..370
                        note = synthetic construct; peptide
source                  1..370
                        mol_type = protein
                        organism = synthetic construct
SEQUENCE: 142
EVEDSEAIDT  LGQPDGPDSP  LPTLKGYFLN  FLEPVNNITI  VQGQTAILHC  KVAGNPPPNV   60
RWLKNDAPVV  QEPRRVIIRK  TEYGSRLRIQ  DLDTTDTGYY  QCVATNGLKT  ITATGVLYVR  120
LGPTHSPNHN  FQDDDQEDGF  CQPYRGIACA  RFIGNRTIYV  DSLQMQGEIE  NRITAAFTMI  180
GTSTQLSDQC  SQFAIPSFCH  FVFPLCDARS  RAPKPRELCR  DECEVLENDL  CRQEYTIARS  240
NPLILMRLQL  PKCEALPMPE  SPDAANCMRI  GIPAERLGRY  HQCYNGSGAD  YRGMASTTKS  300
GHQCQPWALQ  HPHSHRLSST  EFPELGGGHA  YCRNPGGQME  GPWCFTQNKN  VRVELCDVPP  360
CSPRDGSKMG                                                              370
```